(12) United States Patent
Holmquist et al.

(10) Patent No.: US 8,034,627 B2
(45) Date of Patent: Oct. 11, 2011

(54) METHODS FOR DETECTING DIHYDROXYVITAMIN D METABOLITES BY MASS SPECTROMETRY

(75) Inventors: Brett Holmquist, Mission Viejo, CA (US); Nigel Clarke, Oceanside, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 12/630,796

(22) Filed: Dec. 3, 2009

(65) Prior Publication Data

US 2011/0133069 A1 Jun. 9, 2011

(51) Int. Cl.
G01N 24/00 (2006.01)
(52) U.S. Cl. ........................................ 436/173
(58) Field of Classification Search .................... 436/173
See application file for complete search history.

(56) References Cited

U.S. PATENT DOCUMENTS

| | | | |
|---|---|---|---|
| 6,787,660 | B1 | 9/2004 | Armbruster et al. |
| 7,321,116 | B2 * | 1/2008 | Picard et al. ............... 250/288 |
| 7,348,137 | B2 * | 3/2008 | Caulfield et al. ........... 435/4 |
| 7,618,827 | B2 | 11/2009 | Steven |
| 7,745,226 | B2 | 6/2010 | Clarke et al. |
| 2003/0171605 | A1 | 9/2003 | Reddy et al. |
| 2006/0054807 | A1 | 3/2006 | Picard et al. |
| 2008/0241955 | A1 | 10/2008 | Purkayastha et al. |

FOREIGN PATENT DOCUMENTS

| | | |
|---|---|---|
| WO | WO-95/33279 | 12/1995 |
| WO | WO-2008/097246 | 8/2008 |

OTHER PUBLICATIONS

Ascalone et al, Stereospecific determination of amisulpride, a new benzamide derivative, in human plasma and urine by automated solid-phase extraction and liquid chromatography on a chiral column. application to pharmacokinetics, Journal of Chromatography B., 676:95-105, 1996.
Coldwell et al., Measurement of Vitamins D2 and D3 and Seven Major Metabolites in a Single Sample of Human Plasma Using Gas Chromatography/Mass Spectrometry, Biomedical and Environmental Mass Spectrometry, 16:81-85 (1988).
Office Action dated Sep. 29, 2009 for EP Application No. 06749272.8.
US Office Action on dated Apr. 12, 2010 for U.S. Appl. No. 11/386,215.
Extended Search Report dated Dec. 22, 2010 in EP application 08853843.
International Search Report and Written Opinion dated Jan. 26, 2011 in application PCT/US2010/056461.
International Search Report and Written Opinion dated Jan. 27, 2011 in application PCT/US2010/057627.

(Continued)

*Primary Examiner* — Jill Warden
*Assistant Examiner* — Monique T Cole
(74) *Attorney, Agent, or Firm* — Foley & Lardner LLP

(57) ABSTRACT

Provided are methods of detecting the presence or amount of a dihydroxyvitamin D metabolite in a sample using mass spectrometry. The methods generally comprise ionizing a dihydrorxyvitamin D metabolite in a sample and detecting the amount of the ion to determine the presence or amount of the vitamin D metabolite in the sample. In certain preferred embodiments the methods include immunopurifying the dihydroxyvitamin D metabolites prior to mass spectrometry. Also provided are methods to detect the presence or amount of two or more dihydroxyvitamin D metabolites in a single assay.

24 Claims, 40 Drawing Sheets

OTHER PUBLICATIONS

International Search Report and Written Opinion dated Feb. 7, 2011 in application PCT/US2010/059765.
International Search Report and Written Opinion dated Feb. 8, 2011 in application PCT/US2010/059746.
International Search Report dated Jan. 14, 2011 in PCT/US2010/056886.
International Search Report dated Feb. 11, 2011 in application PCT/US2010/059771.
Kobayashi, et al, Production of a group-specific antibody to 1 alpha,25-dihydroxyvitamin D and its derivatives having the 1 alpha,3 beta-dihydroxylated A-ring structure, Steroids, (1994), 59(7):404-11.
U.S. Office Action dated Dec. 17, 2010 in U.S. Appl. No. 11/946,765.
US Notice of Allowance dated Mar. 2, 2011 in U.S. Appl. No. 11/386,215.
US Notice of Allowance dated Mar. 3, 2011 in U.S. Appl. No. 11/946,765.
US Office Action dated Jan. 6, 2011 in U.S. Appl. No. 12/630,790.
US Office Action dated Oct. 5, 2010 in U.S. Appl. No. 11/386,215.
Yeung, et al, The role of mass spectrometry in vitamin D research, Mass Spec Reviews, (1995), 14(3):179-194.
International Preliminary Report on Patentability dated Oct. 9, 2007 in related application PCT/US2006/012539.
International Preliminary Report on Patentability dated Jun. 1, 2010 in related application PCT/US2008/084709.
US Office Action dated Jun. 24, 2010 in related U.S. Appl. No. 11/946,765.
US Office Action dated Jun. 28, 2010 in related U.S. Appl. No. 12/630,790.

* cited by examiner

METHODS FOR DETECTING DIHYDROXYVITAMIN D METABOLITES BY MASS SPECTROMETRY

FIELD OF THE INVENTION

The invention relates to the detection of dihydroxyvitamin D metabolites. In a particular aspect, the invention relates to methods for detecting vitamin D metabolites by mass spectrometry.

BACKGROUND OF THE INVENTION

Vitamin D is an essential nutrient with important physiological roles in the positive regulation of calcium ($Ca^{2+}$) homeostasis. Vitamin D can be made de novo in the skin by exposure to sunlight or it can be absorbed from the diet. There are two forms of vitamin D; vitamin $D_2$ (ergocalciferol) and vitamin $D_3$ (cholecalciferol). Vitamin $D_3$ is the form synthesized de novo by animals. It is also a common supplement added to milk products and certain food products produced in the United States. Both dietary and intrinsically synthesized vitamin $D_3$ must undergo metabolic activation to generate bioactive metabolites. In humans, the initial step of vitamin $D_3$ activation occurs primarily in the liver and involves hydroxylation to form the intermediate metabolite 25-hydroxyvitamin $D_3$ (25-hydroxycholecalciferol; calcifediol; $25OHD_3$). Calcifediol is the major form of vitamin $D_3$ in the circulation. Circulating $25OHD_3$ is then converted by the kidney to 1α,25-dihydroxyvitamin $D_3$ (calcitriol; 1α,25 $(OH)_2 D_3$), which is generally believed to be the metabolite of vitamin $D_3$ with the highest biological activity.

Vitamin $D_2$ is derived from fungal and plant sources. Many over-the-counter dietary supplements contain ergocalciferol (vitamin $D_2$) rather than cholecalciferol (vitamin $D_3$). Drisdol, the only high-potency prescription form of vitamin D available in the United States, is formulated with ergocalciferol. Vitamin $D_2$ undergoes a similar pathway of metabolic activation in humans as vitamin $D_3$, forming the metabolites 25-hydroxyvitamin $D_2$ ($25OHD_2$) and 1α,25-dihydroxyvitamin $D_3$ (1α,25$(OH)_2 D_2$). Vitamin $D_2$ and vitamin $D_3$ have long been assumed to be biologically equivalent in humans, however recent reports suggest that there may be differences in the bioactivity and bioavailability of these two forms of vitamin D (Armas et. al., (2004) J. Clin. Endocrinol, Metab. 89:5387-5391).

Measurement of vitamin D, the inactive vitamin D precursor, is rare in clinical settings. Rather, serum levels of 25-hydroxyvitamin $D_3$, 25-hydroxyvitamin $D_2$, and total 25-hydroxyvitamin D ("25OHD") are useful indices of vitamin D nutritional status and the efficacy of certain vitamin D analogs. The measurement of 25OHD is commonly used in the diagnosis and management of disorders of calcium metabolism. In this respect, low levels of 25OHD are indicative of vitamin D deficiency associated with diseases such as hypocalcemia, hypophosphatemia, secondary hyperparathyroidism, elevated alkaline phosphatase, osteomalacia in adults and rickets in children. In patients suspected of vitamin D intoxication, elevated levels of 25OHD distinguishes this disorder from other disorders that cause hypercalcemia.

Measurement of 1α,25$(OH)_2 D$ is also used in clinical settings. Certain disease states can be reflected by circulating levels of 1α,25$(OH)_2 D$. For example, kidney disease and kidney failure often result in low levels of 1α,25$(OH)_2 D$. Elevated levels of 1α,25$(OH)_2 D$ may be indicative of excess parathyroid hormone or can be indicative of certain diseases such as sarcoidosis or certain types of lymphomas.

Detection of vitamin D metabolites has been accomplished by radioimmunoassay with antibodies co-specific for $25OHD_2$ and $25OHD_3$. Because the current immunologically-based assays do not separately resolve $25OHD_2$ and $25OHD_3$, the source of any nutritional deficiency of vitamin D cannot be determined without resorting to other tests. Reports have been published that disclose methods for detecting specific vitamin D metabolites using mass spectrometry. In some of the reports, the vitamin D metabolites are derivatized prior to mass spectrometry, but in others, they are not. For example Holmquist, et al., U.S. patent application Ser. No. 11/946,765, filed Dec. 28, 2007; Yeung B, et al., J. Chromatogr. 1993, 645(1):115-23; Higashi T, et al., Steroids. 2000, 65(5):281-94; Higashi T, et al., Biol Pharm Bull. 2001, 24(7):738-43; Higashi T, et al., J Pharm Biomed Anal. 2002, 29(5):947-55; Higashi T, et al., Anal. Biochanal Chem, 2008, 391:229-38; and Aronov, et al., Anal Bioanal Chem, 2008, 391:1917-30 disclose methods for detecting various vitamin D metabolites by derivatizing the metabolites prior to mass spectrometry. Methods to detect underivatized vitamin D metabolites are reported in Clarke, et al., in U.S. patent application Ser. Nos. 11/101,166, filed Apr. 6, 2005, and 11/386,215, filed Mar. 21, 2006, and Singh, et al., in U.S. patent application Ser. No. 10/977,121, filed Oct. 24, 2004.

SUMMARY OF THE INVENTION

The present invention provides methods for detecting the presence or amount of a dihydroxyvitamin D metabolite in a sample by mass spectrometry, including tandem mass spectrometry.

In one aspect, methods are provided for determining the amount of 1α,25-dihydroxyvitamin $D_2$ (1α,25$(OH)_2 D_2$) in a sample by mass spectrometry. These methods include subjecting the sample to conditions suitable to generate one or more 1α,25$(OH)_2 D_2$ ions detectable by mass spectrometry; determining the amount of one or more of the 1α,25$(OH)_2 D_2$ ions by mass spectrometry; and relating the amount of 1α,25$(OH)_2 D_2$ ions determined to the amount of 1α,25$(OH)_2 D_2$ in the sample. In these methods, one or more 1α,25$(OH)_2 D_2$ ions include one or more ions selected from the group consisting of ions with a mass-to-charge ratio of 375.1±0.5, 393.1±0.5, 105.3±0.5, 157.0±0.5, and 225.0±0.5.

In another aspect, methods are provided for determining the amount of 1α,25-dihydroxyvitamin $D_3$ (1α,25$(OH)_2 D_3$) in a sample by mass spectrometry. These methods include subjecting the sample to conditions suitable to generate one or more 1α,25$(OH)_2 D_3$ ions detectable by mass spectrometry; determining the amount of one or more of the 1α,25$(OH)_2 D_3$ ions by mass spectrometry; and relating the amount of 1α,25$(OH)_2 D_3$ ions determined to the amount of 1α,25$(OH)_2 D_3$ in the sample. In these methods, one or more 1α,25$(OH)_2 D_3$ ions include one or more ions selected from the group consisting of ions with a mass-to-charge ratio of 363.1±0.5, 381.1±0.5, 105.1±0.5, 109.0±0.5, 156.9±0.5, and 159.2±0.5.

In another aspect, methods are provided for determining the amount of 1α,25-dihydroxyvitamin $D_2$ (1α,25$(OH)_2 D_2$) and 1α,25-dihydroxyvitamin $D_3$ (1α,25$(OH)_2 D_3$) in a sample by mass spectrometry. These methods include subjecting the sample under conditions suitable to generate one or more 1α,25$(OH)_2 D_2$ ions and one or more 1α,25$(OH)_2 D_3$ ions detectable by mass spectrometry; determining the amount of one or more of the 1α,25$(OH)_2 D_2$ ions and the amount of one or more of the 1α,25$(OH)_2 D_3$ ions by mass spectrometry; and relating the amount of 1α,25$(OH)_2 D_2$ ions and 1α,25$(OH)_2 D_3$ ions determined to the amount of 1α,25

$(OH)_2D_2$ and $1\alpha,25(OH)_2D_3$ in the sample. In these methods, one or more $1\alpha,25$-dihydroxyvitamin $D_2$ ($1\alpha,25(OH)_2D_2$) ions include one or more ions selected from the group consisting of ions with a mass-to-charge ratio of $375.1\pm0.5$, $393.1\pm0.5$, $105.3\pm0.5$, $157.0\pm0.5$, and $225.0\pm0.5$, and one or more $1\alpha,25(OH)_2D_3$ ions include one or more ions selected from the group consisting of ions with a mass-to-charge ratio of $363.1\pm0.5$, $381.1\pm0.5$, $105.1\pm0.5$, $109.0\pm0.5$, $156.9\pm0.5$, and $159.2\pm0.5$.

In some embodiments, mass spectrometry is tandem mass spectrometry.

In some embodiments, subjecting the sample to conditions suitable to generate one or more $1\alpha,25(OH)_2D_2$ ions includes volatilizing the sample by heating the sample with a laser, such as by laser diode thermal desorption (LDTD). In some embodiments, the volatized sample may be ionized with atmospheric pressure chemical ionization (APCI).

In some embodiments, the sample is not subjected to chromatography (including liquid chromatography) prior to mass spectrometry. Alternatively, the sample may be subjected to chromatography (including liquid chromatography) prior to mass spectrometry.

In another aspect, methods are provided for determining the amount of $1\alpha,25$-dihydroxyvitamin $D_2$ ($1\alpha,25(OH)_2D_2$) in a sample by tandem mass spectrometry. These methods include: (a) immunopurifying $1\alpha,25(OH)_2D_2$ from said sample; (b) further purifying the immunopurified $1\alpha,25(OH)_2 D_2$ from step (a) by high pressure liquid chromatography (HPLC); and (c) determining the amount of the $11\alpha,25(OH)_2D_2$ obtained from step (b) by tandem mass spectrometry. In these methods, tandem mass spectrometry includes: (1) generating one or more $1\alpha,25(OH)_2D_2$ precursor ions comprising one or more ions with a mass to charge ratio (m/z) of $375.1\pm0.5$ and $393.1\pm0.5$; (ii) generating one or more $1\alpha,25(OH)_2D_2$ fragment ions; and (iii) detecting the amount of one or more of said ions generated in step (i) or (ii) or both and relating the amount of detected ions to the amount of $11\alpha,25(OH)_2D_2$ in said sample. In some embodiments, the methods further comprise determining the amount of $1\alpha,25$-dihydroxyvitamin $D_2$ ($1\alpha,25(OH)_2D_3$) in a sample by tandem mass spectrometry.

In another aspect, methods are provided for determining the amount of $1(1\alpha,25$-dihydroxyvitamin $D_3$ ($1\alpha,25(OH)_2 D_3$) in a sample by tandem mass spectrometry. These methods include: (a) immunopurifying $1\alpha,25(OH)_2D_3$ from said sample; (b) further purifying the immunopurified $1\alpha,25(OH)_2 D_3$ from step (a) by high pressure liquid chromatography (HPLC); (c) determining the amount of the $1\alpha,25(OH)_2 D_3$ obtained from step (b) by tandem mass spectrometry. In these methods tandem mass spectrometry includes: (i) generating one or more $1\alpha,25(OH)_2D_3$ precursor ions comprising one or more ions with a mass to charge ratio (m/z) of $375.1\pm0.5$ and $393.1\pm0.5$; (ii) generating one or more $1\alpha,25(OH)_2D_3$ fragment ions; and (iii) detecting the amount of one or more of said ions generated in step (i) or (ii) or both and relating the amount of detected ions to the amount of $1\alpha,25(OH)_2D_3$ in said sample. In some embodiments, the methods further comprise determining the amount of $1\alpha,25$-dihydroxyvitamin ($1\alpha,25(OH)_2D_2$) in a sample by tandem mass spectrometry.

In some embodiments, the step of immunopurifying utilizes immunoparticles. In some related embodiments, immunoparticles comprise anti-dihydroxyvitamin D antibodies.

In the methods described herein which utilize tandem mass spectrometry, some embodiments may include one or more $1\alpha,25(OH)_2D_2$ precursor ions with a mass-to-charge ratio of $375.1\pm0.5$ and fragment ions with a mass-to-charge ratio of $105.3\pm0.5$ and/or $157.0\pm0.5$. In some embodiments, the one or more $1\alpha,25(OH)_2D_2$ ions may include a precursor ion with a mass-to-charge ratio of $393.1\pm0.5$ and fragment ions with a mass-to-charge ratio of $157.0\pm0.5$ and/or $225.0\pm0.5$.

In the methods described herein which utilize tandem mass spectrometry, some embodiments may include one or more $1\alpha,25(OH)_2D_3$ precursor ions with a mass-to-charge ratio of $363.1\pm0.5$ and a fragment ion with a mass-to-charge ratio of $105.1\pm0.5$ and $156.9\pm0.5$. In some embodiments, one or more $1\alpha,25(OH)_2D_3$ ions may include a precursor ion with a mass-to-charge ratio of $381.1\pm0.5$ and fragment ions with a mass-to-charge ratio of $109.0\pm0.5$, and/or $156.9\pm0.5$, and/or $159.2\pm0.5$.

In preferred embodiments, the samples analyzed for dihydroxyvitamin D content are biological samples; preferably plasma or serum.

As used herein, the term "dihydroxyvitamin D metabolite" refers to any dihydroxylated vitamin D species that may be found in the circulation of an animal which is fowled by a biosynthetic or metabolic pathway for vitamin D or a synthetic vitamin D analog. Preferably the dihydroxyvitamin D metabolite is hydroxylated at the 1 and 25 position. In particularly preferred embodiments, the vitamin D metabolite is $1\alpha,25$-dihydroxyvitamin $D_3$ ($1\alpha,25(OH)_2D_3$) or $1\alpha,25$-dihydroxyvitamin $D_2$ ($1\alpha,25(OH)_2D_2$). In certain preferred embodiments the dihydroxyvitamin D metabolites are naturally present in a body fluid of a mammal, more preferably a human. In certain particularly preferred embodiments, the methods as described herein detect $1\alpha,25$-dihydroxyvitamin $D_3$ ($1\alpha,25(OH)_2D_3$) and/or $1\alpha,25$-dihydroxyvitamin $D_2$ ($1\alpha,25(OH)_2D_2$) and do not detect one or more dihydroxyvitamin-D metabolites selected from the group consisting of 24,25-dihydroxyvitamin D; 25,26-dihydroxyvitamin D; and $1\alpha,3\alpha$-dihydroxyvitamin D.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "immunopurification" or "immunopurify" refers to a purification procedure that utilizes antibodies, including polyclonal or monoclonal antibodies, to enrich the one or more analytes of interest. Immunopurification can be performed using any of the immunopurification methods well known in the art. Often the immunopurification procedure utilizes antibodies bound, conjugated or otherwise attached to a solid support, for example a column, well, tube, gel, capsule, particle or the like. Immunopurification as used herein includes without limitation procedures often referred to in the art as immunoprecipitation, as well as procedures often referred to in the art as affinity chromatography.

As used herein, the term "immunoparticle" refers to a capsule, bead, gel particle or the like that has antibodies bound, conjugated or otherwise attached to its surface (either on and/or in the particle). In certain preferred embodiments, immunoparticles are sepharose or agarose beads. In alternative preferred embodiments, immunoparticles are glass, plastic or silica beads, or silica gel.

As used herein, the term "anti-dihydroxyvitamin D antibody" refers to any polyclonal or monoclonal antibody that has an affinity for one or more dihydroxyvitamin D metabolites. In certain preferred embodiments the anti-dihydroxyvitamin D antibodies bind 1α,25(OH)$_2$D$_3$ and 1α,25(OH)$_2$D$_2$. In some preferred embodiments the anti-dihydroxyvitamin D antibodies bind 1α,25(OH)$_2$D$_3$ and 1α,25(OH)$_2$D$_2$ with equal or similar affinity. In other preferred embodiments the anti-dihydroxyvitamin D antibodies bind 1α,25(OH)$_2$D$_3$ with significantly higher affinity than 1α,25(OH)$_2$D$_2$; in alternative preferred embodiments the anti-dihydroxyvitamin D antibodies bind 1α,25(OH)$_2$D$_2$ with significantly higher affinity than 1α,25(OH)$_2$D$_3$. In various embodiments the specificity of anti-dihydroxyvitamin D antibodies to chemical species other than dihydroxyvitamin D metabolites may vary; for example in certain preferred embodiments the anti-dihydroxyvitamin D antibodies are specific for dihydroxyvitamin D metabolites and thus have little or no affinity for chemical species other than dihydroxyvitamin D metabolites (e.g., other vitamin D metabolites such as vitamin D or 25-hydroxyvitamin D), whereas in other preferred embodiments the anti-dihydroxyvitamin D antibodies are non-specific and thus bind certain chemical species other than dihydroxyvitamin D metabolites (for example a non-specific anti-dihydroxyvitamin D antibody may bind other vitamin D or vitamin D metabolites such as vitamin D or 25-hydroxyvitamin D).

As used herein, "biological sample" refers to any sample from a biological source. As used herein, "body fluid" means any fluid that can be isolated from the body of an individual. For example, "body fluid" may include blood, plasma, serum, bile, saliva, urine, tears, perspiration, and the like.

As used herein, "derivatizing" means reacting two molecules to form a new molecule. Derivatizing agents may include Cookson-type reagents (e.g., 4-substituted 1,2,4-triazoline-3,5-diones; TAD); isothiocyanate groups, dinitrofluorophenyl groups, nitrophenoxycarbonyl groups, and/or phthalaldehyde groups. In certain preferred embodiments, derivitization is performed using methods such as those disclosed in, for example, Vreeken, et., al., Biol. Mass Spec. 22:621-632; Yeung B, et al., J. Chromatogr. 1993, 645(1):115-23; Higashi T, et al., Biol Pharm Bull. 2001, 24(7):738-43; or Higashi T, et al., J Pharm Biomed Anal. 2002, 29(5):947-55.

In preferred embodiments the derivatizing agents are Cookson-type reagents. Particularly preferred derivatizing reagents include 4-phenyl-1,2,4-triazoline-3,5-dione (PTAD); 4'-carboxyphenyl-TAD; 4-[4-(6-methoxy-2-benzoxazolyl)phenyl]-1,2,4-triazoline-3,5-dione (MBOTAD); 4-[2-(6,7-dimethoxy-4-methyl-3-oxo-3,4-dihydroquinoxalypethyl]-1,2,4-triazoline-3,5-dione (DMEQTAD); 4-nitrophenyl-TAD; 4-pentafluorophenyl-TAD; 4-ferrocenylethyl-TAD; 4-quarternaryamine-TAD; and the like. Derivatization of vitamin D metabolites by Cookson-type reagents can be conducted by any appropriate method. See, e.g., Holmquist, et al., U.S. patent application Ser. No. 11/946,765, filed Dec. 28, 2007; Yeung B, et al., J. Chromatogr. 1993, 645(1):115-23; Higashi T, et al., Steroids. 2000, 65(5):281-94; Higashi T, et al., Biol Phami Bull. 2001, 24(7):738-43; Higashi T, et al., J Pharm Biomed Anal. 2002, 29(5):947-55; Higashi T, et al., Anal. Biochanal Chem, 2008, 391:229-38; and Aronov, et al., Anal Bioanal Chem, 2008, 391:1917-30.

In certain preferred embodiments derivatization is performed prior to chromatography; however in other preferred embodiments derivatization is performed after chromatography, for example using methods similar to those described in Vreeken, et., al., Biol. Mass Spec. 22:621-632.

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI), laser diode thermal desorption (LDTD), or electrospray ionization (ESI), may be used in embodiments of the present invention. In certain preferred embodiments, vitamin D metabolites are measured using APCI or LDTD in positive ion mode.

In preferred embodiments, one or more separately detectable internal standards are provided in the sample, the amount of which are also determined in the sample. In these embodiments, all or a portion of both the analyte(s) of interest and the internal standard(s) present in the sample are ionized to produce a plurality of ions detectable in a mass spectrometer, and one or more ions produced from each are detected by mass spectrometry. Preferably, the internal standard(s) are one or more of 25OHD$_2$-[6, 19, 19]-$^2$H$_3$, 25OHD$_2$-[26, 26, 26, 27, 27, 27]-$^2$H$_6$, 25OHD$_3$-[6, 19, 19]-$^2$H$_3$, 25OHD$_3$-[26, 26, 26, 27, 27, 27]-$^2$H$_6$, 1α,25(OH)$_2$D$_2$-[6, 19, 19]-$^2$H$_3$, 1α,25(OH)$_2$D$_2$-[26, 26, 26, 27, 27, 27]-$^2$H$_6$, 1α,25(OH)$_2$D$_3$-[6, 19, 19]-$^2$H$_3$, and 1α,25(OH)$_2$D$_3$-[26, 26, 26, 27, 27, 27]-$^2$H$_6$.

One or more separately detectable internal standards may be provided in the sample. In these embodiments, the one or more internal standards may undergo derivatization along with the endogenous vitamin D metabolites, in which case ions of the derivatized internal standards are detected by mass spectrometry. In these embodiments, the presence or amount of ions generated from the analyte of interest may be related to the presence of amount of analyte of interest in the sample. In some embodiments, the internal standards may be isotopically labeled versions of vitamin D metabolites, such as 25OHD$_2$-[6, 19, 19]-$^2$H$_3$, 25OHD$_2$-[26, 26, 26, 27, 27, 27]-$^2$H$_6$, 25OHD$_3$-[6, 19, 19]-$^2$H$_3$, 25OHD$_3$-[26, 26, 26, 27, 27, 27]-$^2$H$_6$, 1α,25(OH)$_2$D$_2$-[6, 19, 19]-$^2$H$_3$, 1α,25(OH)$_2$D$_2$-[26, 26, 26, 27, 27, 27]-$^2$H$_6$, 1α,25(OH)$_2$D$_3$-[6, 19, 19]-$^2$H$_3$, and 1α,25(OH)$_2$D$_3$-[26, 26, 26, 27, 27, 27]-$^2$H$_6$.

Ions detectable in a mass spectrometer may be generated for each of the above identified exemplary internal standards, as demonstrated in Examples 5 and 6, and FIGS. 2, 4-5, 7, and 9-10.

As used herein, an "isotopic label" produces a mass shift in the labeled molecule relative to the unlabeled molecule when analyzed by mass spectrometric techniques. Examples of suitable labels include deuterium ($^2$H), $^{13}$C, and $^{15}$N. For example, 25OHD$_2$-[6, 19, 19]-$^2$H$_3$ and 25OHD$_3$-[6, 19, 19]-$^2$H$_3$ have masses about 3 mass units higher than native 25OHD$_2$ and 25OHD$_3$. The isotopic label can be incorporated at one or more positions in the molecule and one or more kinds of isotopic labels can be used on the same isotopically labeled molecule.

In other embodiments, the amount of the vitamin D metabolite ion or ions may be determined by comparison to one or more external reference standards. Exemplary external reference standards include blank plasma or serum spiked with one or more of 25OHD$_2$-[6, 19, 19]-$^2$H$_3$, 25OHD$_2$-[26, 26, 26, 27, 27, 27]-$^2$H$_6$, 25OHD$_3$-[6, 19, 19]-$^2$H$_3$, 25OHD$_3$-[26, 26, 26, 27, 27, 27]-$^2$H$_6$, 1α,25(OH)$_2$D$_2$-[6, 19, 19]-$^2$H$_3$, 1α,25(OH)$_2$D$_2$-[26, 26, 26, 27, 27, 27]-$^2$H$_6$, 1α,25(OH)$_2$D$_3$-[6, 19, 19]-$^2$H$_3$, and 1α,25(OH)$_2$D$_3$-[26, 26, 26, 27, 27, 27]-$^2$H$_6$. External standards typically will undergo the same treatment and analysis as any other sample to be analyzed, including treatment with one or more Cookson-type reagents prior to mass spectrometry.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term in "gas chromatography" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "large particle column" or "extraction column" refers to a chromatography column containing an average particle diameter greater than about 50 µm.

As used herein, the term "analytical column" refers to a chromatography column having sufficient chromatographic plates to effect a separation of materials in a sample that elute from the column sufficient to allow a determination of the presence or amount of an analyte. In a preferred embodiment the analytical column contains particles of about 5 µm in diameter. Such columns are often distinguished from "extraction columns", which have the general purpose of separating or extracting retained material from non-retained materials in order to obtain a purified sample for further analysis.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. Nos. 6,204,500, entitled "Mass Spectrometry From Surfaces;" 6,107,623, entitled "Methods and Apparatus for Tandem Mass Spectrometry:" 6,268,144, entitled "DNA Diagnostics Based On Mass Spectrometry;" 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal, Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser diode thermal desorption (LDTD) is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample may then be drawn into an ionization source, where the gas phase sample is ionized in preparation for analysis in the mass spectrometer. When using LDTD, ionization of the gas phase sample may be accomplished by any suitable technique known in the art, such as by ionization with a corona discharge (for example by APCI).

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 80% to 120%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

As used herein, unless otherwise stated, the singular forms "a," "an," and "the" include plural reference. Thus, for example, a reference to "a protein" includes a plurality of protein molecules.

DETAILED DESCRIPTION OF THE INVENTION

Figure 1A:
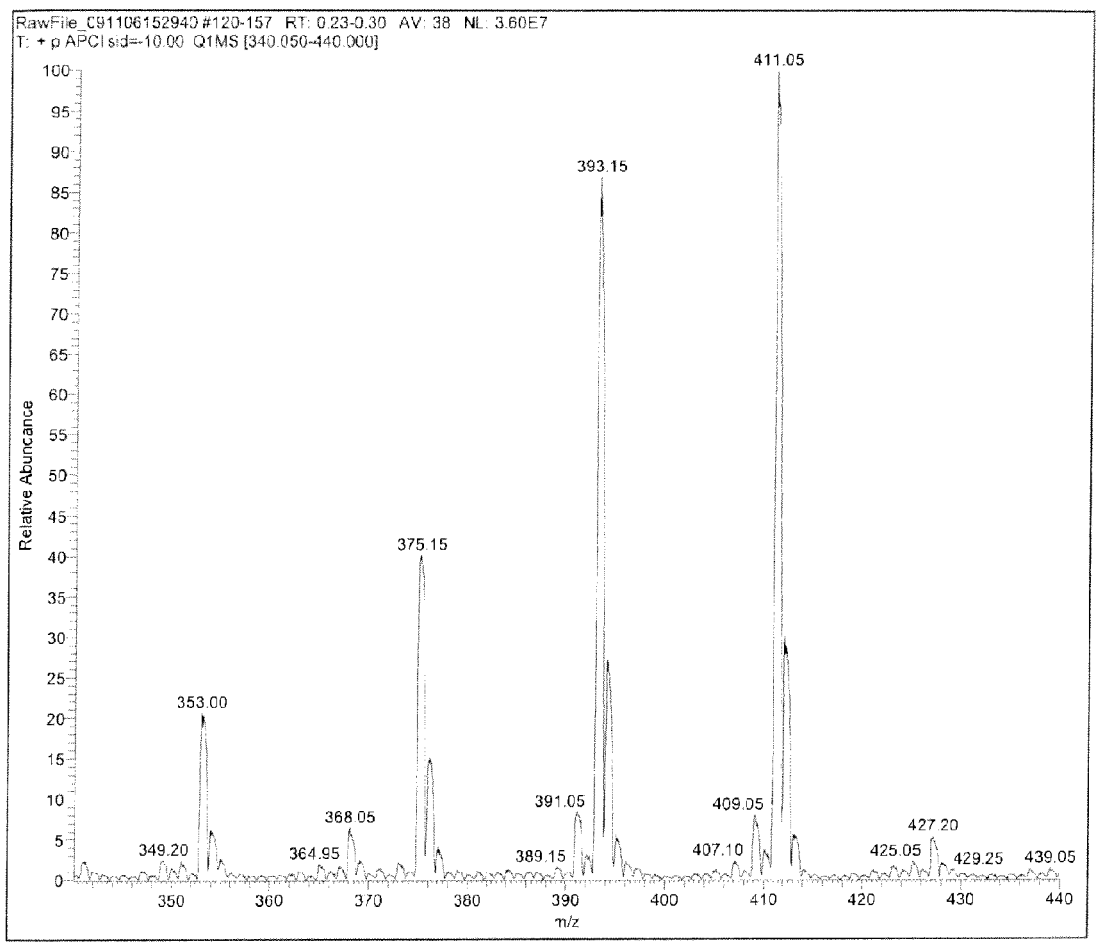
FIG. 1A shows an exemplary Q1 scan spectrum (covering the m/z range of about 340 to 440) for 1α,25-dihydroxyvitamin $D_2$ ions.
Figure 1B:
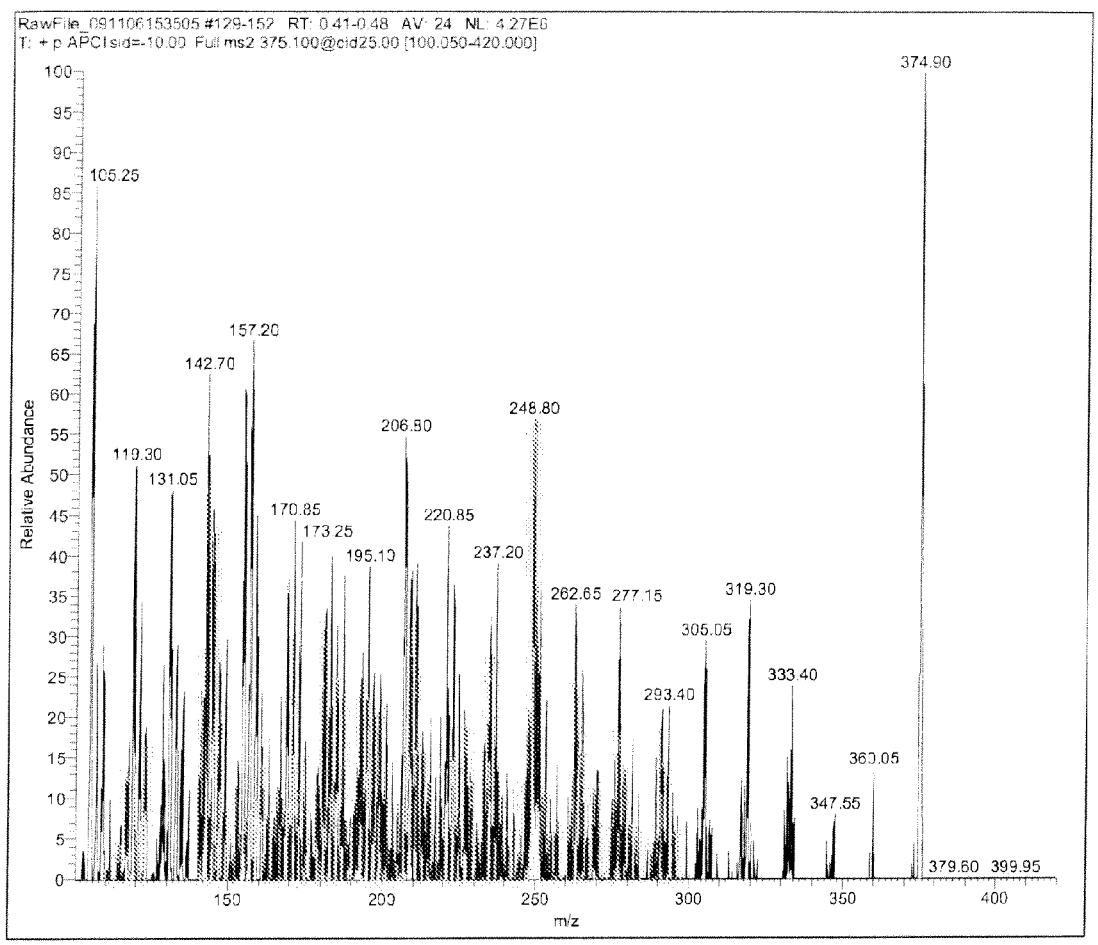
FIG. 1B shows an exemplary product ion spectra (covering the m/z range of about 100 to 420) for fragmentation of the 1α,25-dihydroxyvitamin $D_2$ precursor ion with m/z of about 375.1.
Figure 1C:
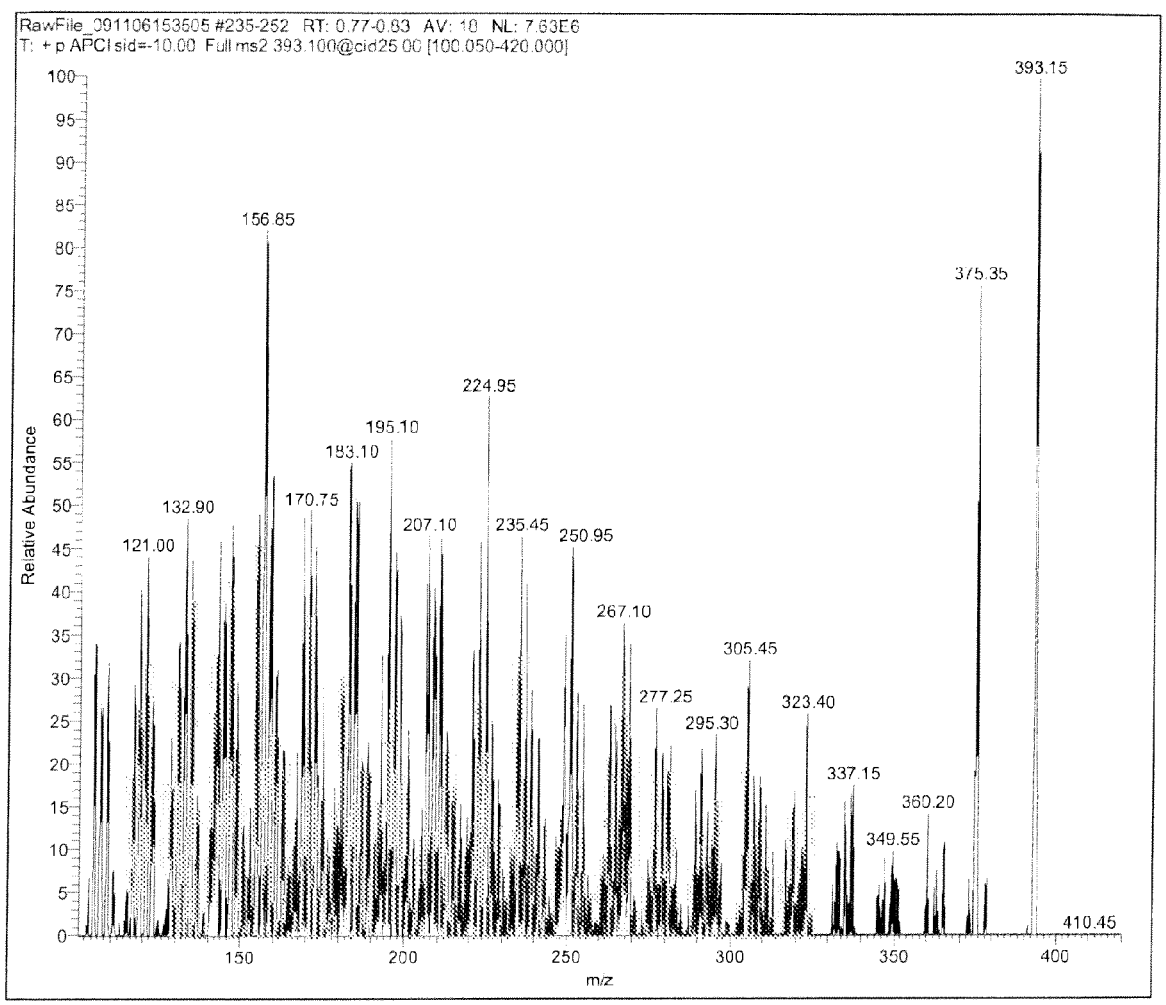
FIG. 1C shows an exemplary product ion spectra (covering the m/z range of about 100 to 420) for fragmentation of the 1α,25-dihydroxyvitamin $D_2$ precursor ion with m/z of about 393.1.
Figure 1D:
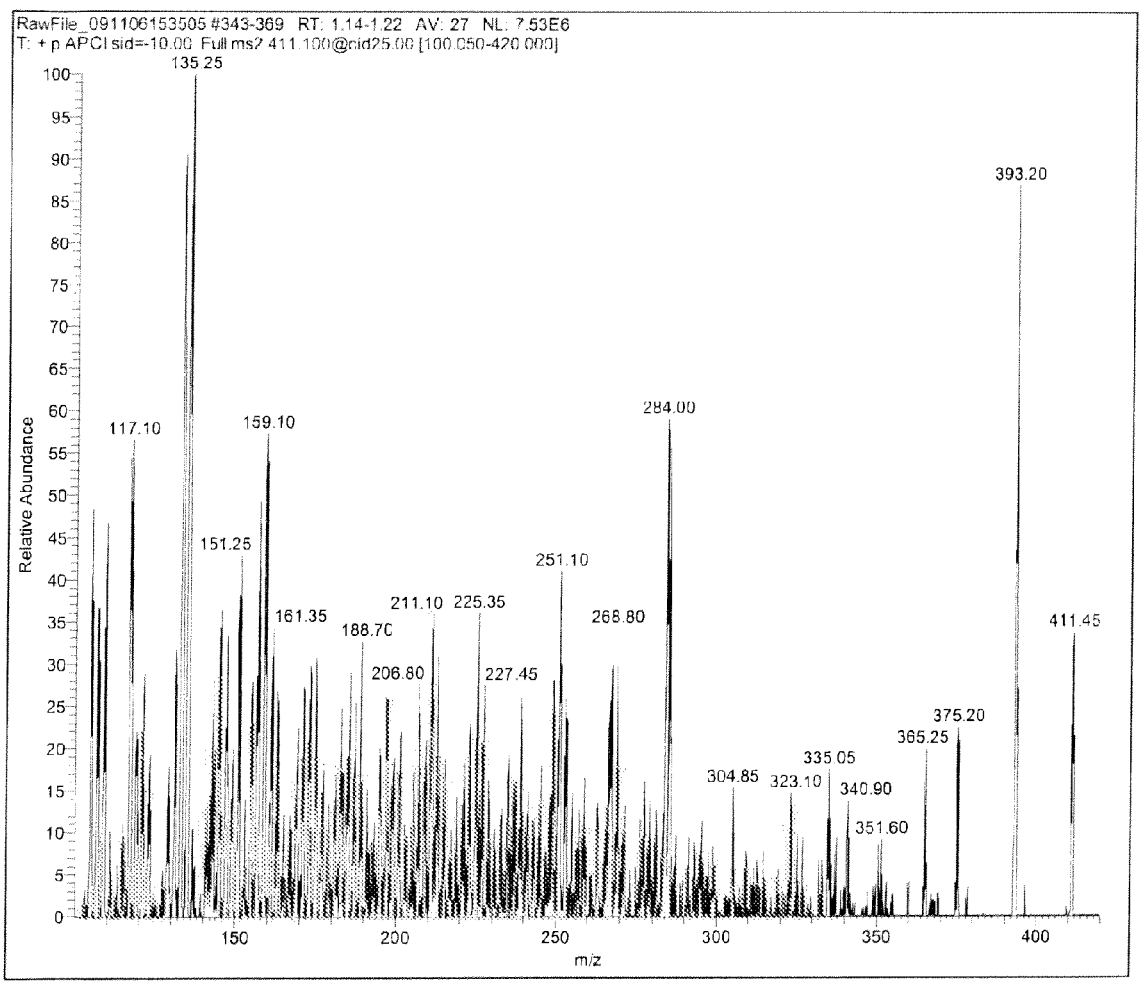
FIG. 1D shows an exemplary product ion spectra (covering the m/z range of about 100 to 420) for fragmentation of the 1α,25-dihydroxyvitamin $D_2$ precursor ion with m/z of about 411.1. Details are described in Example 5.

Methods are described for detecting and quantifying dihydroxyvitamin D metabolites in a test sample. Some preferred methods disclosed herein utilize liquid chromatography (LC), most preferably HPLC, to purify selected analytes, and combine this purification with unique methods of mass spectrometry (MS), thereby providing a high-throughput assay system for detecting and quantifying dihydroxyvitamin D metabolites in a test sample. In certain particularly preferred embodiments, dihydroxyvitamin D metabolites are immunopurified prior to mass spectrometry. The preferred embodiments are particularly well suited for application in large clinical laboratories. Methods of detecting and quantifying dihydroxyvitamin D metabolites are provided that have enhanced specificity and are accomplished in less time and with less sample preparation than required in other dihydroxyvitamin D metabolite assays.

Suitable test samples include any test sample that may contain the analyte of interest. For example, samples obtained during the manufacture of an analyte can be analyzed to determine the composition and yield of the manufacturing process. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably humans. Particularly preferred samples include blood, plasma, serum, hair, muscle, urine, saliva, tear, cerebrospinal fluid, or other tissue sample. Such samples may be obtained, for example, from a patient; that is, a living person presenting oneself in a clinical setting for diagnosis, prognosis, or treatment of a disease or condition. The test sample is preferably obtained from a patient, for example, blood serum.

Sample Preparation for Mass Spectrometry

Methods may be used prior to mass spectrometry to enrich dihydroxyvitamin D metabolites relative to other components in the sample, or to increase the concentration of the dihydroxyvitamin D metabolites in the sample. Such methods include, for example, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, extraction, precipitation, centrifugation, delipidization, dilution, combinations thereof and the like. Protein precipitation is one preferred method of preparing a liquid biological sample, such as scrum or plasma, for chromatography. Such protein purification methods are well known in the art, for example, Poison et al., *Journal of Chromatography B* 785:263-275 (2003), describes protein precipitation methods suitable for use in the methods of the invention. Protein precipitation may be used to remove most of the protein from the sample leaving dihydroxyvitamin D metabolites soluble in the supernatant. The samples can be centrifuged to separate the liquid supernatant from the precipitated proteins. The resultant supernatant can then be applied to liquid chromatography and subsequent mass spectrometry analysis. In one embodiment of the invention, the protein precipitation involves adding one volume of the liquid sample (e.g. plasma) to about four volumes of methanol. In certain embodiments, the use of protein precipitation obviates the need for high turbulence liquid chromatography ("HTLC") or on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography ("HTLC").

Immunopurification.

In particularly preferred embodiments, the methods include immunopurifying dihydroxyvitamin D metabolites prior to mass spectrometry analysis. The immunopurification step may be performed using any of the immunopurification methods well known in the art. Often the immunopurification procedure utilizes antibodies bound, conjugated, immobilized or otherwise attached to a solid support, for example a column, well, tube, capsule, particle or the like. Generally, immunopurification methods involve (1) incubating a sample containing the analyte of interest with antibodies such that the analyte binds to the antibodies, (2) performing one or more washing steps, and (3) eluting the analyte from the antibodies.

In certain embodiments the incubation step of the immunopurification is performed with the antibodies free in solution and the antibodies are subsequently bound or attached to a solid surface prior to the washing steps. In certain embodiments this can be achieved using a primary antibody that is an anti-dihydroxyvitamin D antibody and a secondary antibody attached to a solid surface that has an affinity to the primary anti-dihydroxyvitamin D antibody. In alternative embodiments, the primary antibody is bound to the solid surface prior to the incubation step.

Appropriate solid supports include without limitation tubes, slides, columns, beads, capsules, particles, gels, and the like. In some preferred embodiments, the solid support is a multi-well plate, such as, for example, a 96 well plate, a 384-well plate or the like. In certain preferred embodiments the solid support are sephararose or agarose beads or gels. There are numerous methods well known in the art by which antibodies (for example, an anti-dihydroxyvitamin D antibody or a secondary antibody) may be bound, attached, immobilized or coupled to a solid support, e.g., covalent or non-covalent linkages adsorption, affinity binding, ionic linkages and the like. In certain preferred embodiments antibodies are coupled using CNBr, for example the antibodies may be coupled to CNBr activated sepharose. In other embodiments, the antibody is attached to the solid support through an antibody binding protein such as protein A, protein G, protein A/G, or protein L.

The washing step of the immunopurification methods generally involve washing the solid support such that the dihydroxyvitamin D metabolites remain bound to the anti-dihydroxyvitamin D antibodies on the solid support. The elution step of the immunopurification generally involves the addition of a solution that disrupts the binding of dihydroxyvitamin D metabolites to the anti-dihydroxyvitamin D antibodies. Exemplary elution solutions include organic solutions (preferably ethanol), salt solutions, and high or low pH solutions.

In certain preferred embodiments, immunopurification is performed using immunoparticles having anti-dihydroxyvitamin D antibodies. In certain preferred embodiments the test sample possibly containing dihydroxyvitamin D metabolites and the immunoparticles are mixed in a tube for incubation and binding of dihydroxyvitamin D metabolites to the anti-dihydroxyvitamin D antibodies attached to the immunoparticles; the tube is centrifuged leaving the immunoparticles in a pellet; the supernatant is removed; the immunoparticles are washed one or more times by adding a solution to the pellet and recentrifuging; and the dihydroxyvitamin D metabolites are eluted by adding an elution solution to the immunoparticles, the tube is centrifuged leaving the immunoparticles in a pellet; and the supernatant containing dihydroxyvitamin D metabolites is collected. In related preferred embodiments, the immunopurification is performed using a column or cartridge that contains immunoparticles having anti-dihydroxyvitamin D antibodies. Preferably, the such column or cartridge is configured and arranged in a manner to allow solutions to flow through while keeping the immunoparticles contained therein. In certain preferred embodiments, the solution is forced through the column or cartridge by gravity, centrifugation or pressure. The use of columns may improve the ease of performing the incubation, washing and elution steps. In some preferred embodiments, the immunopurification is performed by affinity chromatography; preferably automated affinity chromatography; preferably affinity-HPLC; or preferably affinity chromatography using an automated system such as the AKTA FPLC Chromatographic system sold commercially by GE Healthcare (formerly Amersham biosciences).

In certain embodiments, the sample preparation and immunopurification can be performed using methods and reagents from commercially available kits. For example, IDS Inc (Fountain Hills, Ariz.) offers a 1,25-Dihydroxy Vitamin D $^{125}$I Radioimmunoassay kit (Catalogue Number AA-54F1) that includes directions and reagents for extracting and immunoextracting dihydroxyvitamin D prior to the radioimmunoassay (RIA). See the "Product Support" document for the Catalogue Number AA-54F1 IDS, Inc., kit which is hereby incorporated by reference in its entirety. In particular, the IDS dihydroxyvitamin D RIA kit includes a dextran sulphate/magnesium chloride delipidization step and an immunoextraction step using an immunocapsule device containing a suspension of particles to which is attached a monoclonal antibody specific for 1,25 dihydroxyvitamin D. Accordingly, in certain embodiments of the methods described herein, the samples are subject to vitamin D immunopurification using the IDS kit or methods, reagents and dihydroxyvitamin D immunopurification devices similar to those provided in the IDS kit. Antibodies and dihydroxy purification immunopurification devices are also provided with the 1,25-(OH)2-Vitamin D ImmunoTube ELISA Kit (Catalog Number 30-2113) offered commercially by ALPO Diagnostics (Salem, N.H.). The kit includes an anti 1,25-(OH)$_2$ vitamin-D detection antibody (Catalog number K2113A1), ImmunoTube columns for immunopurification of 1,25-dihydroxyvitamin D (Catalog Number K2113.SI) as well as buffers and other reagents that may be used to immunopurify 1α,25-dihydroxyvitamin D. In certain embodiments of the methods described herein, one or more of the components of the ALPO Diagnostics kit are used in to immunopurify 1α,25-dihydroxyyitamin D.

Liquid Chromatography.

Generally, chromatography is performed prior to mass spectrometry, preferably the chromatography is liquid chromatography, more preferably high performance liquid chromatography (HPLC). In some preferred embodiments the chromatography is not gas chromatography. Preferably, the methods of the invention are performed without subjecting the samples, or the dihydroxyvitamin D metabolites of interest, to gas chromatography prior to mass spectrometric analysis.

Liquid chromatography (LC) including high-performance liquid chromatography (HPLC) rely on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process. HPLC has been successfully applied to the separation of compounds in biological samples. But a significant amount of sample preparation is required prior to the separation and subsequent analysis with a mass spectrometer (MS), making this technique labor intensive. In addition, most HPLC systems do not utilize the mass spectrometer to its fullest potential, allowing only one HPLC system to be connected to a single MS instrument, resulting in lengthy time requirements for performing a large number of assays.

Various methods have been described involving the use of HPLC for sample clean-up prior to mass spectrometry analysis. See, e.g., Taylor et al., *Therapeutic Drug Monitoring* 22:608-12 (2000) (manual precipitation of blood samples, followed by manual C18 solid phase extraction, injection into an HPLC for chromatography on a C18 analytical column, and MS/MS analysis); and Salm et al., *Clin. Therapeutics* 22 Supl. B:B71-B85 (2000) (manual precipitation of blood samples, followed by manual C18 solid phase extraction, injection into an HPLC for chromatography on a C18 analytical column, and MS/MS analysis).

One of skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), choice of gradient elution and the gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

Recently, high turbulence liquid chromatography ("HTLC"), also called high throughput liquid chromatography, has been applied for sample preparation prior to analysis by mass spectrometry. See, e.g., Zimmer et al., *J. Chromatogr. A* 854:23-35 (1999); see also, U.S. Pat. Nos. 5,968, 367; 5,919,368; 5,795,469; and 5,772,874. Traditional HPLC analysis relies on column packings in which laminar flow of the sample through the column is the basis for separation of the analyte of interest from the sample. The skilled artisan will understand that separation in such columns is a diffusional process. In contrast, it is believed that turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the dihydroxyvitamin D metabolite of interest prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. In certain embodiments of the method, samples are subjected to protein precipitation as described above prior to loading on the HTLC column; in alternative embodiments, the samples may be loaded directly onto the HTLC without being subjected to protein precipitation.

Recently, research has shown that epimerization of the hydroxyl group of the A-ring of vitamin $D_3$ metabolites is an important aspect of vitamin $D_3$ metabolism and bioactivation, and that depending on the cell types involved, 3-C epimers of vitamin $D_3$ metabolites (e.g., 3-epi-25(OH)$D_3$; 3-epi-24,25 (OH)$_2D_3$; and 3-epi-1,25(OH)$_2D_3$) are often major metabolic products. See Kamao et al., *J. Biol. Chem.*, 279:15897-15907 (2004). Kamao et al., further provides methods of separating various vitamin D metabolites, including 3-C epimers, using Chiral HPLC. Accordingly, the invention also provides methods of detecting the presence, absence and/or amount of a specific epimer of one or more vitamin D metabolites, preferably vitamin $D_3$ metabolites, in a sample by (1) separating one or more specific vitamin D metabolites by chiral chromatography, preferably chiral HPLC; and (2) detecting the presence and/or amount of one or more vitamin D metabolites using mass spectrometry methods as described herein. The chiral chromatography procedures described in Kamao et al., are suitable for the methods of the invention, however, one of ordinary skill in the art understands that there are numerous other chiral chromatography methods that would also be suitable. In preferred embodiments the method includes, separating 25(OH)$D_3$ from 3-epi-25(OH)$D_3$, if present in a sample, using chiral chromatography; and detecting the presence and/or amount of the 25(OH)$D_3$ and the 3-epi-25(OH)$D_3$ in the sample using mass spectrometry. In related embodiments, the method includes separating 1α,25(OH)$_2D_3$ from 3-epi-1α,25 (OH)$_2D_3$, if present in a sample, using chiral chromatography; and detecting the presence and/or amount of the 1α,25 (OH)$_2D_3$ and the 3-epi-1α,25(OH)$_2D_3$ in the sample using mass spectrometry. In certain embodiments of the invention, chiral chromatography is used in conjunction with the HTLC methods described above.

Detection and Quantitation by Mass Spectrometry

Disclosed are methods for detecting the presence or amount of one or more dihydroxyvitamin D metabolites in a sample. In certain aspects the method involves ionizing the dihydroxyvitamin D metabolite(s), detecting the ion(s) by mass spectrometry, and relating the presence or amount of the ion(s) to the presence or amount of the dihydroxyvitamin D metabolite(s) in the sample. The method may include (a) purifying a dihydroxyvitamin D metabolite, if present in the sample, (b) ionizing the purified dihydroxyvitamin D metabolite and (c) detecting the presence or amount of the ion, wherein the presence or amount of the ion is related to the presence or amount of the dihydroxyvitamin D metabolite in the sample. In preferred embodiments, the ionizing step (b) may include (i) ionizing a dihydroxyvitamin D metabolite, if present in the sample, to produce an ion; (ii) isolating the dihydroxyvitamin D metabolite ion by mass spectrometry to provide a precursor ion; and (iii) effecting a collision between the isolated precursor ion and an inert collision gas to produce at least one fragment ion detectable in a mass spectrometer. In certain preferred embodiments the precursor ion is a protonated and dehydrated ion of the dihydroxyvitamin D metabolite.

Further provided is a method for determining the presence or amount of a dihydroxyvitamin D metabolite in a test sample by tandem mass spectrometry. The method may involve (a) generating a protonated and dehydrated precursor ion of the dihydroxyvitamin D metabolite; (b) generating one or more fragment ions of the precursor ion; and (c) detecting the presence or amount of one or more of the ions generated in step (a) or (b) or both and relating the detected ions to the presence or amount of the dihydroxyvitamin D metabolite in the sample.

In certain preferred embodiments of the invention, at least one fragment ion is detected, wherein the presence or amount of the precursor and/or at least one fragment ion is related to the presence or amount of the dihydroxyvitamin D metabolite in the sample. Preferably at least one fragment ion is specific for the dihydroxyvitamin D metabolite of interest. In some embodiments, the methods of the invention can be used to detect and quantify two or more dihydroxyvitamin D metabolites in a single assay.

Mass spectrometry is performed using a mass spectrometer which includes an ion source for ionizing the fractionated sample and creating charged molecules for further analysis. For example ionization of the sample may be performed by electrospray ionization (ESI), atmospheric pressure chemical ionization (APCI), photoionization, electron ionization, fast atom bombardment (FAB)/liquid secondary ionization (LSIMS), matrix assisted laser desorption ionization (MALDI), field ionization, field desorption, thermospray/ plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., m/z). Suitable analyzers for determining mass-to-charge ratios include quadropole analyzers, ion traps analyzers, and time-of-flight analyzers. The ions may be detected using several detection modes. For example, selected ions may be detected (i.e., using a selective ion monitoring mode (SIM)), or alternatively, ions may be detected using a scanning mode, e.g., multiple reaction monitoring (MRM) or selected reaction monitoring (SRM). Preferably, the mass-to-charge ratio is determined using a quadropole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas to produce the daughter ions. Because both the precursor and fragment ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MS$^n$." Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 100 to 1000 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted into an absolute amount of the original molecule. In certain preferred embodiments, an internal standard is used to generate a standard curve for calculating the quantity of the dihydroxyvitamin D metabolite. Methods of generating and using such standard curves are well known in the art and one of ordinary skill is capable of selecting an appropriate internal standard. For example, an isotope of a dihydroxyvitamin D metabolite may be used as an internal standard, in preferred embodiments the dihydroxyvitamin D metabolite is a deuterated dihydroxyvitamin D metabolite, for example $1\alpha,25(OH)_2D_2\text{-}[26,26,26,27,27,27]\text{-}^2H_6$ or $1\alpha,25(OH)_2D_3\text{-}[6,19,19]\text{-}^2H_3$ or both. Numerous other methods for relating the presence or amount of an ion to the presence or amount of the original molecule will be well known to those of ordinary skill in the art.

One or more steps of the methods described herein may be performed using automated machines. In certain embodiments, one or more purification steps are performed on line, and more preferably all of the purification and mass spectrometry steps may be performed in an on-line fashion.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy.

In particularly preferred embodiments dihydroxyvitamin D metabolites are detected and/or quantified using LC-MS/MS as follows. The samples are subjected to liquid chromatography, preferably HPLC, the flow of liquid solvent from the chromatographic column enters the heated nebulizer interface of a LC-MS/MS analyzer and the solvent/analyte mixture is converted to vapor in the heated tubing of the interface. The analytes (i.e. dihydroxyvitamin D metabolites), contained in the nebulized solvent, are ionized by the corona discharge needle of the interface, which applies a large voltage to the nebulized solvent/analyte mixture. The ions, i.e. precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass to charge ratios of the specific dihydroxyvitamin D metabolites to be analyzed. Precursor ions with the correct m/z ratios of the precursor ions of specific dihydroxyvitamin D metabolites are allowed to pass into the collision chamber (Q2), while unwanted ions with any other m/z collide with the sides of the quadrupole and are eliminated. Precursor ions entering Q2 collide with neutral Argon gas molecules and fragment. This process is called Collision Activated Dissociation (CAD). The fragment ions generated are passed into quadrupole 3 (Q3), where the fragment ions of the desired dihydroxyvitamin D metabolites are selected while other ions are eliminated.

The methods of the invention may involve MS/MS performed in either positive or negative ion mode. Using standard methods well known in the art, one of ordinary skill is capable of identifying one or more fragment ions of a particular precursor ion of a dihydroxyvitamin D metabolite that can be used for selection in quadrupole 3 (Q3).

If the precursor ion of a dihydroxyvitamin D metabolite of interest includes an alcohol or amine group, fragment ions are commonly formed that represent a dehydration or deamination of the precursor ion, respectfully. In the case of precursor ions that include an alcohol group, such fragment ions formed by dehydration are caused by a loss of one or more water molecules from the precursor ion (i.e., where the difference in m/z between the precursor ion and fragment ion is about 18 for the loss of one water molecule, or about 36 for the loss of two water molecules, etc.). In the case of precursor ions that include an amine group, such fragment ions formed by deamination are caused by a loss of one or more ammonia molecules (i.e. where the difference in m/z between the precursor ion and fragment ion is about 17 for the loss of one ammonia molecule, or about 34 for the loss of two ammonia molecules, etc.). Likewise, precursor ions that include one or more alcohol and amine groups commonly form fragment ions that represent the loss of one or more water molecules and/or one or more ammonia molecules (e.g., where the difference in m/z between the precursor ion and fragment ion is about 35 for the loss of one water molecule and the loss of one ammonia molecule). Generally, the fragment ions that represent dehydrations or deaminations of the precursor ion are not specific fragment ions for a particular analyte.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte (vitamin D metabolite) of interest. In certain embodiments, the area under the curves, or amplitude of the peaks, for fragment ion(s) and/or precursor ions are measured to determine the amount of a dihydroxyvitamin D metabolite. As described above, the relative abundance of a given ion can be converted into an absolute amount of the original analyte, i.e., dihydroxyvitamin D metabolite, using calibration standard curves based on peaks of one or more ions of an internal molecular standard, such as $25OHD_3$-[26,26,26,27,27,27]-$2H_6$.

In certain aspects of the invention, the quantity of various ions is determined by measuring the area under the curve or the amplitude of the peak and a ratio of the quantities of the ions is calculated and monitored (i.e. "daughter ion ratio monitoring"). In certain embodiments of the method, the ratio(s) of the quantity of a precursor ion and the quantity of one or more fragment ions of a dihydroxyvitamin D metabolite can be calculated and compared to the ratio(s) of a molecular standard of the dihydroxyvitamin D metabolite similarly measured. In embodiments where more than one fragment ion of a dihydroxyvitamin D metabolite is monitored, the ratio(s) for different fragment ions may be determined instead of or in addition to, the ratio of the fragment ion(s) compared to the precursor ion. In embodiments where such ratios are monitored, if there is a substantial difference in an ion ratio in the sample as compared to the molecular standard, it is likely that a molecule in the sample is interfering with the results. To the contrary, if the ion ratios in the sample and the molecular standard are similar, then there is increased confidence that there is no interference. Accordingly, monitoring such ratios in the samples and comparing the ratios to those of authentic molecular standards may be used to increase the accuracy of the method.

Detection and Quantitation by LDTD-MS/MS

In alternative embodiments, dihydroxyvitamin D metabolites in a sample may be detected and/or quantified using MS/MS as follows. The dihydroxyvitamin D metabolites are purified in a sample by liquid-liquid extraction, with the a portion of the resulting solution spotted in a LDTD well. The spotted sample is then heated indirectly with a laser which results in thermal desorption of dihydroxyvitamin D metabolites. The desorbed dihydroxyvitamin D metabolites then pass a corona discharge and are ionized before being introduced into a triple quadrupole MS instrument. Quadrupoles 1 and 3 (Q1 and Q3) are mass filters, allowing selection of ions (i.e., selection of "precursor" and "fragment" ions in Q1 and Q3, respectively) based on their mass-to-charge ratio (m/z). Quadrupole 2 (Q2) is a collision cell, where precursor ions are fragmented. The vitamin D metabolite ions, e.g. precursor ions, pass through the orifice of the instrument and enter a first quadrupole (Q1). The first quadrupole of the mass spectrometer (Q1) selects for molecules with the mass-to-charge ratios of a dihydroxyvitamin D metabolite. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral gas molecules, preferably argon, and fragment. The fragment ions generated are passed into quadrupole 3 (Q3), where the fragment ions of a dihydroxyvitamin D metabolite are selected while other ions are eliminated. By switching the m/z ratio selected in Q1, multiple precursor ions detected from a single sample.

In particularly preferred embodiments of the invention, the presence or absence or amount of two or more dihydroxyvitamin D metabolites in a sample are detected in a single assay using the above described MS/MS methods.

The following examples serve to illustrate the invention. These examples are in no way intended to limit the scope of the invention.

EXAMPLES

Example 1

Determination of 1α,25-dihydroxyvitamin $D_3$ and 1α,25-dihydroxyvitamin $D_2$ by LC-MS/MS 50 µl of an internal standard mixture (stripped serum spiked with 1α,25$(OH)_2D_3$-[6,19,19]-$^2H_3$ at 50 pg/50 microliters and 1α,25$(OH)_2D_2$-[26,26,26,27,27,27]-$^2H_6$ at 200 pg/50 microliters) was added to test tubes then 500 µl of calibrator solution, quality control test solution, or serum standard, followed by the internal standard mixture. The solutions were delipidized by adding 50 µl $MgCl_2$/dextran sulfate solution and mixing thoroughly. The tubes were then centrifuged for 20 minutes and 500 µl of supernatant was transferred to ImmunoTube cartridges containing anti-dihydroxyvitamin D immunocapsules from ALPCO Diagnostics (Catalog Number K2113.SI). The cartridges were incubated on a shaker at room temperature for two hours. The beads were then washed three times with 750 µl deionized water. The beads were drained between washes by centrifuging the cartridges. Dihydroxyvitamin D bound to the beads was eluted with 250 µl ethanol directly into a glass HPLC insert and then dried to completion under nitrogen. The samples were then derivatized by adding 50 µl of 50 microliters of 4-phenyl-1,2,4-triazoline-3,5-dione (PTAD) solution (0.8 mg/mL in acetonitrile). The dervitization reaction was stopped by adding 50 µl deionized water.

The HPLC inserts were then transferred to an HPLC autosampler for loading to the LC-MS/MS analyzer. LC-MS/MS was performed using a Thermo Finnigan LC-MS/MS analyzer (Thermo Finnigan Quantum TSQ (S/N: TQU00655)) with an atmospheric pressure chemical ionization (APCI) source as the detector. An autosampler was used to inject 90 µL of extracted sample supernatant onto an HPLC column. Liquid chromatography was performed with a Synergi™ Max-RP C-12 Phenomenex columns run at 0.8 mL/minute. Two mobile phase solutions were used for the HPLC: mobile phase A was 0.1% formic acid in HPLC-grade water and mobile phase B was 100% acetonitrile. The total run time was 5.00 min with the collection window between 1:31-2:31 (60 seconds). The starting condition (20 seconds)

was 50% mobile phase A and 50% mobile phase B; the gradient (160 seconds) was from 50% mobile phase A and 50% mobile phase B to 2% mobile phase A and 98% mobile phase B; the wash step (60 seconds) was 2% mobile phase A and 98% mobile phase B; and the reconditioning step was 50% mobile phase A and 50% mobile phase B.

The flow of liquid solvent exiting the HPLC column entered the heated nebulizer interface of the Thermo Finnigan LC-MS/MS analyzer and the dihydroxyvitamin D metabolites were measured using APCI in positive mode. The solvent/analyte mixture was first converted to vapor in the heated tubing of the interface. The analytes, contained in the nebulized solvent, were ionized (a positive charge added) by the corona discharge needle of the interface, which applies a large voltage to the nebulized solvent/analyte mixture. The ions pass through the orifice of the instrument and enter the first quadrupole. Quadrupoles 1 and 3 (Q1 and Q3) are mass filters, allowing selection of ions based on their mass to charge ratio (m/z). Quadrupole 2 (Q2) is the collision cell, where ions are fragmented.

The first quadrupole of the mass spectrometer (Q1) selected for molecules with the mass to charge ratios of $1\alpha,25(OH)_2D_2$, $1\alpha,25(OH)_2D_3$, $1\alpha,25(OH)_2D_2\text{-}[6,19,19]\text{-}^2H_3$ (internal standard) and $1\alpha,25(OH)_2D_3\text{-}[26,26,26,27,27,27]\text{-}^2H_6$ (internal standard). Ions with these m/z ratios (see table below) were allowed to pass into the collision chamber (Q2), while unwanted ions with any other m/z collide with the sides of the quadrupole and are eliminated. Ions entering Q2 collide with neutral Argon gas molecules and fragment. The fragment ions generated are passed into quadrupole 3 (Q3), where the fragment ions of $1\alpha,25(OH)_2D_2$, $1\alpha,25(OH)_2D_3$, $1\alpha,25(OH)_2D_2\text{-}[26,26,26,27,27,27]\text{-}^2H_6$ (internal standard) and $1\alpha,25(OH)_2D_3\text{-}[26,26,26,27,27,27]\text{-}^2H_6$ (internal standard) were selected (see table below) and other ions are eliminated. The following mass transitions were used for detection and quantitation during validation:

TABLE 1

Mass transitions for selected dihydroxyvitamin D metabolites

| Analyte | Precursor Ion | Product Ion |
|---|---|---|
| $1\alpha,25(OH)_2D_3$ | 574.37 | 314.12 |
| $1\alpha,25(OH)_2D_3\text{-}[6,19,19]\text{-}^2H_3$ (Internal Standard) | 577.37 | 317.12 |
| $1\alpha,25(OH)_2D_2$ | 586.37 | 314.12 |
| $1\alpha,25(OH)_2D_2\text{-}[26,26,26,27,27,27]\text{-}^2H_6$ (Internal Standard) | 592.37 | 314.12 |

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods.

Area ratios of the analyte and internal standards ($1\alpha,25(OH)_2D_3\text{-}[6,19,19]\text{-}^2H_3$ and $1\alpha,25(OH)_2D_2\text{-}[26,26,26,27,27,27]\text{-}^2H_6$) peaks were used to construct calibration curves, which were then used to calculate analyte concentrations. Using the calibration curves, the concentrations of $1\alpha,25(OH)_2D_2$ and $1\alpha,25(OH)_2D_3$ were quantitated in the patient samples.

Example 2

Intra-Assay and Inter-Assay Precision

Stock solutions of $1\alpha,25(OH)_2D_2$ and $1\alpha,25(OH)_2D_3$ were added to pooled serum to produce a Low Pool (10-15 ng/mL of each metabolite), a Medium-Low Pool (25-35 ng/mL of each metabolite), Medium-High Pool (55-65 ng/mL of each metabolite) and a High Pool (115-130 ng/mL). Four aliquots from each of the Low, Medium-Low, Medium-High and High Pools were analyzed in a single assay using the LC-MS/MS protocols described in Example 1. The following precision values were determined:

TABLE 2

Intra-Assay Variation: $1\alpha,25$-Dihydroxyvitamin $D_2$ ($1\alpha,25(OH)_2D_2$)

|  | Low | Medium-Low | Medium-High | High |
|---|---|---|---|---|
| 1 | 12 | 30 | 68 | 141 |
| 2 | 15 | 26 | 61 | 125 |
| 3 | 11 | 35 | 63 | 110 |
| 4 | 11 | 32 | 67 | 96 |
| Average (ng/mL) | 12.4 | 30.6 | 63.7 | 118.1 |
| CV (%) | 16.2% | 11.8% | 5.3% | 16.5% |

TABLE 3

Intra-Assay Variation: $1\alpha,25$-Dihydroxyvitamin $D_3$ ($1\alpha,25(OH)_2D_3$)

|  | Low | Medium-Low | Medium-High | High |
|---|---|---|---|---|
| 1 | 10 | 30 | 68 | 125 |
| 2 | 14 | 33 | 59 | 138 |
| 3 | 11 | 35 | 56 | 116 |
| 4 | 15 | 30 | 59 | 118 |
| Average (ng/mL) | 12.3 | 32.1 | 60.6 | 124.2 |
| CV (%) | 17.8% | 8.1% | 8.6% | 8.2% |

Example 3

Enrichment of Vitamin D Metabolites in Preparation for LDTD-MS/MS

All samples analyzed in Examples 5 and 6, below, were prepared for LDTD-MS/MS according to the following procedure. All extractions were performed in a 96-well plate. 50 µL of serum or calibrant solution was added to each well, along with 200 µL of either methanol or ethyl acetate extraction/internal standard solution. Plates were vigorously mixed for about 2 minutes at 1600 RPM, and subsequently centrifuged for about 30 minutes at 6000 g.

An automated pipettor was used to transfer 150 µL of supernatant (from methanol extractions) or organic layer (from ethyl acetate extractions) to a new 96 well plate. Liquids were evaporated under a stream of nitrogen. The residue was reconstituted in 100 µL of methanol, and about 2 to 5 µL of the methanol solution was spotted onto a well of a LazWell plate.

Example 4

Detection and Quantitation of Vitamin D Metabolites by MS/MS

MS/MS was performed using a Thermo Finnigan TSQ Vantage MS/MS system (Thermo Electron Corporation). The ionization source was a Laser Diode Thermal Desorption (LDTD) source from Phytronix Technologies (Quebec, QC, Canada). Laser intensity varied from 10% to 60% of maximum output during development experiments, and was set to about 25% maximum output for quantitative analysis.

Example 5

Figure 2A:
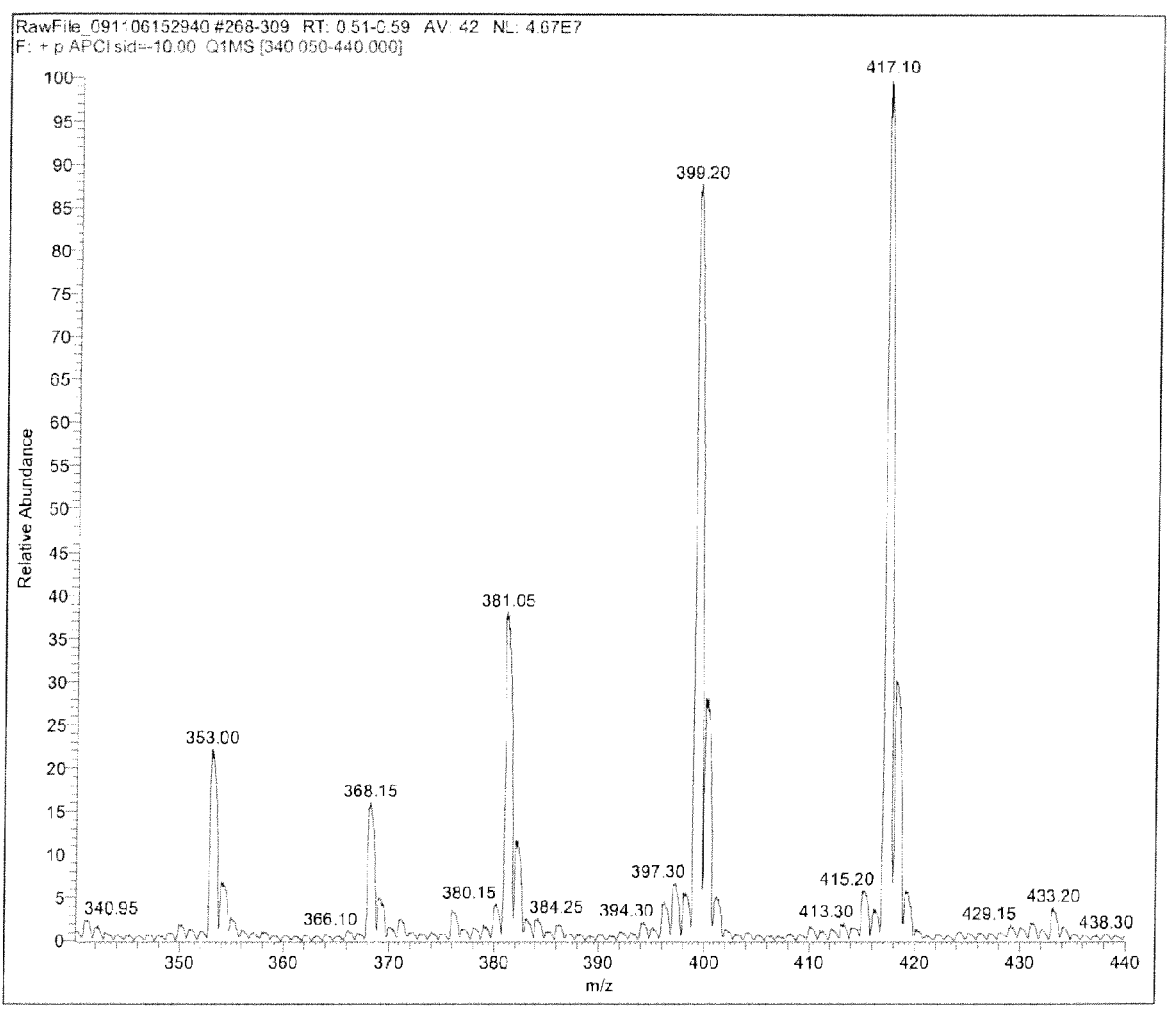
FIG. 2A shows an exemplary Q1 scan spectrum (covering the m/z range of about 340 to 440) for 1α,25-dihydroxyvitamin $D_2$-[26, 26, 26, 27, 27, 27]-$^2H_6$ ions.
Figure 2B:
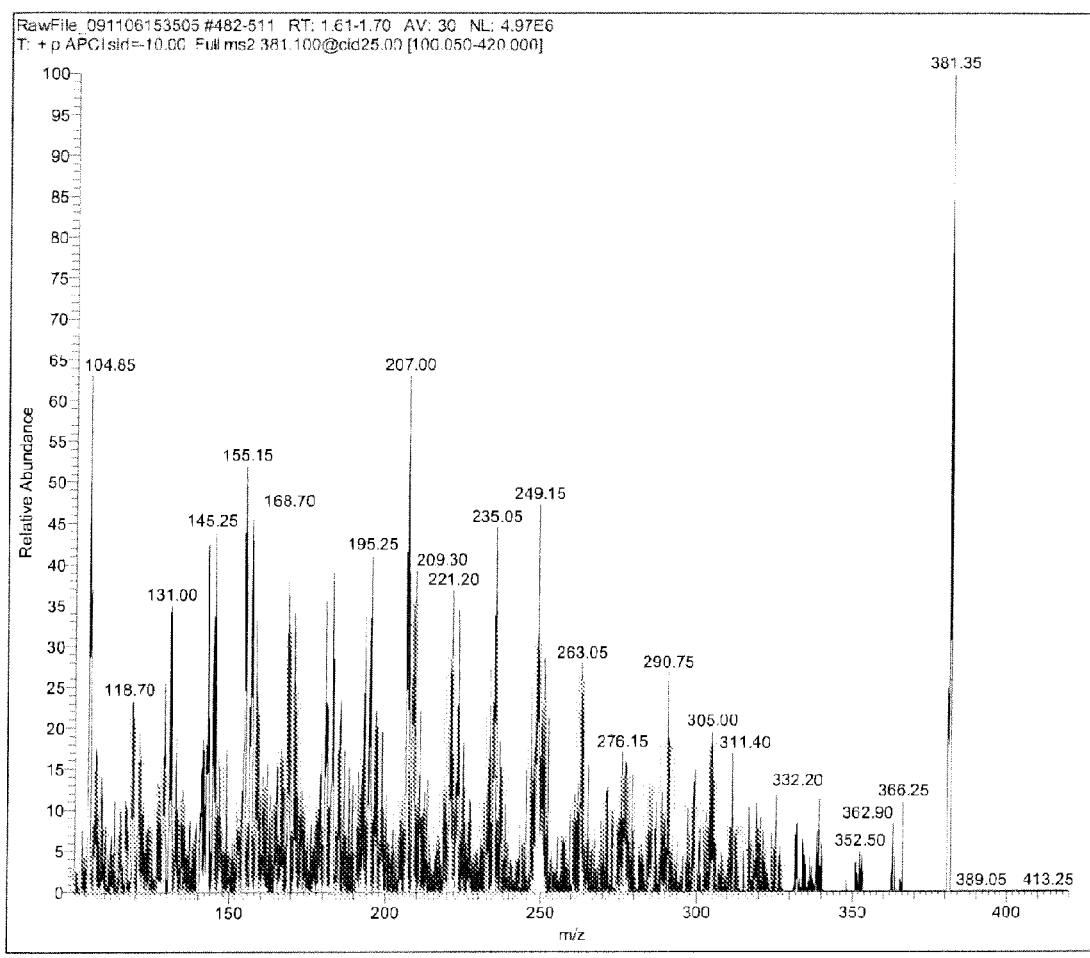
FIG. 2B shows an exemplary product ion spectra (covering the m/z range of about 100 to 420) for fragmentation of the 1α,25-dihydroxyvitamin $D_2$-[26, 26, 26, 27, 27, 27]-$^2H_6$ precursor ion with m/z of about 381.1.
Figure 2C:
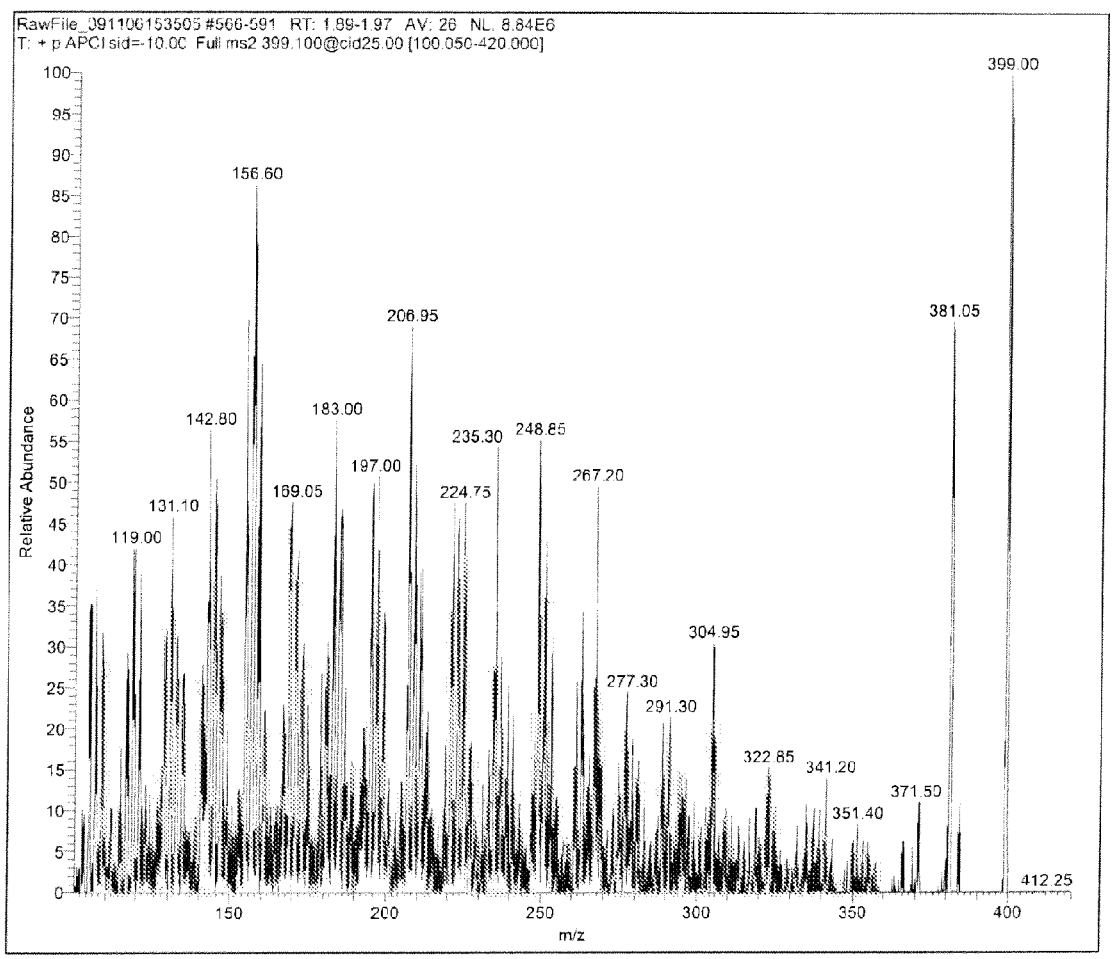
FIG. 2C shows an exemplary product ion spectra (covering the m/z range of about 250 to 350) for fragmentation of the 1α,25-dihydroxyvitamin $D_2$-[26, 26, 26, 27, 27, 27]-$^2H_6$ precursor ion with m/z of about 399.1.
Figure 2D:
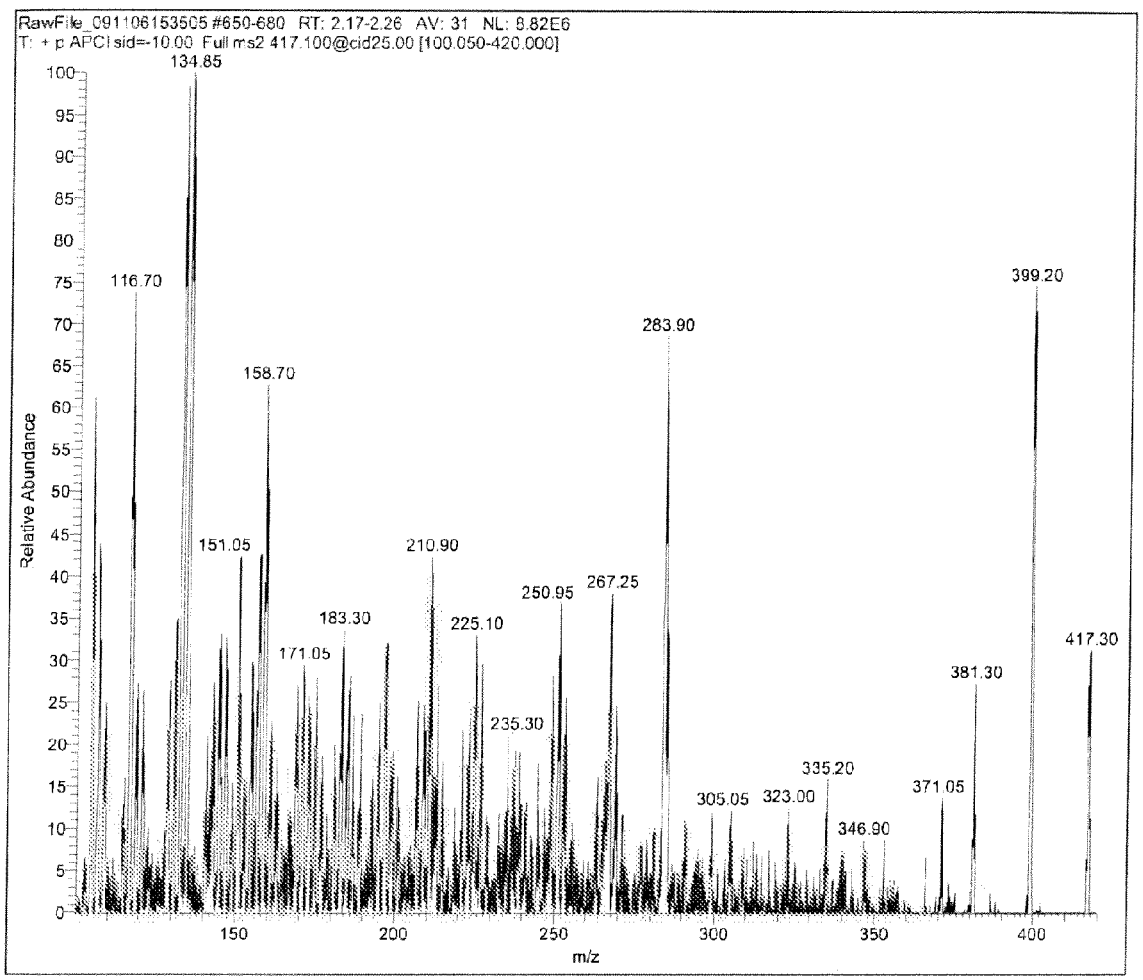
FIG. 2D shows an exemplary product ion spectra (covering the m/z range of about 250 to 350) for fragmentation of the 1α,25-dihydroxyvitamin $D_2$-[26, 26, 26, 27, 27, 27]-$^2H_6$ precursor ion with m/z of about 417.1. Details are described in Example 5.

Exemplary Spectra from LDTD-MS/MS Analysis of 1,25-dihydroxyvitamin $D_2$ and 1,25-dihydroxyvitamin $D_3$ Exemplary Q1 scan spectra from the analysis of samples containing 1α,25-dihydroxyvitamin $D_2$ and 1α,25-dihydroxyvitamin $D_2$-[26, 26, 26, 27, 27, 27]-$^2H_6$ are shown in FIGS. 1A, and 2A, respectively. These spectra were collected with LDTD-MS/MS according to Example 4 by scanning Q1 across a m/z range of about 350 to 450.

Exemplary product ion scans generated from three different precursor ions for each of 1α,25-dihydroxyvitamin $D_2$ and 1α,25-dihydroxyvitamin $D_2$-[26, 26, 26, 27, 27, 27]-$^2H_6$ are presented in FIGS. 1B-D, and 2B-D, respectively. The precursor ions selected in Q1 and the collision energies used to generate these product ion spectra are indicated in Table 4.

Exemplary MRM transitions for the quantitation of 1α,25-dihydroxyvitamin $D_2$ include fragmenting a precursor ion with a m/z of about 375.1 to a product ion with a m/z of about 105.3; fragmenting a precursor ion with a m/z of about 393.1 to a product ion with a m/z of about 156.9; and fragmenting a precursor ion with a m/z of about 411.1 to a product ion with a m/z of about 135.3. Exemplary MRM transitions for the quantitation of 1α,25-dihydroxyvitamin $D_2$-[26, 26, 26, 27, 27, 27]-$^2H_6$ include fragmenting a precursor ion with a m/z of about 381.1 to a product ion with a m/z of about 104.9; fragmenting a precursor ion with a m/z of about 399.1 to a product ion with a m/z of about 156.6; and fragmenting a precursor ion with a m/z of about 417.1 to a product ion with a m/z of about 134.9. However, as can be seen in the product ion scans in FIGS. 1B-D and 2B-D, several other product ions are generated upon fragmentation of the precursor ions. Additional product ions may be selected from those indicated in FIGS. 1B-D and 2B-D to replace or augment the exemplary fragment ions.

TABLE 4

Precursor Ions and Collision Cell Energies for Fragmentation of 1,25-dihydroxyvitamin $D_2$ and 1,25-dihydroxyvitamin $D_2$-[26,26,26,27,27,27]-$^2H_6$

| Analyte | Precursor Ion(s) (m/z) | Energy of Collision Cell (V) |
|---|---|---|
| 1α,25-dihydroxyvitamin $D_2$ | 375.1, 393.1, 411.1 | 25 |
| 1α,25-dihydroxyvitamin $D_2$-[26,26,26,27,27,27]-$^2H_6$ | 381.1, 399.1, 417.1 | 25 |

Figure 3A:
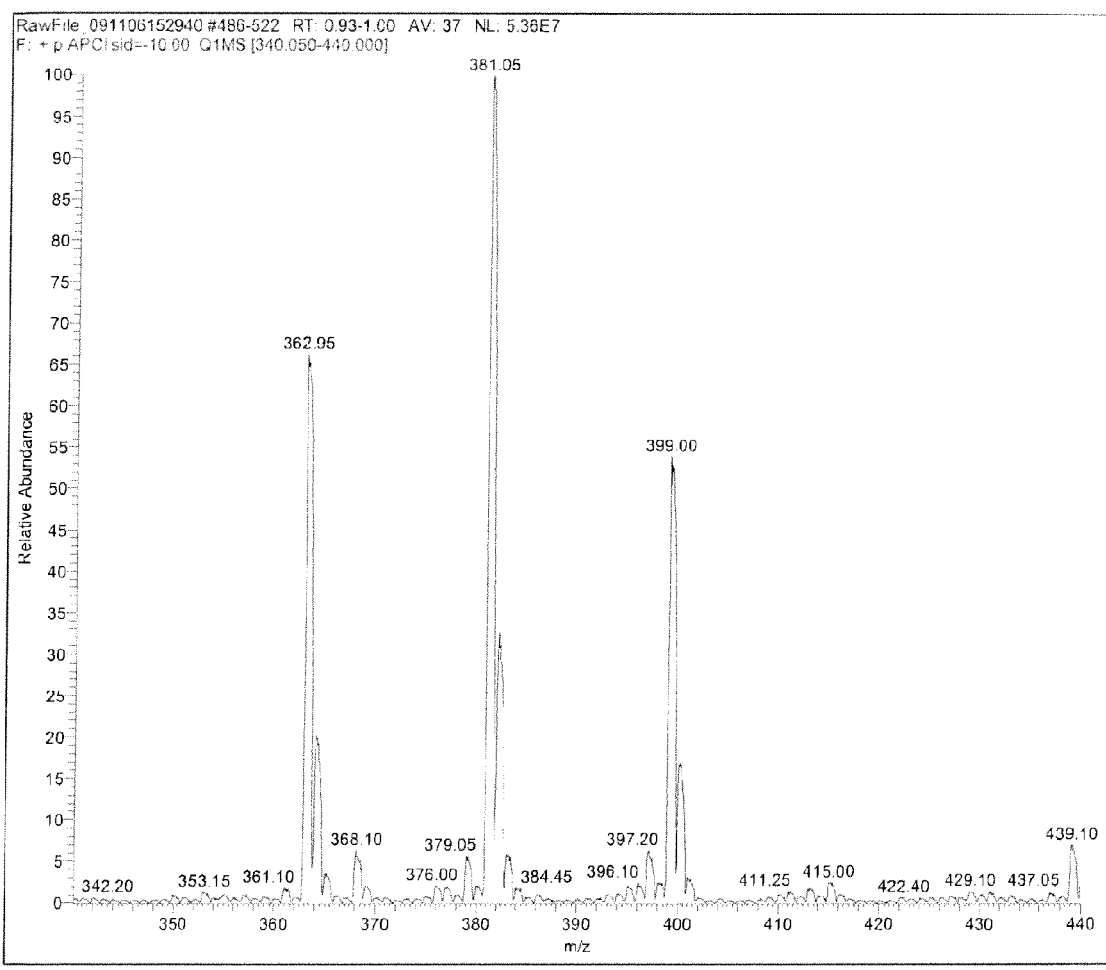
FIG. 3A shows an exemplary Q1 scan spectrum (covering the m/z range of about 340 to 440) for 1α,25-hydroxyvitamin $D_3$ ions.
Figure 3B:
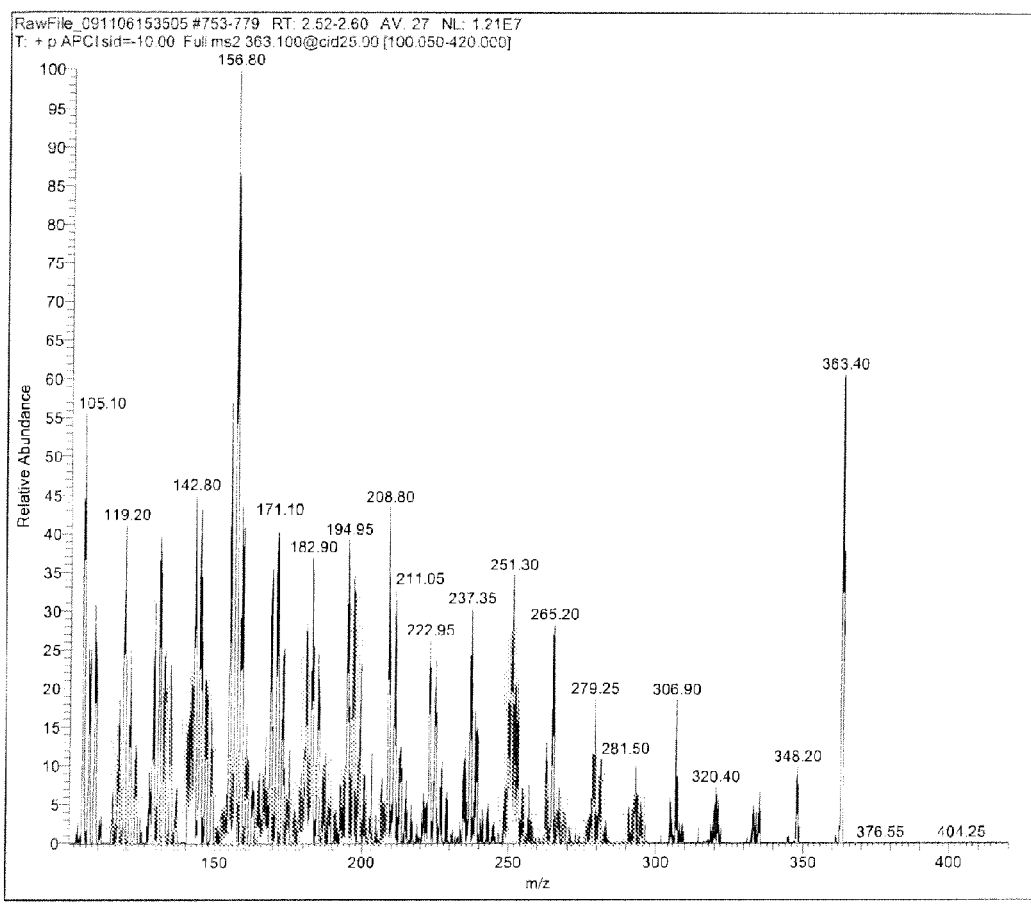
FIG. 3B shows an exemplary product ion spectra (covering the m/z range of about 100 to 420) for fragmentation of the 1α,25-dihydroxyvitamin $D_3$ precursor ion with m/z of about 363.1.
Figure 3C:
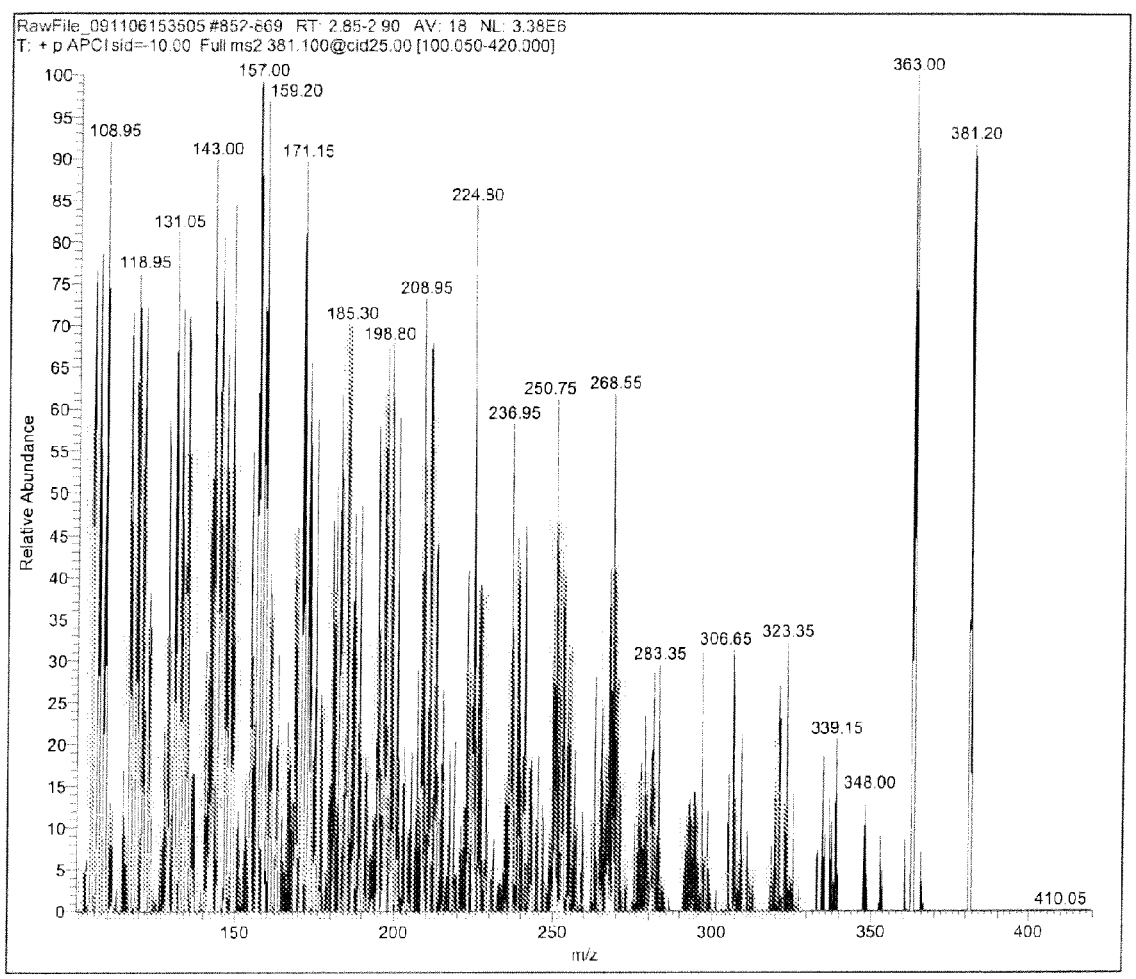
FIG. 3C shows an exemplary product ion spectra (covering the m/z range of about 100 to 420) for fragmentation of the 1α,25-dihydroxyvitamin $D_3$ precursor ion with m/z of about 381.1.
Figure 3D:
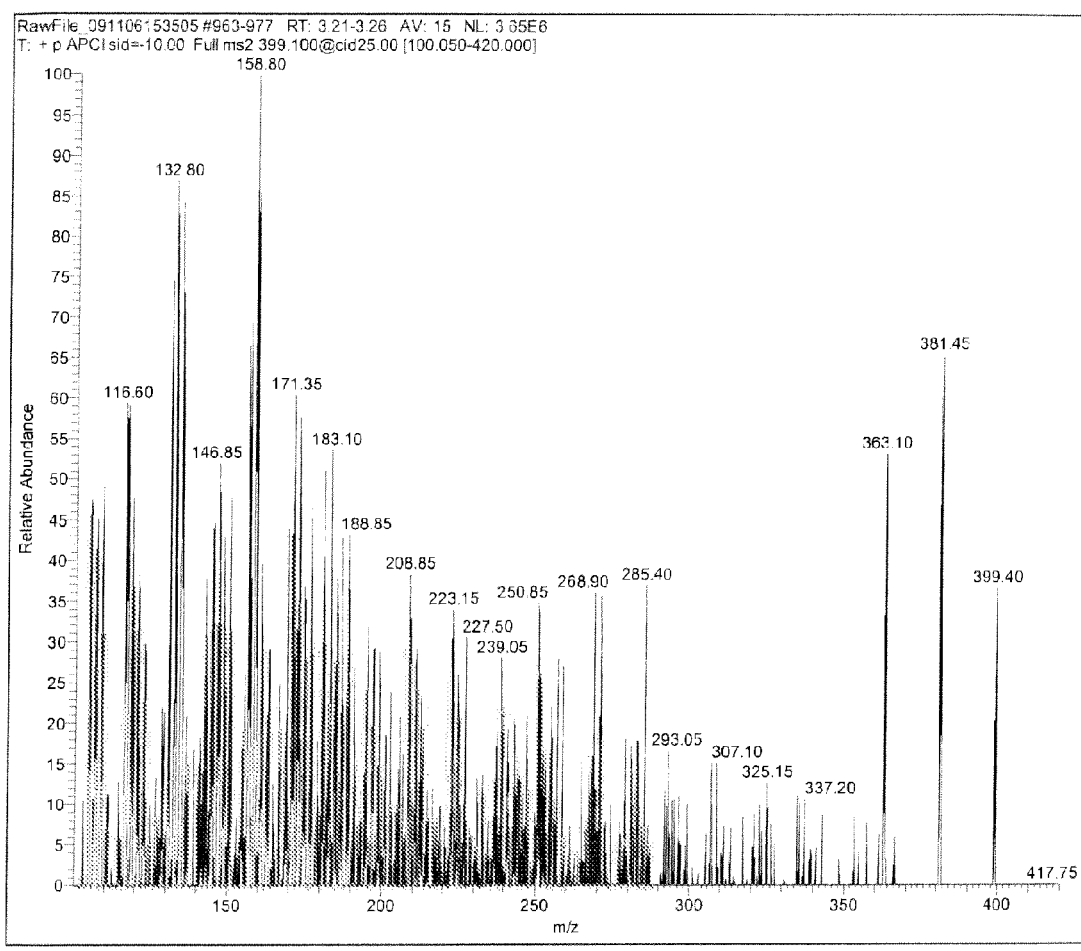
FIG. 3D shows an exemplary product ion spectra (covering the m/z range of about 100 to 420) for fragmentation of the 1α,25-dihydroxyvitamin $D_3$ precursor ion with m/z of about 399.1. Details are described in Example 5.
Figure 4A:
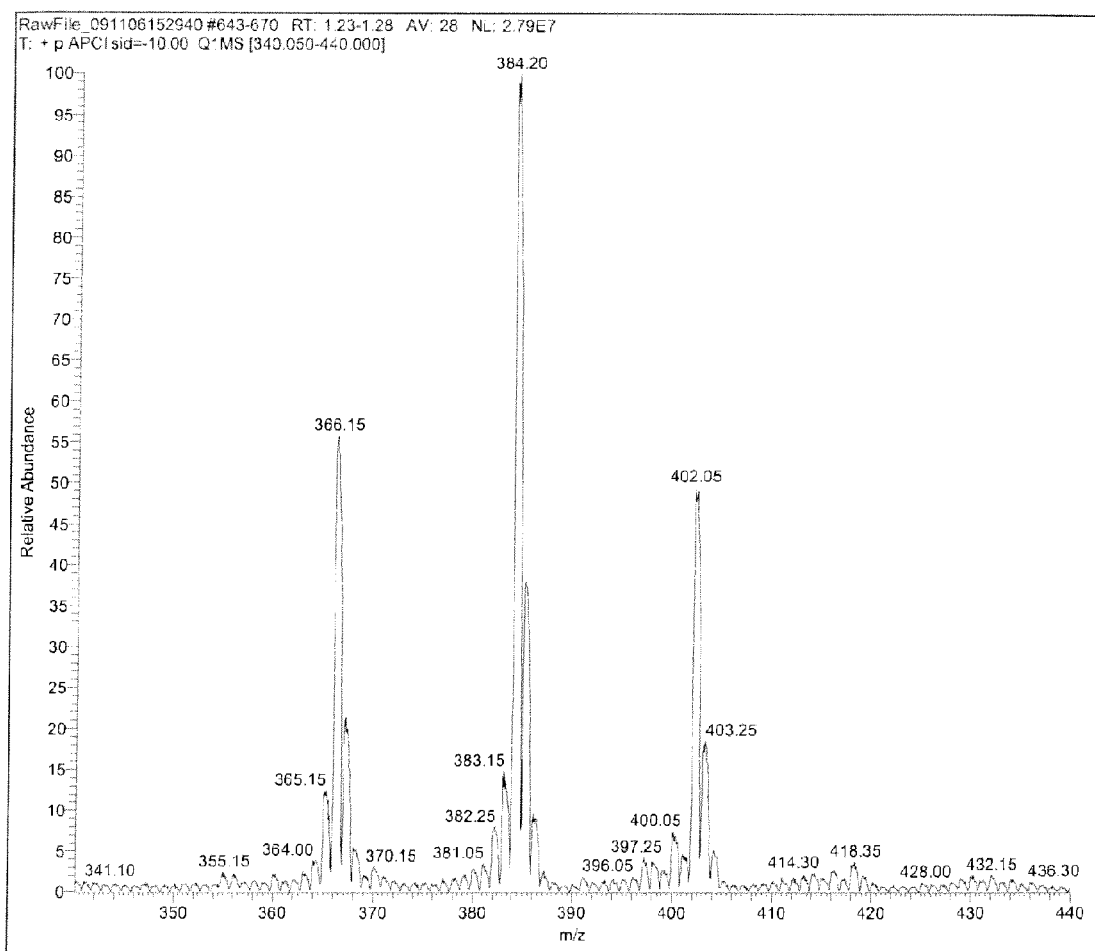
FIG. 4A shows an exemplary Q1 scan spectrum (covering the m/z range of about 340 to 440) for 1α,25-dihydroxyvitamin $D_3$-[6, 19, 19]-$^2H_3$ ions.
Figure 4B:
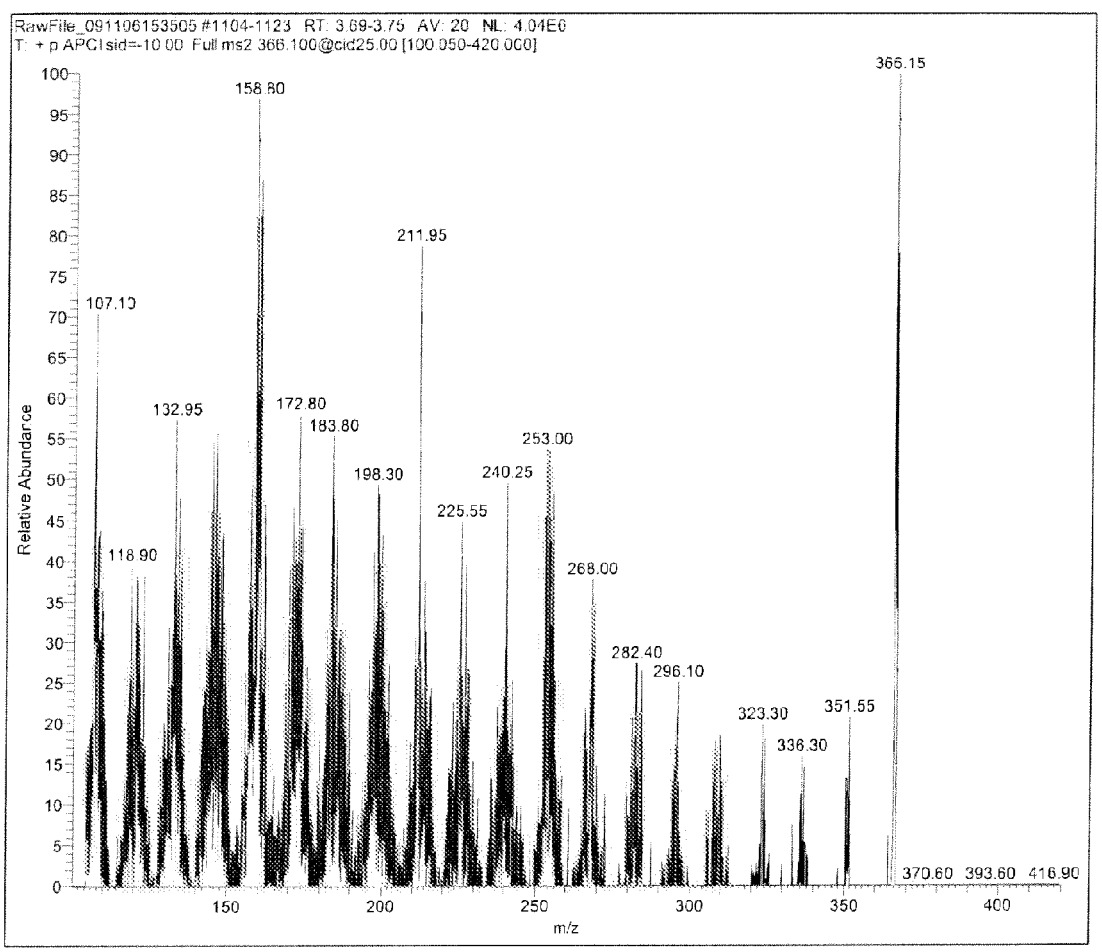
FIG. 4B shows an exemplary product ion spectra (covering the m/z range of about 100 to 420) for fragmentation of the 1α,25-dihydroxyvitamin $D_3$-[6, 19, 19]-$^2H_3$ precursor ion with m/z of about 366.1.
Figure 4C:
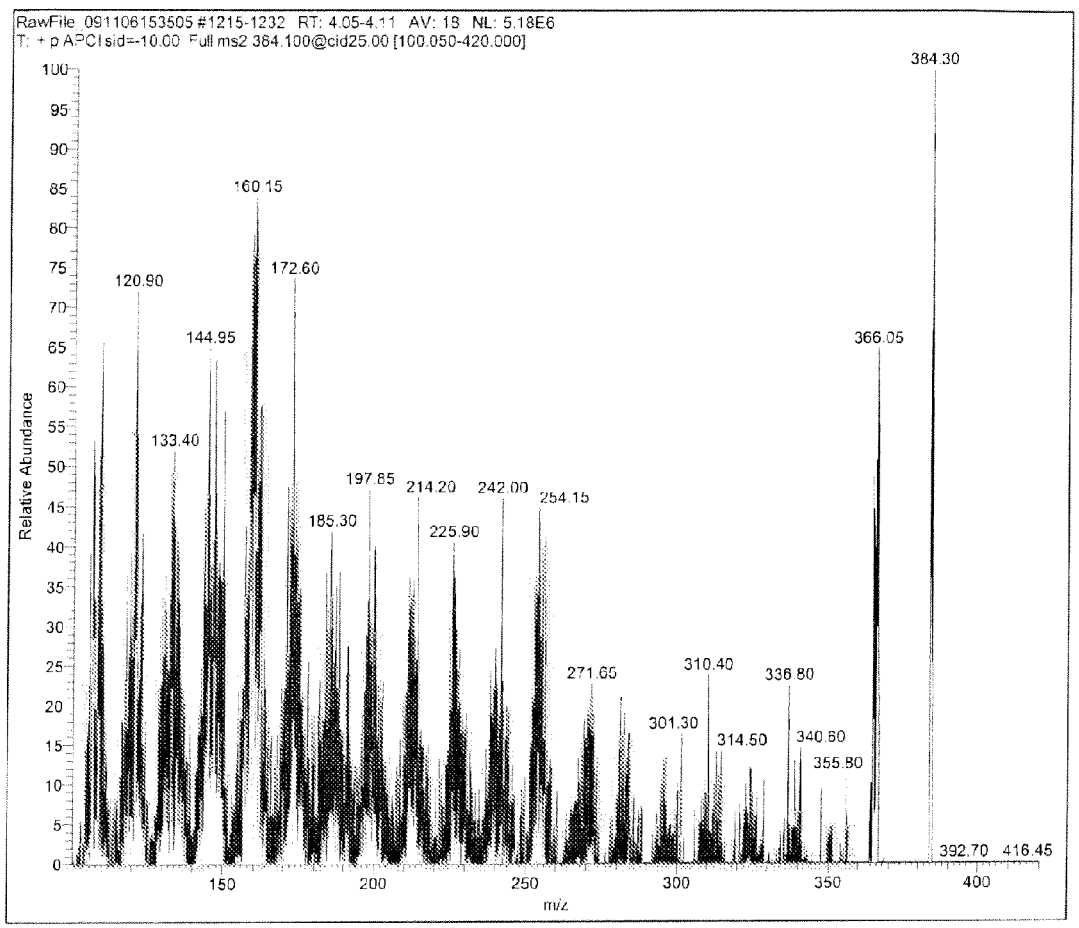
FIG. 4C shows an exemplary product ion spectra (covering the m/z range of about 100 to 420) for fragmentation of the 1α,25-dihydroxyvitamin $D_3$-[6, 19, 19]-$^2H_3$ precursor ion with m/z of about 384.1.
Figure 4D:
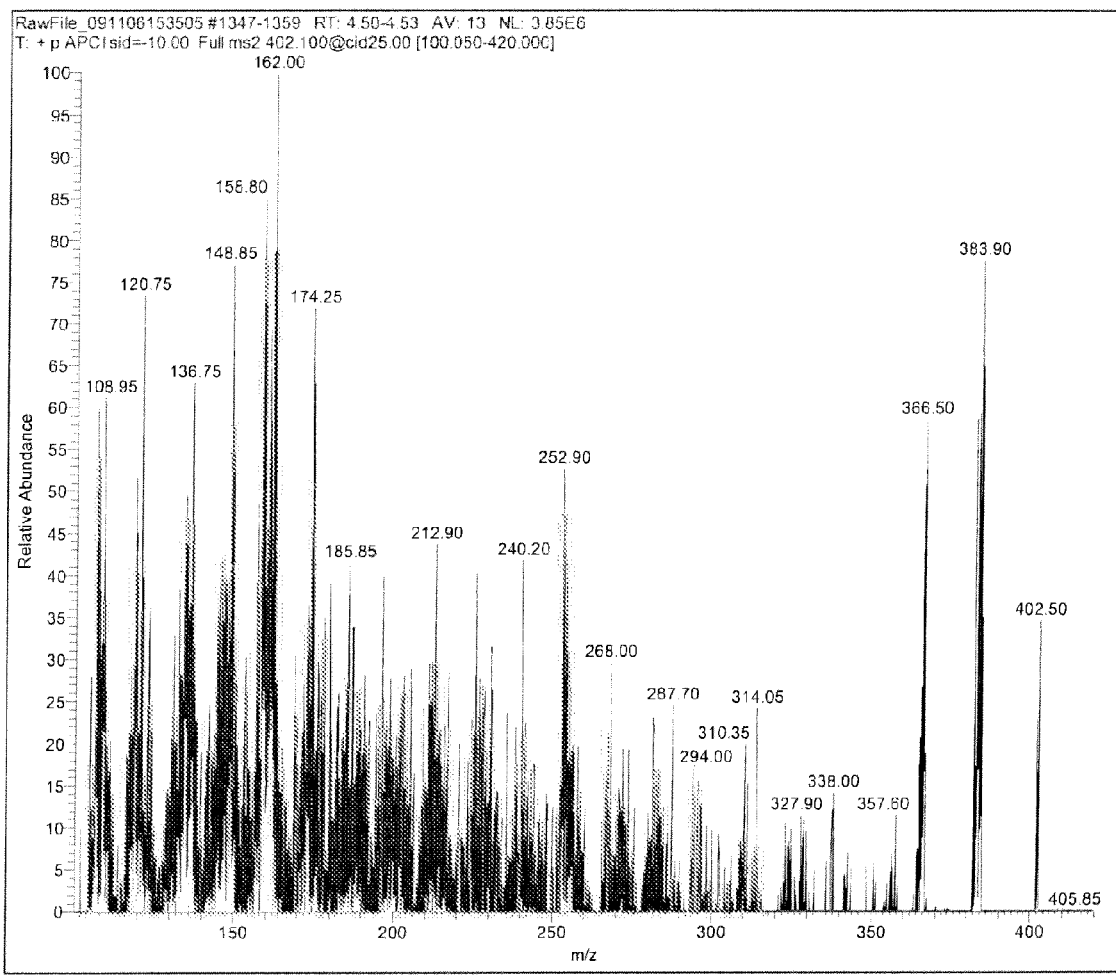
FIG. 4D shows an exemplary product ion spectra (covering the m/z range of about 100 to 420) for fragmentation of the 1α,25-dihydroxyvitamin $D_3$-[6, 19, 19]-$^2H_3$ precursor ion with m/z of about 402.1. Details are described in Example 5.
Figure 5A:
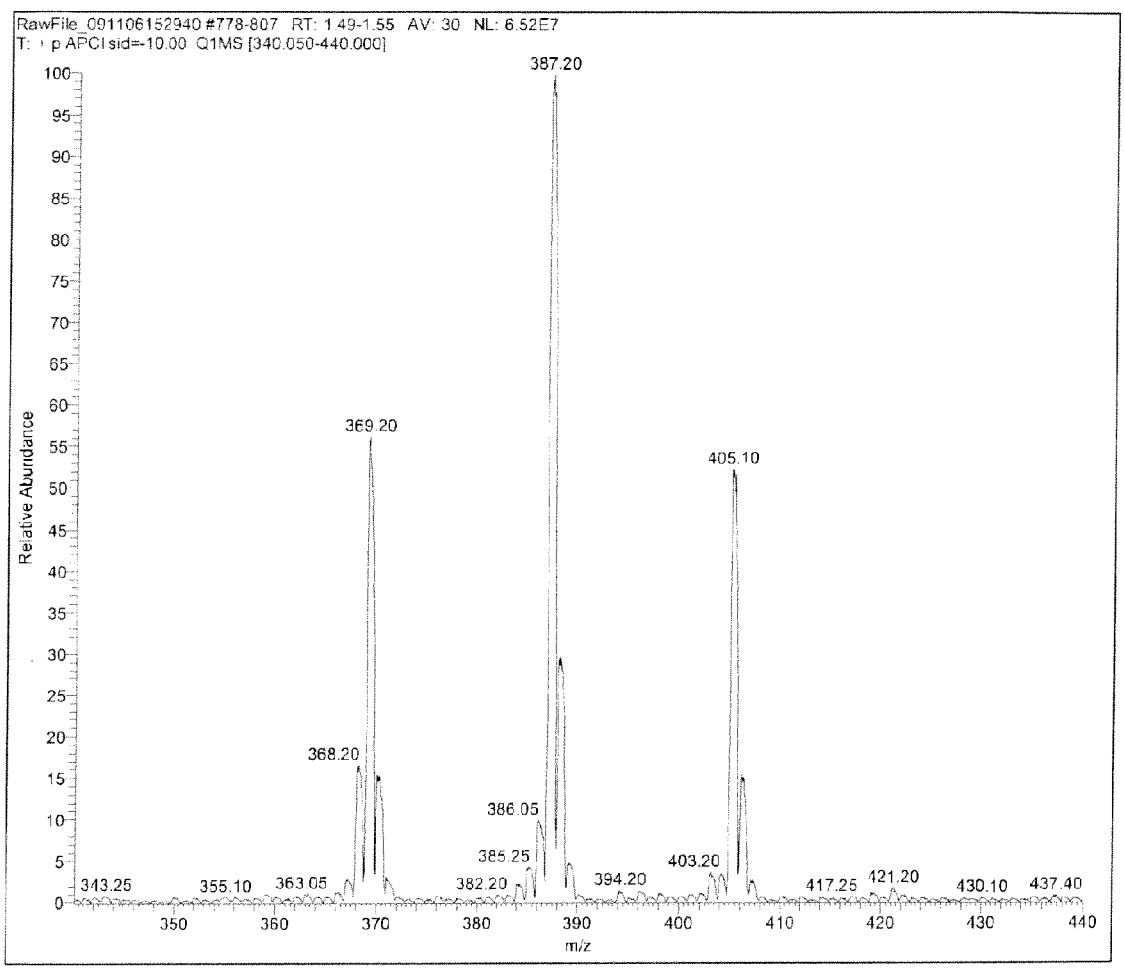
FIG. 5A shows an exemplary Q1 scan spectrum (covering the m/z range of about 340 to 440) for 1α,25-dihydroxyvitamin $D_3$-[26, 26, 26, 27, 27, 27]-$^2H_6$ ions.
Figure 5B:
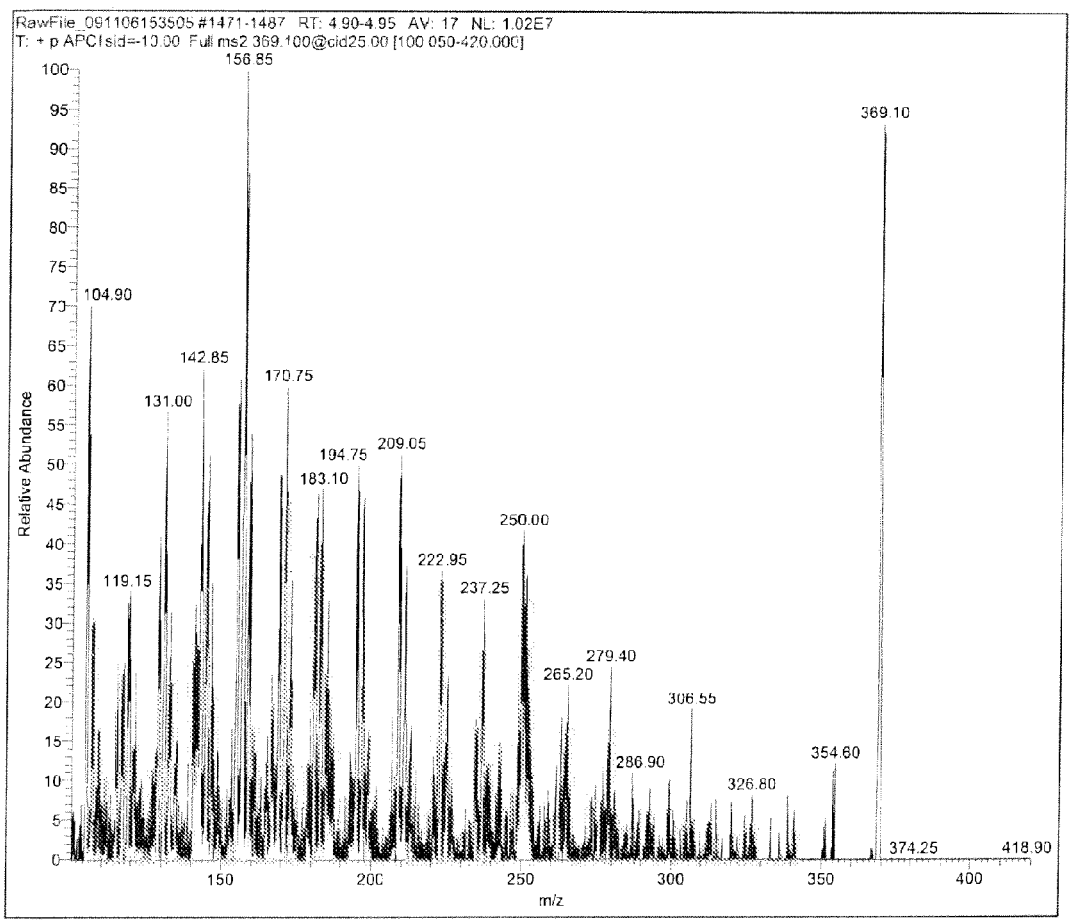
FIG. 5B shows an exemplary product ion spectra (covering the m/z range of about 100 to 420) for fragmentation of the 1α,25-dihydroxyvitamin $D_3$-[26, 26, 26, 27, 27, 27]-$^2H_6$ precursor ion with m/z of about 369.1.
Figure 5C:
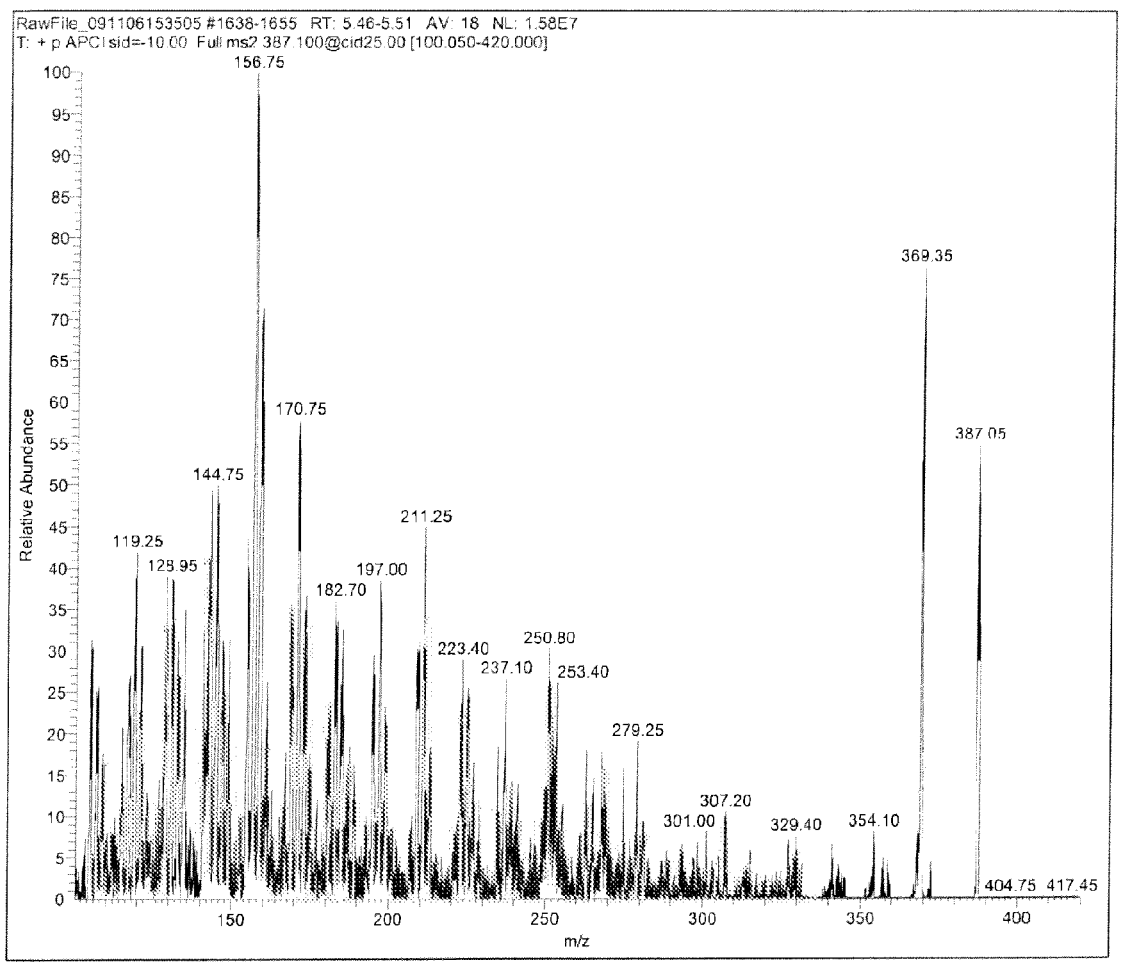
FIG. 5C shows an exemplary product ion spectra (covering the m/z range of about 250 to 350) for fragmentation of the 1α,25-dihydroxyvitamin $D_3$-[26, 26, 26, 27, 27, 27]-$^2H_6$ precursor ion with m/z of about 387.1.
Figure 5D:
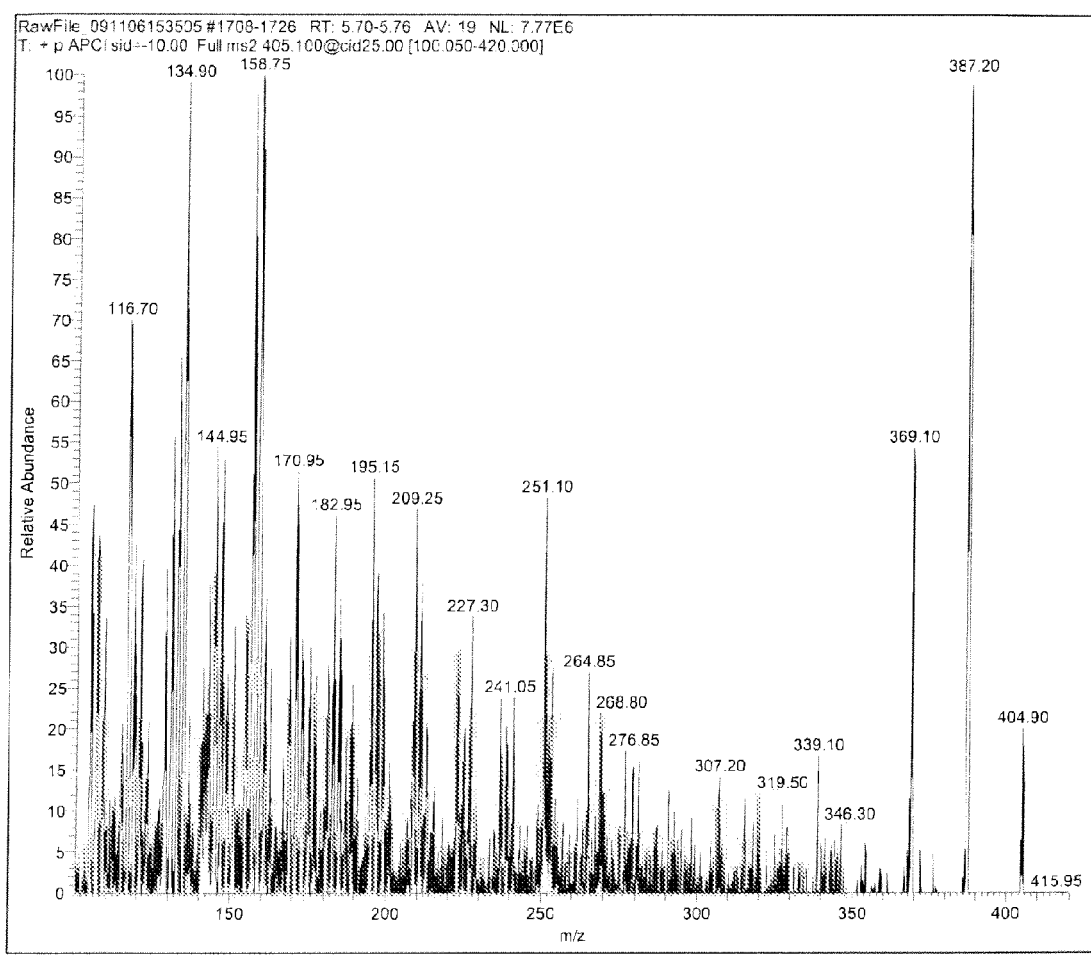
FIG. 5D shows an exemplary product ion spectra (covering the m/z range of about 250 to 350) for fragmentation of the 1α,25-dihydroxyvitamin $D_3$-[26, 26, 26, 27, 27, 27]-$^2H_6$ precursor ion with m/z of about 405.1. Details are described in Example 5.

Exemplary Q1 scan spectra from the analysis of 1α,25-dihydroxyvitamin $D_3$, 1α,25-dihydroxyvitamin $D_3$-[6, 19, 19]-$^2H_3$, and 1,25-dihydroxyvitamin $D_3$-[26, 26, 26, 27, 27, 27]-$^2H_6$ are shown in FIGS. 3A, 4A, and 5A, respectively. These spectra were collected with LDTD-MS/MS according to Example 4 by scanning Q1 across a m/z range of about 340 to 440.

Exemplary product ion scans generated from three different precursor ions for each of 1α,25-dihydroxyvitamin $D_3$, 1α,25-dihydroxyvitamin $D_3$-[6, 19, 19]-$^2H_3$, and 1α,25-dihydroxyvitamin $D_3$-[26, 26, 26, 27, 27, 27]-$^2H_6$ are presented in FIGS. 3B-D, 4B-D, and 5B-D, respectively. The precursor ions selected in Q1 and the collision energies used to generate these product ion spectra are indicated in Table 5.

Exemplary MRM transitions for the quantitation of 1α,25-dihydroxyvitamin $D_3$ include fragmenting a precursor ion with a m/z of about 363.1 to a product ion with a m/z of about 156.8; fragmenting a precursor ion with a m/z of about 381.1 to a product ion with a m/z of about 157.0; and fragmenting a precursor ion with a m/z of about 399.1 to a product ion with a m/z of about 158.8. Exemplary MRM transitions for the quantitation of 1α,25-dihydroxyvitamin $D_3$-[6, 19, 19]-$^2H_3$ include fragmenting a precursor ion with a m/z of about 366.1 to a product ion with a m/z of about 158.8; fragmenting a precursor ion with a m/z of about 384.1 to a product ion with a m/z of about 160.2; and fragmenting a precursor ion with a m/z of about 402.1 to a product ion with a m/z of about 162.0. Exemplary MRM transitions for the quantitation of 1α,25-dihydroxyvitamin $D_3$-[26, 26, 26, 27, 27, 27]-$^2H_6$ include fragmenting a precursor ion with a m/z of about 369.1 to a product ion with a m/z of about 156.9.9; fragmenting a precursor ion with a m/z of about 387.1 to a product ion with a m/z of about 156.8; and fragmenting a precursor ion with a m/z of about 405.1 to a product ion with a m/z of about 158.8. However, as can be seen in the product ion scans in FIGS. 3B-D, 4B-D, and 5B-D, several other product ions are generated upon fragmentation of the precursor ions. Additional product ions may be selected from those indicated in FIGS. 3B-D, 4B-D, and 5B-D to replace or augment the exemplary fragment ions.

TABLE 5

Precursor Ions and Collision Cell Energies for Fragmentation of 1α,25-dihydroxyvitamin $D_3$, 1α,25-dihydroxyvitamin $D_3$-[6,19,19]-$^2H_3$, and 1α,25-dihydroxyvitamin $D_3$-[26,26,26,27,27,27]-$^2H_6$

| Analyte | Precursor Ion (m/z) | Energy of Collision Cell (V) |
|---|---|---|
| 1α,25-dihydroxyvitamin $D_3$ | 363,1, 381.1. 399.1 | 25 |
| 1α,25-dihydroxyvitamin $D_3$-[6,19,19]-$^2H_3$ | 366.1, 384.1. 402.1 | 25 |
| 1α,25-dihydroxyvitamin $D_3$-[26,26,26,27,27,27]-$^2H_6$ | 369.1, 387.1. 405.1 | 25 |

Example 6

Exemplary Spectra from LDTD-MS/MS Analysis of PTAD Derivatized 1α,25-dihydroxyvitamin $D_2$ and 1α,25-dihydroxyvitamin $D_3$ PTAD derivatives of 1α,25-dihydroxyvitamin $D_2$, 1α,25-dihydroxyvitamin $D_2$-[26, 26, 26, 27, 27, 27]-$^2H_6$, 1α,25-dihydroxyvitamin $D_3$, 1α,25-dihydroxyvitamin $D_3$-[6, 19, 19]-$^2H_3$, and 1α,25-dihydroxyvitamin $D_3$-[26, 26, 26, 27, 27, 27]-$^2H_6$ were prepared by treating aliquots of stock solutions of each analyte with PTAD in acetonitrile. The derivatization reactions was allowed to proceed for approximately one hour, and were quenched by adding water to the reaction mixture. The derivatized analytes were then analyzed according to the procedure outlined above in Examples 3 and 4.

Figure 6A:
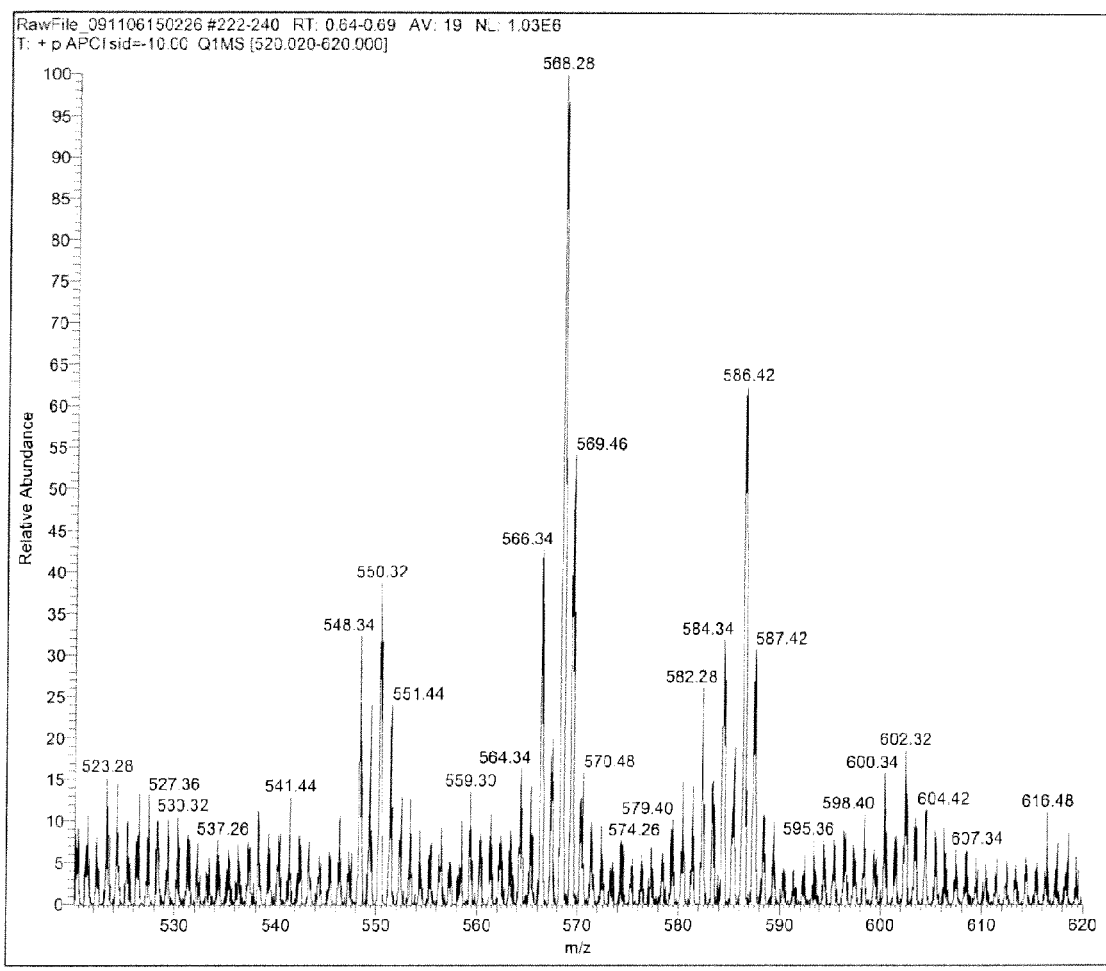
FIG. 6A shows an exemplary Q1 scan spectrum (covering the m/z range of about 520 to 620) for PTAD-1α,25-dihydroxyvitamin $D_2$ ions.
Figure 6B:
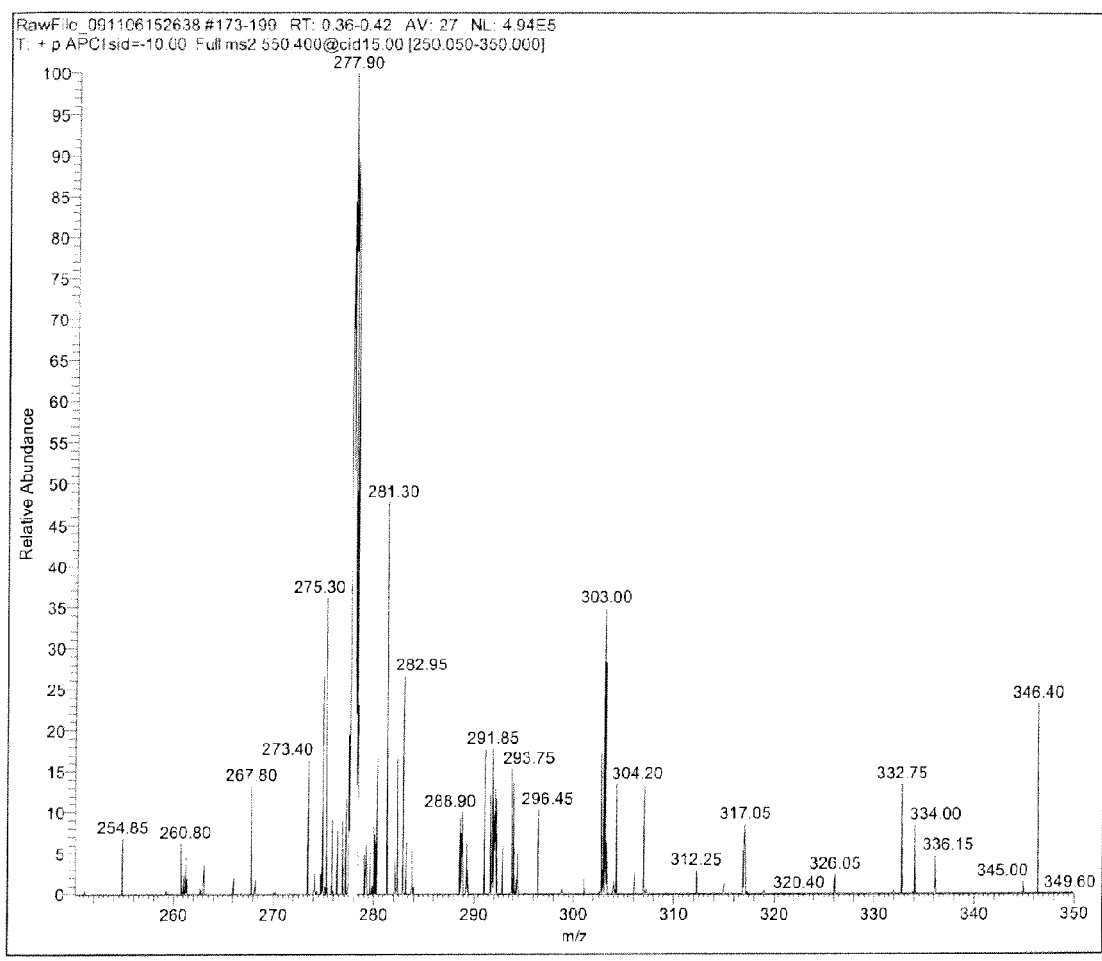
FIG. 6B shows an exemplary product ion spectra (covering the m/z range of about 250 to 350) for fragmentation of the PTAD-1α,25-dihydroxyvitamin $D_2$ precursor ion with m/z of about 550.4.
Figure 6C:
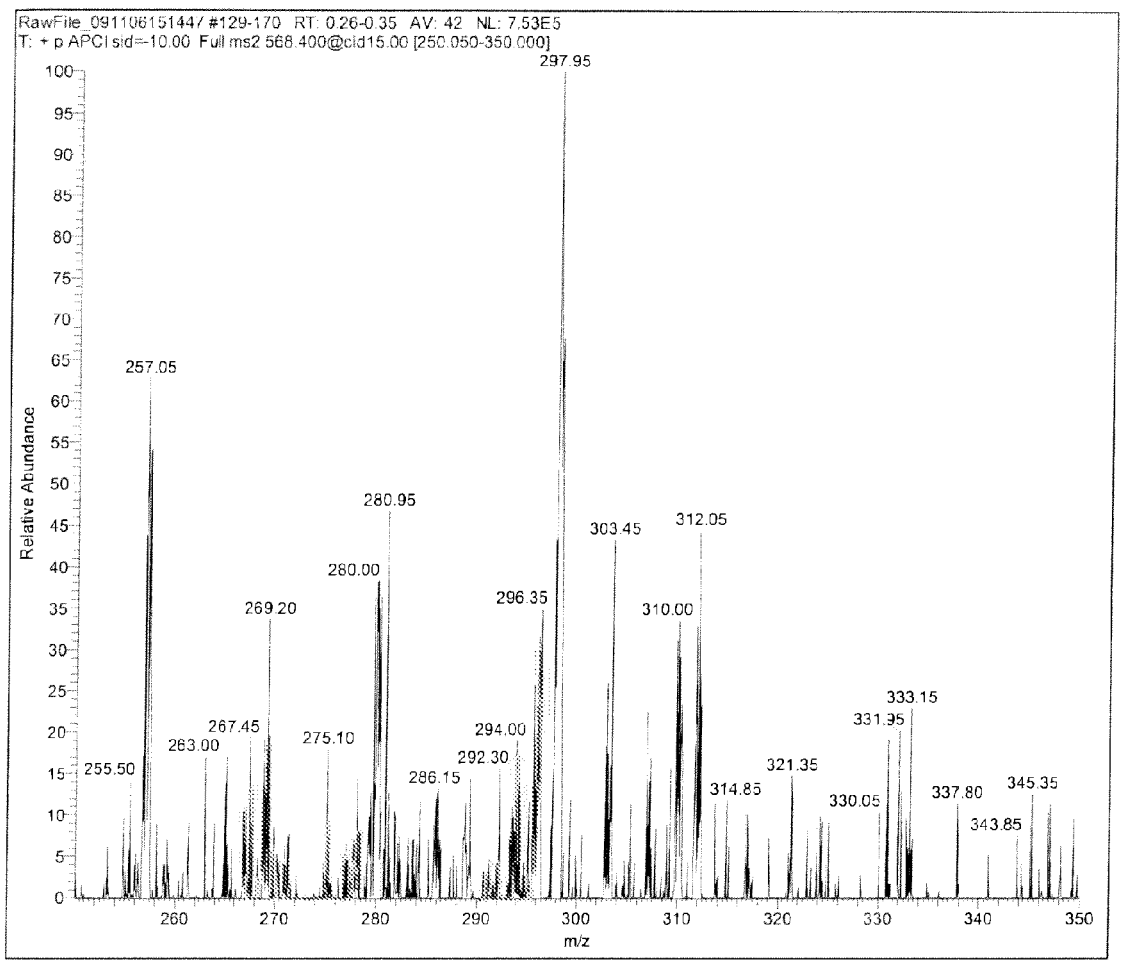
FIG. 6C shows an exemplary product ion spectra (covering the m/z range of about 250 to 350) for fragmentation of the PTAD-1α,25-dihydroxyvitamin $D_2$ precursor ion with m/z of about 568.4.
Figure 6D:
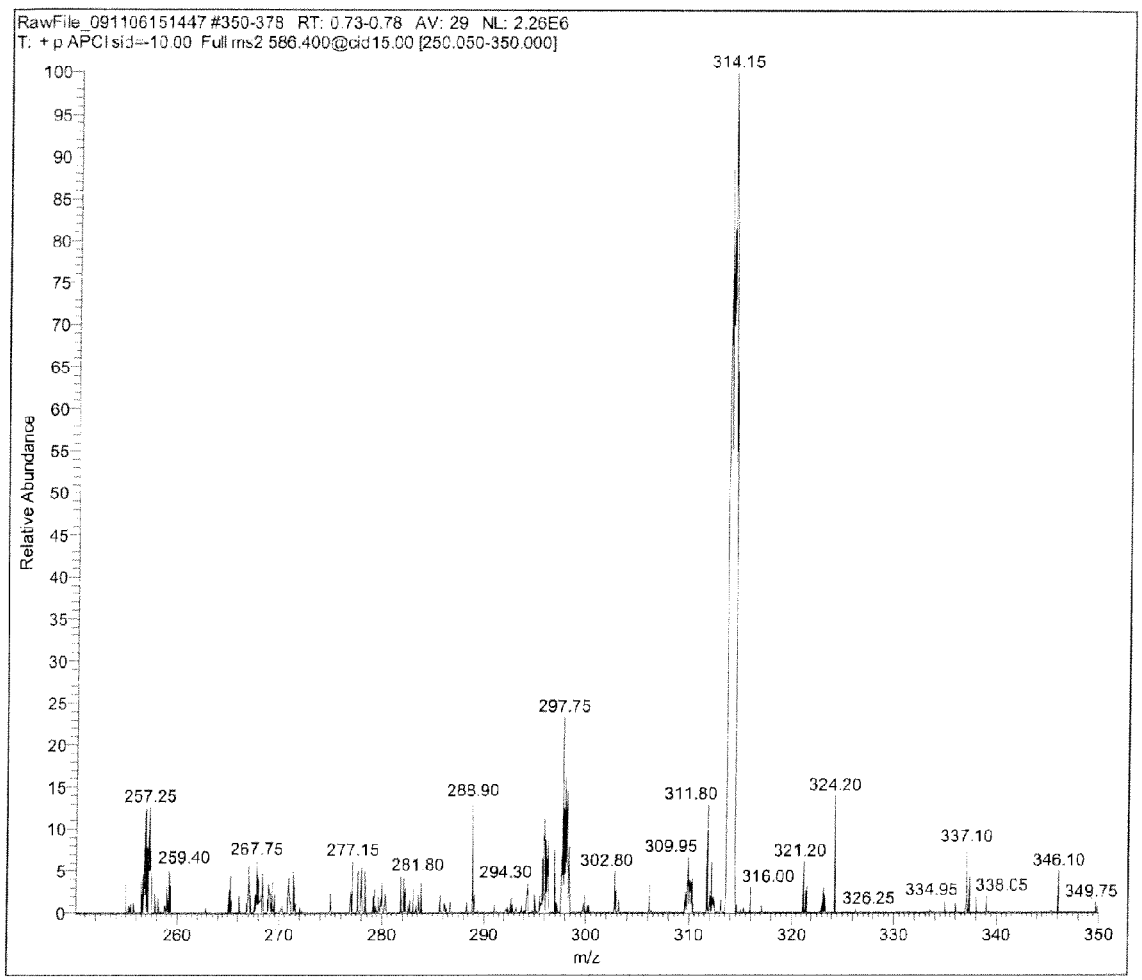
FIG. 6D shows an exemplary product ion spectra (covering the m/z range of about 250 to 350) for fragmentation of the PTAD-1α,25-dihydroxyvitamin $D_2$ precursor ion with m/z of about 586.4. Details are described in Example 6.
Figure 7A:
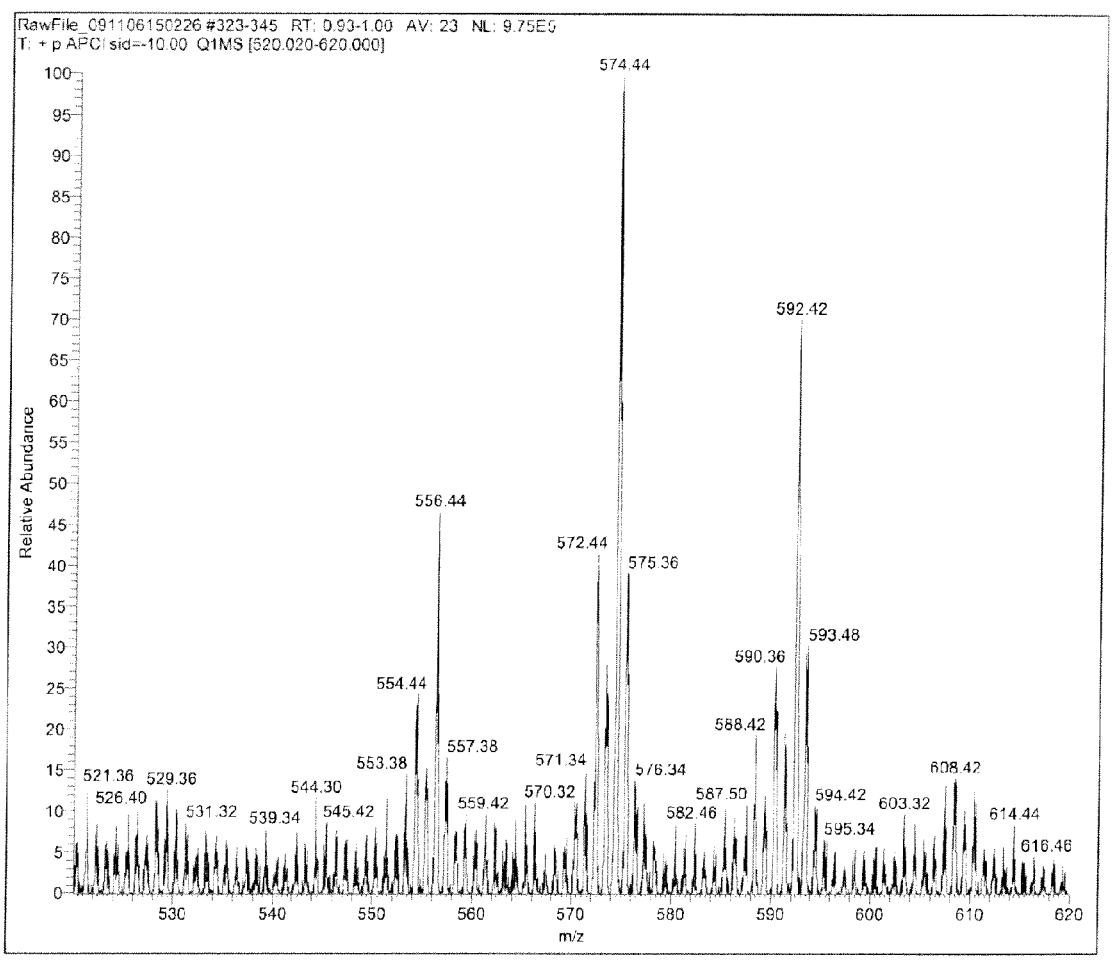
FIG. 7A shows an exemplary Q1 scan spectrum (covering the m/z range of about 520 to 620) for PTAD-1α,25-dihydroxyvitamin $D_2$-[26, 26, 26, 27, 27, 27]-$^2H_6$ ions.
Figure 7B:
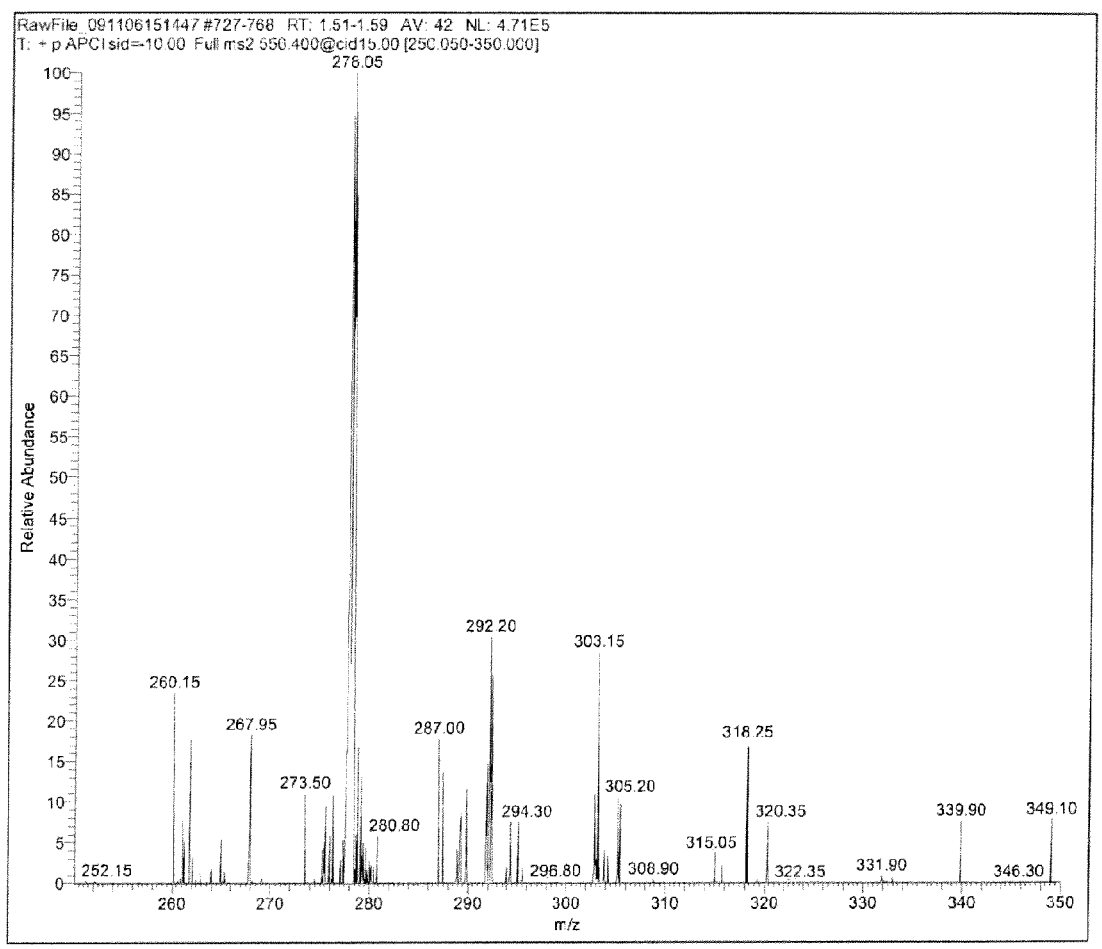
FIG. 7B shows an exemplary product ion spectra (covering the m/z range of about 250 to 350) for fragmentation of the PTAD-1α,25-dihydroxyvitamin $D_2$-[26, 26, 26, 27, 27, 27]-$^2H_6$ precursor ion with m/z of about 556.4.
Figure 7C:
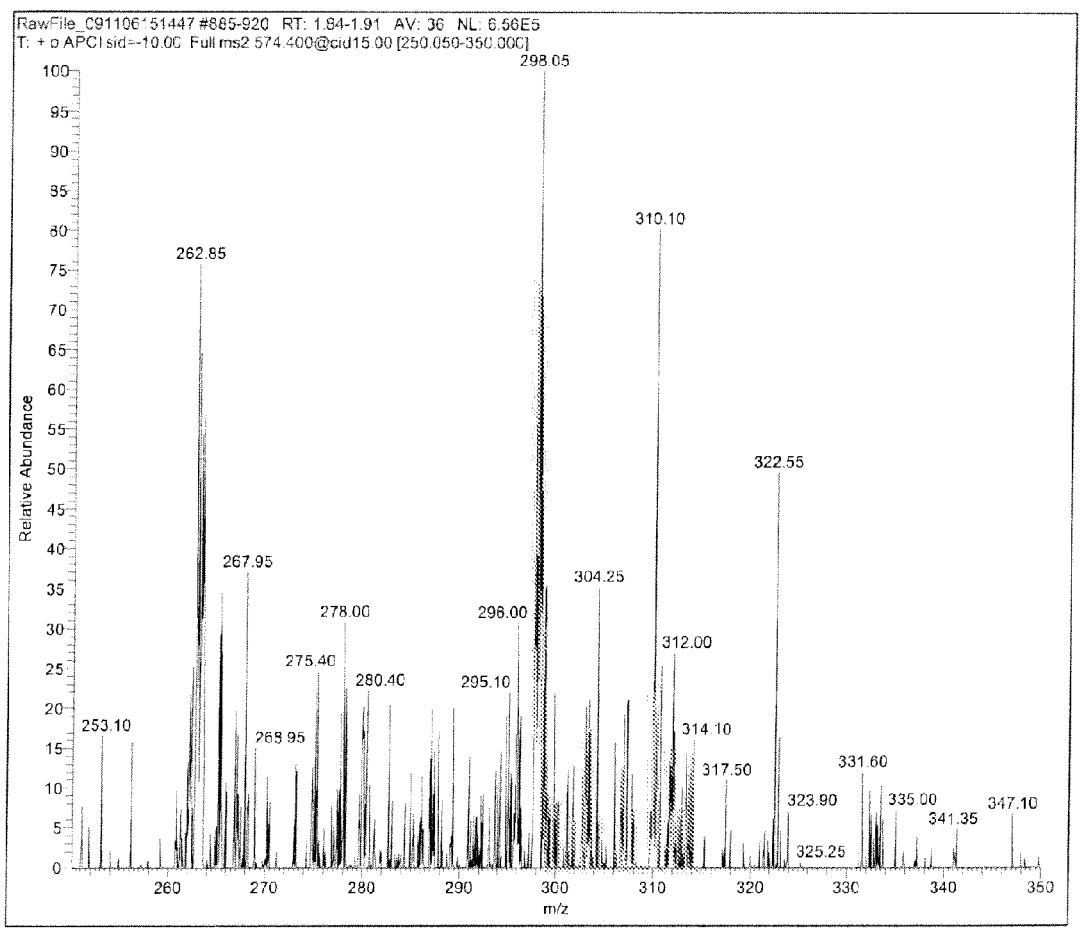
FIG. 7C shows an exemplary product ion spectra (covering the m/z range of about 250 to 350) for fragmentation of the PTAD-1α,25-dihydroxyvitamin $D_2$-[26, 26, 26, 27, 27, 27]-$^2H_6$ precursor ion with m/z of about 574.4
Figure 7D:
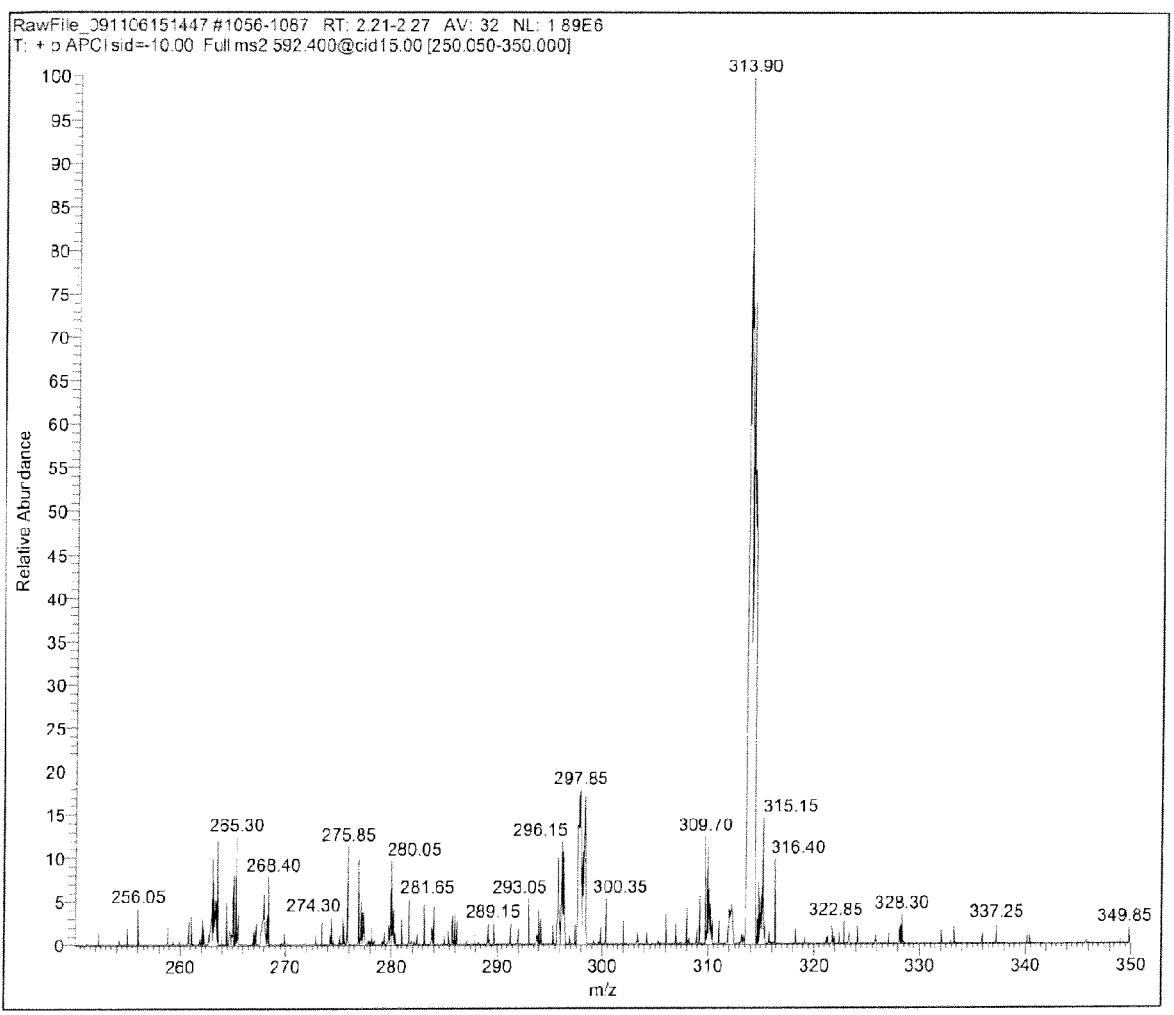
FIG. 7D shows an exemplary product ion spectra (covering the m/z range of about 250 to 350) for fragmentation of the PTAD-1α,25-dihydroxyvitamin $D_2$-[26, 26, 26, 27, 27, 27]-$^2H_6$ precursor ion with m/z of about 592.4. Details are described in Example 6.

Exemplary Q1 scan spectra from the analysis of samples containing PTAD-1α,25-dihydroxyvitamin $D_2$ and PTAD-1α,25-dihydroxyvitamin $D_2$-[26, 26, 26, 27, 27, 27]-$^2H_6$ are shown in FIGS. 6A, and 7A, respectively. These spectra were collected with LDTD-MS/MS according to Example 4 by scanning Q1 across a m/z range of about 520 to 620.

Exemplary product ion scans generated from three different precursor ions for each of PTAD-1α,25-dihydroxyvitamin $D_2$ and PTAD-1α,25-dihydroxyvitamin $D_2$-[26, 26, 26, 27, 27, 27]-$^2H_6$ are presented in FIGS. 6B-D, and 7B-D, respectively. The precursor ions selected in Q1 and the collision energies used to generate these product ion spectra are indicated in Table 6.

Exemplary MRM transitions for the quantitation of PTAD-125-dihydroxyvitamin D/include fragmenting a precursor ion with a m/z of about 550.4 to a product ion with a m/z of about 277.9; fragmenting a precursor ion with a m/z of about 568.4 to a product ion with a m/z of about 298.0; and fragmenting a precursor ion with a m/z of about 586.4 to a product ion with a m/z of about 314.2. Exemplary MRM transitions for the quantitation of PTAD-1α,25-dihydroxyvitamin $D_2$-[26, 26, 26, 27, 27, 27]-$^2H_6$ include fragmenting a precursor ion with a m/z of about 556.4 to a product ion with a m/z of about 278.1; fragmenting a precursor ion with a m/z of about 574.4 to a product ion with a m/z of about 298.1; and fragmenting a precursor ion with a m/z of about 592.4 to a product ion with a m/z of about 313.9. However, as can be seen in the product ion scans in FIGS. 6B-D and 7B-D, several other product ions are generated upon fragmentation of the precursor ions. Additional product ions may be selected from those indicated in FIGS. 6B-D and 7B-D to replace or augment the exemplary fragment ions.

TABLE 6

Precursor Ions and Collision Cell Energies for Fragmentation of PTAD-1α,25-dihydroxyvitamin $D_2$ and PTAD-1α,25-dihydroxyvitamin $D_2$-[26,26,26,27,27,27]-$^2H_6$

| Analyte | Precursor Ion (m/z) | Energy of Collision Cell (V) |
|---|---|---|
| PTAD-1α,25-dihydroxyvitamin $D_2$ | 550.4, 568.4, 586.4 | 15 |
| PTAD-1α,25-dihydroxyvitamin $D_2$-[26,26,26,27,27,27]-$^2H_6$ | 556.3, 574.4, 592.4 | 15 |

Figure 8A:
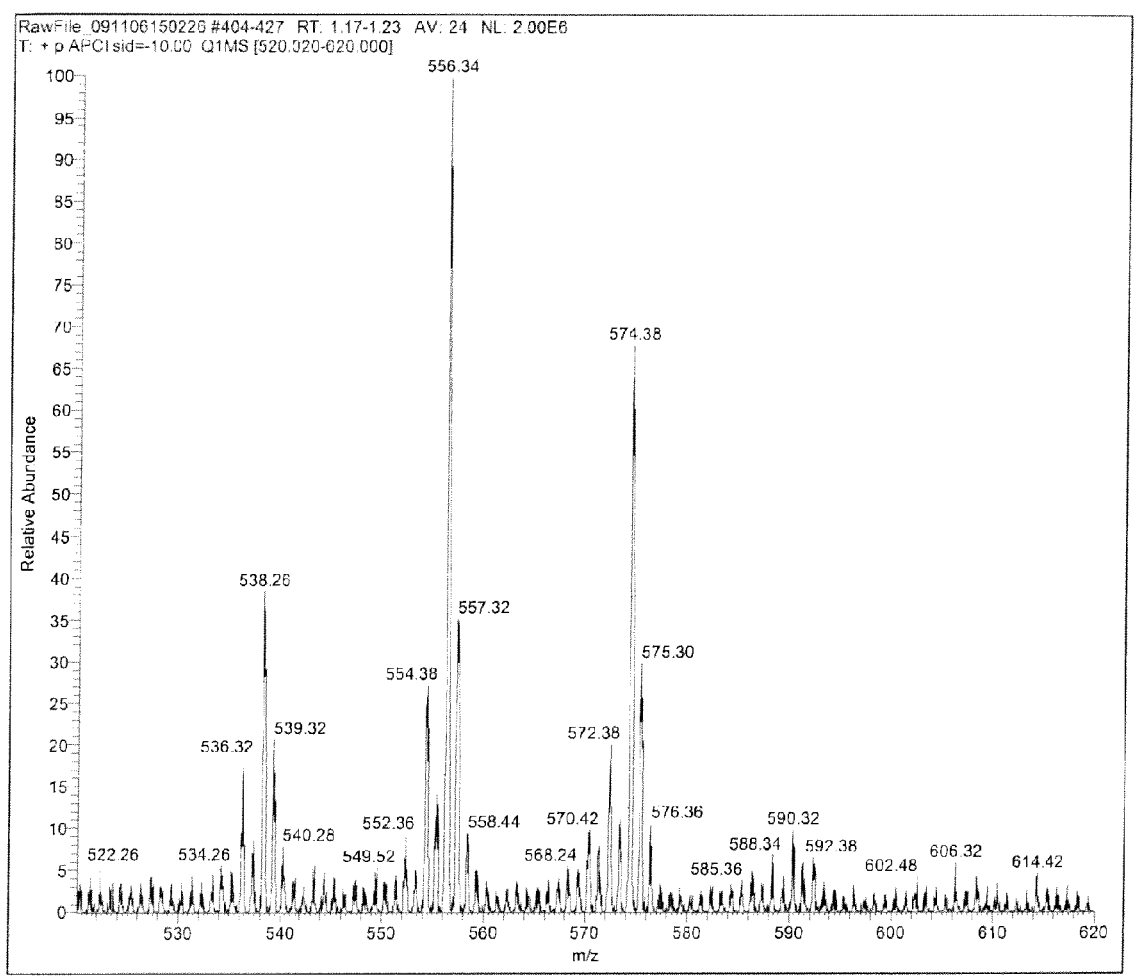
FIG. 8A shows an exemplary Q1 scan spectrum (covering the m/z range of about 520 to 620) for PTAD-1α,25-hydroxyvitamin $D_3$ ions.
Figure 8B:
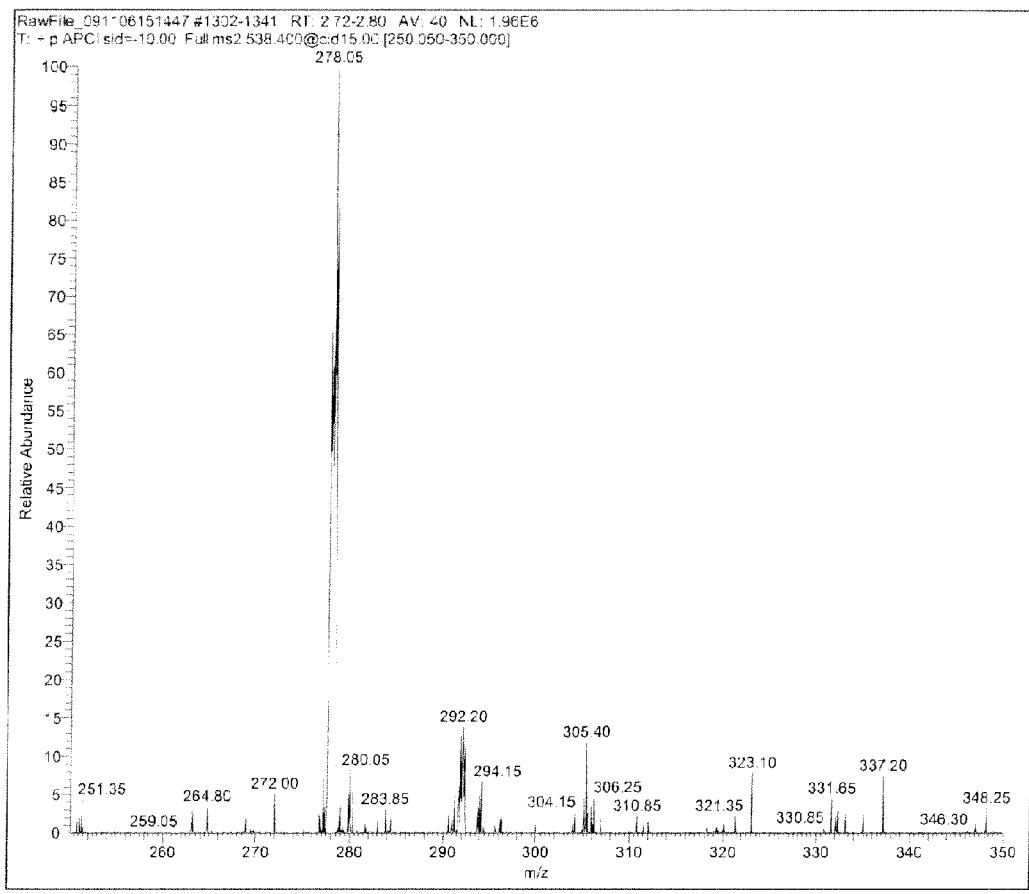
FIG. 8B shows an exemplary product ion spectra (covering the m/z range of about 250 to 350) for fragmentation of the PTAD-1α,25-dihydroxyvitamin $D_3$-PTAD precursor ion with m/z of about 538.4.
Figure 8C:
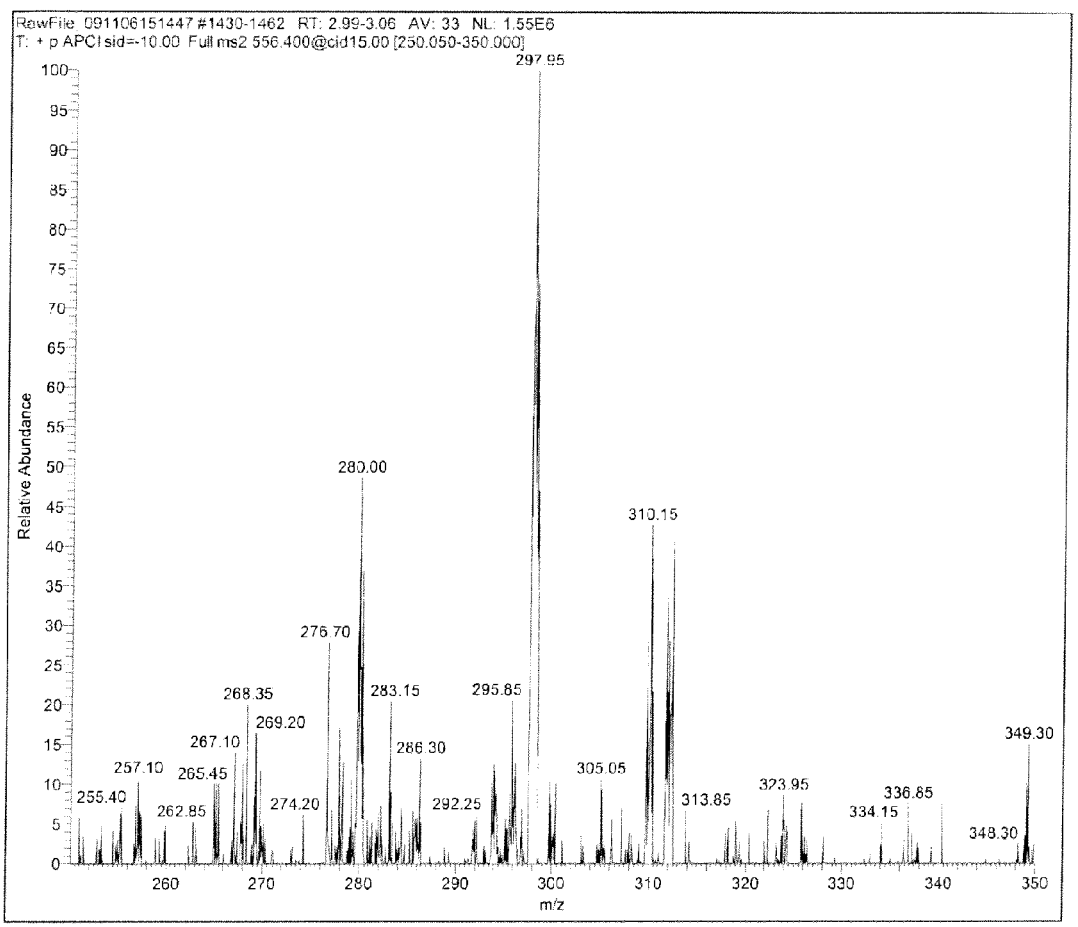
FIG. 8C shows an exemplary product ion spectra (covering the m/z range of about 250 to 350) for fragmentation of the PTAD-1α,25-dihydroxyvitamin $D_3$ precursor ion with m/z of about 556.4.
Figure 8D:
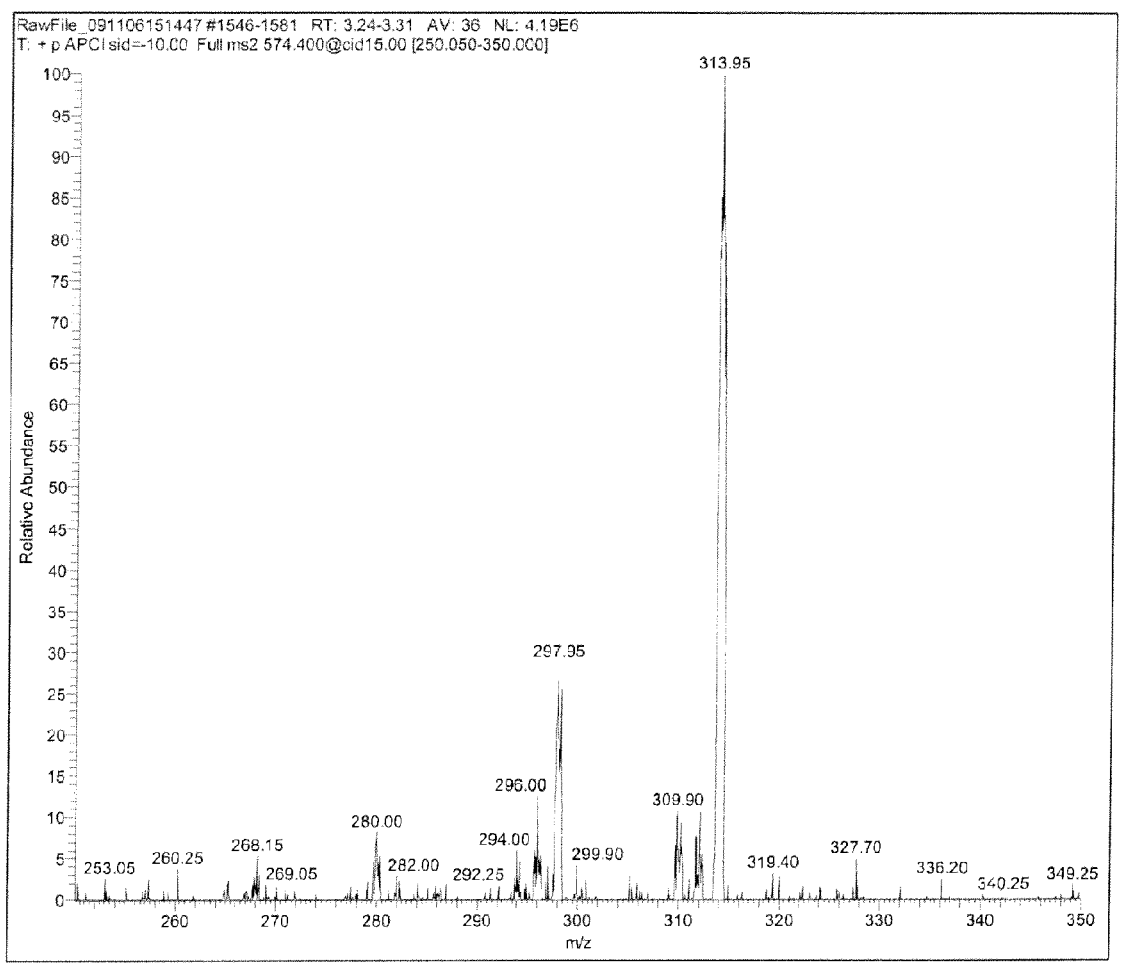
FIG. 8D shows an exemplary product ion spectra (covering the m/z range of about 250 to 350) for fragmentation of the PTAD-1α,25-dihydroxyvitamin $D_3$ precursor ion with m/z of about 574.4. Details are described in Example 6.
Figure 9A:
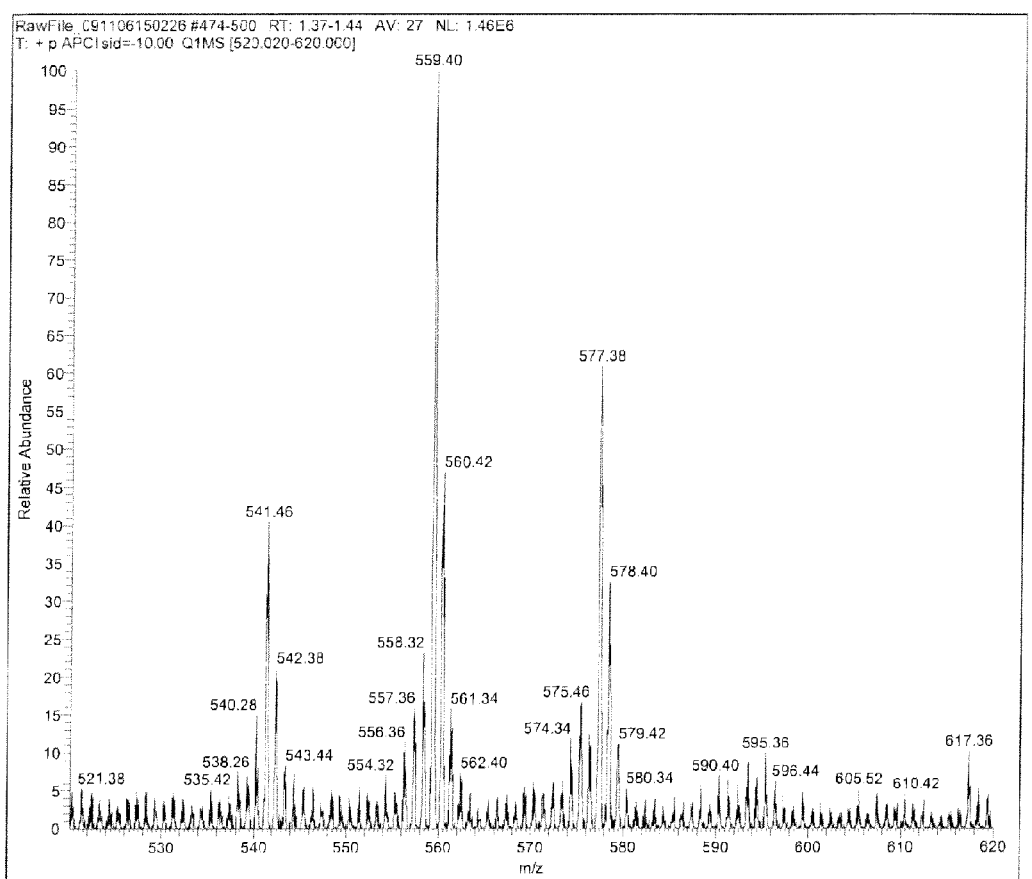
FIG. 9A shows an exemplary Q1 scan spectrum (covering the m/z range of about 520 to 620) for PTAD-1α,25-dihydroxyvitamin $D_3$-[6, 19, 19]-$^2H_3$ ions.
Figure 9B:
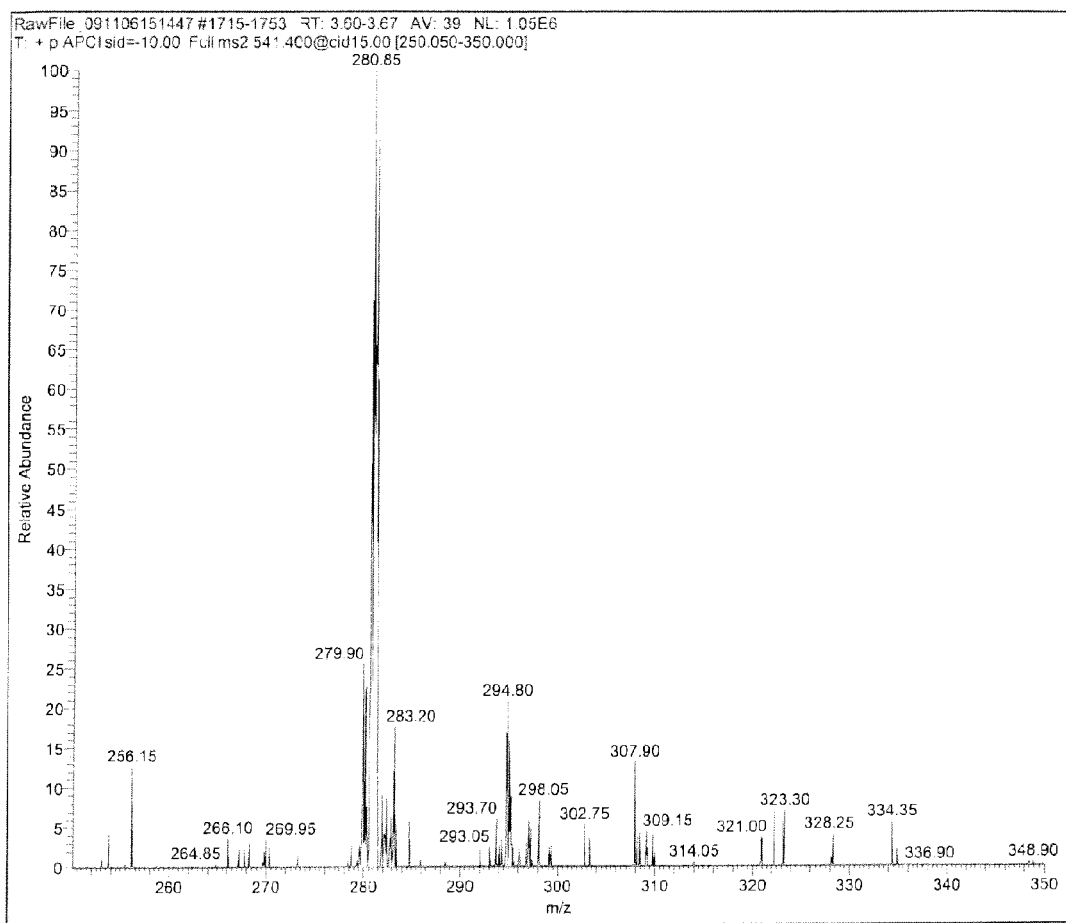
FIG. 9B shows an exemplary product ion spectra (covering the m/z range of about 250 to 350) for fragmentation of the PTAD-1α,25-dihydroxyvitamin $D_3$-[6, 19, 19]-$^2H_3$ precursor ion with m/z of about 541.4.
Figure 9C:
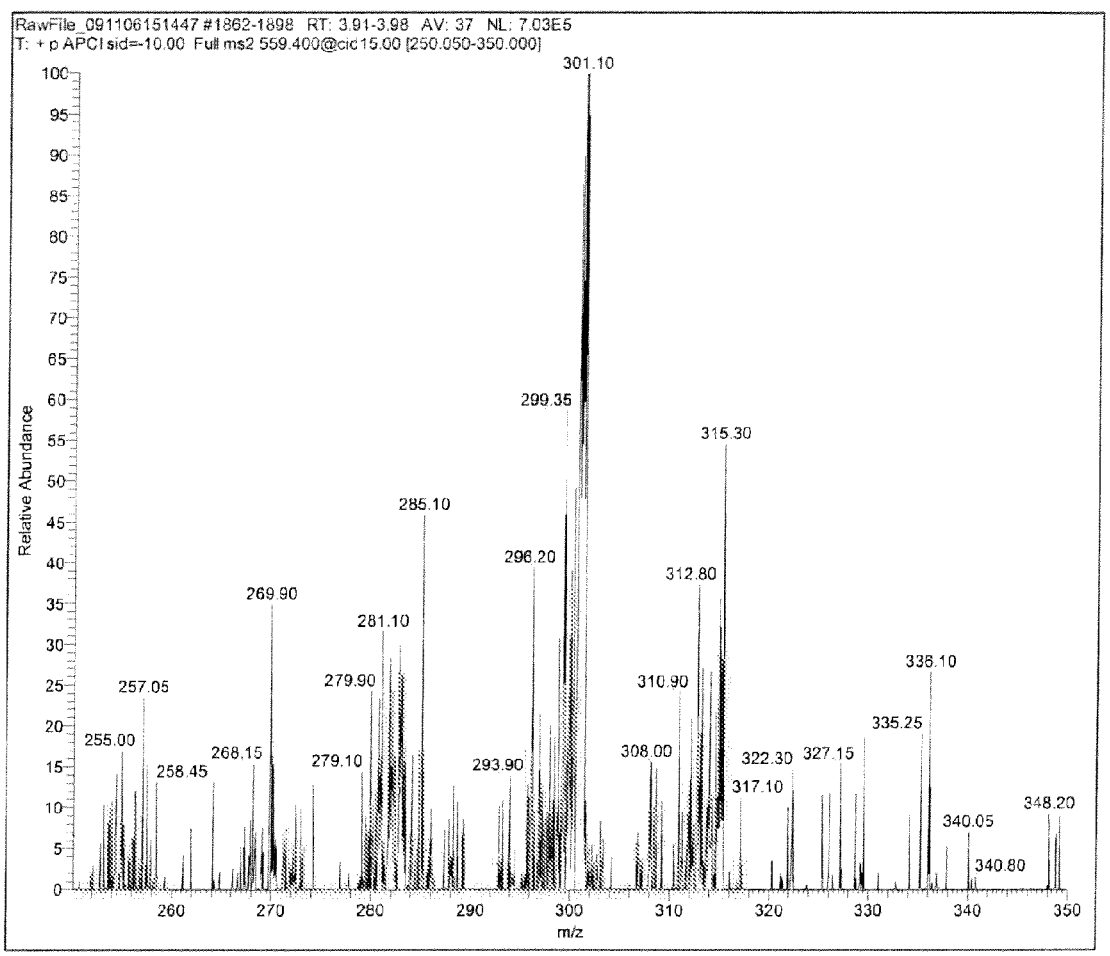
FIG. 9C shows an exemplary product ion spectra (covering the m/z range of about 250 to 350) for fragmentation of the PTAD-1α,25-dihydroxyvitamin $D_3$-[6, 19, 19]-$^2H_3$ precursor ion with m/z of about 559.4.
Figure 9D:
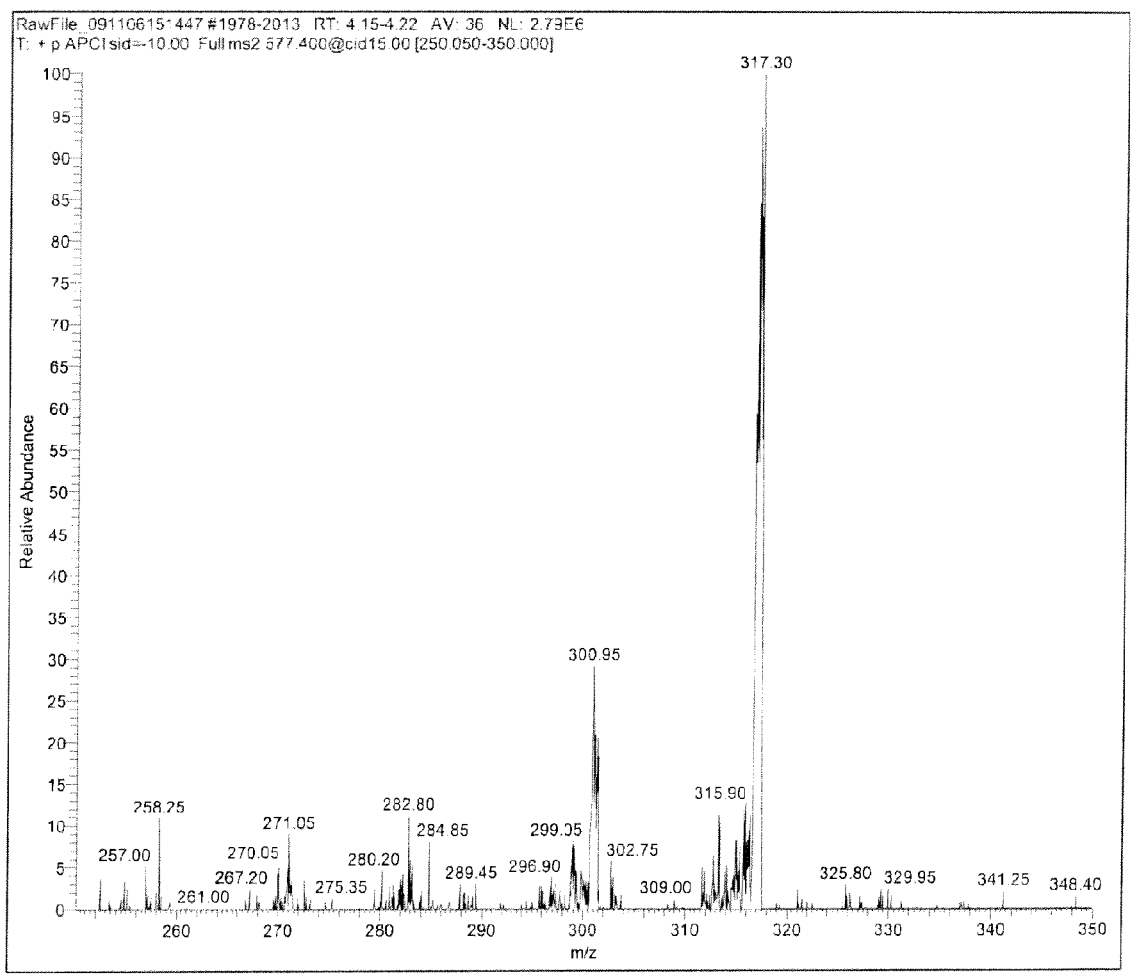
FIG. 9D shows an exemplary product ion spectra (covering the m/z range of about 250 to 350) for fragmentation of the PTAD-1α,25-dihydroxyvitamin $D_3$-[6, 19, 19]-$^2H_3$ precursor ion with m/z of about 577.4. Details are described in Example 6.
Figure 10A:
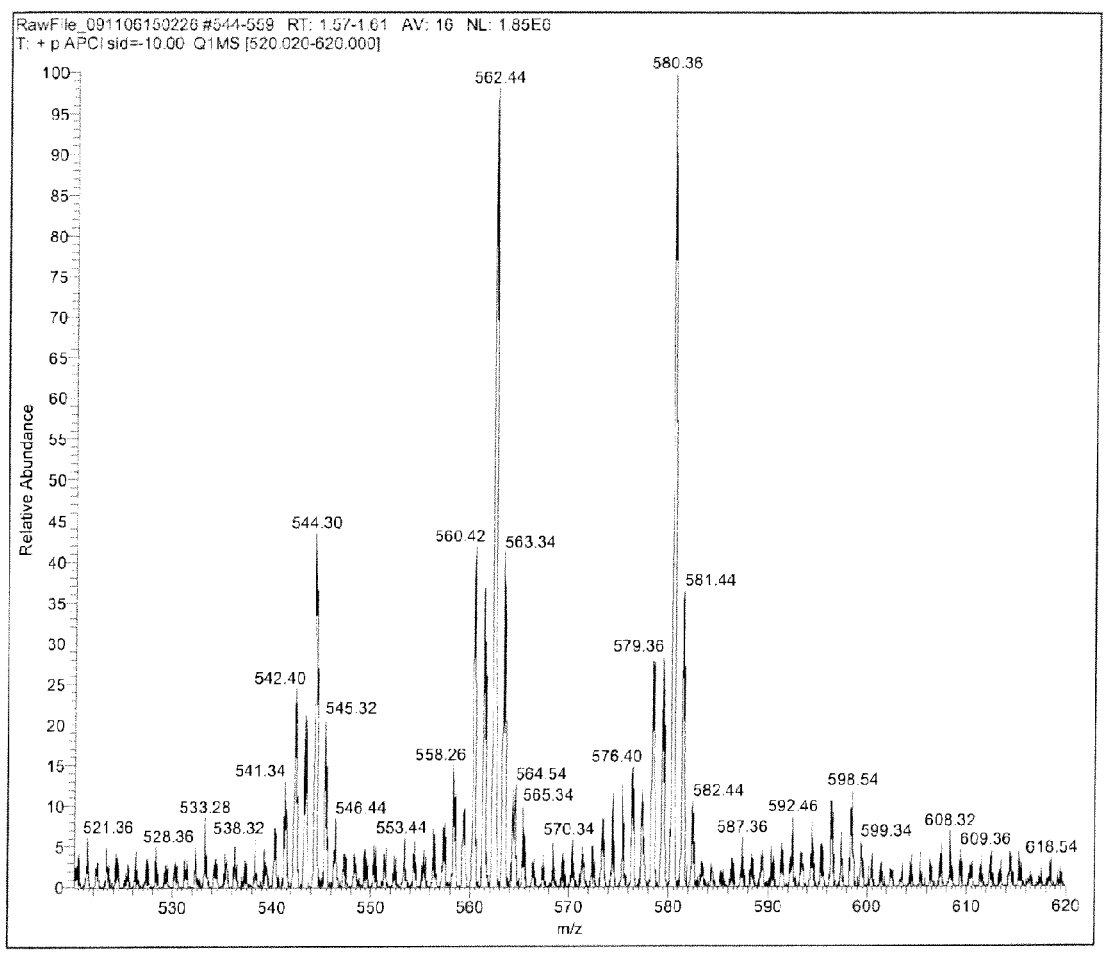
FIG. 10A shows an exemplary Q1 scan spectrum (covering the m/z range of about 520 to 620) for PTAD-1α,25-dihydroxyvitamin $D_3$-[26, 26, 26, 27, 27, 27]-$^2H_6$ ions.
Figure 10B:
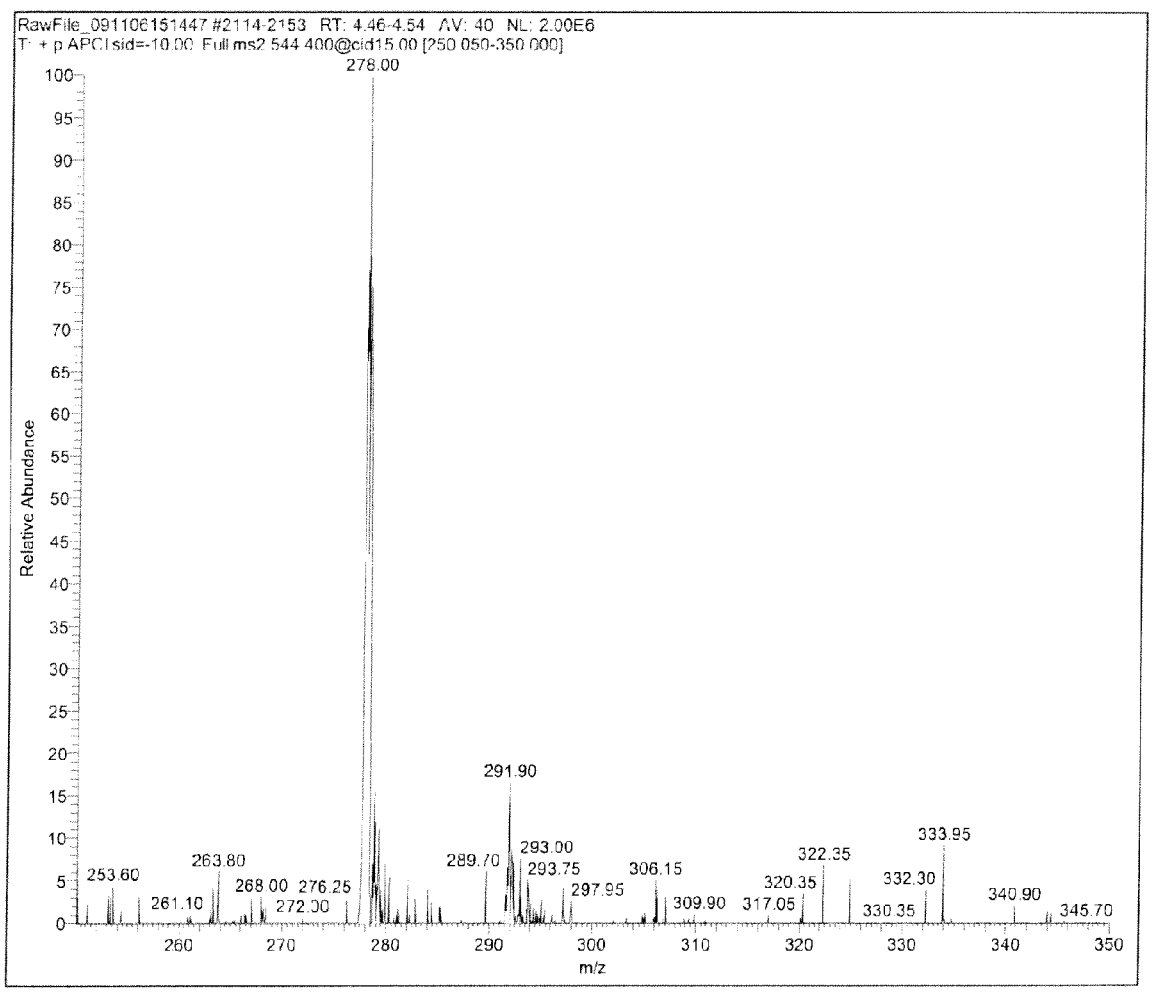
FIG. 10B shows an exemplary product ion spectra (covering the m/z range of about 250 to 350) for fragmentation of the PTAD-1α,25-dihydroxyvitamin $D_3$-[26, 26, 26, 27, 27, 27]-$^2H_6$ precursor ion with m/z of about 544.4.
Figure 10C:
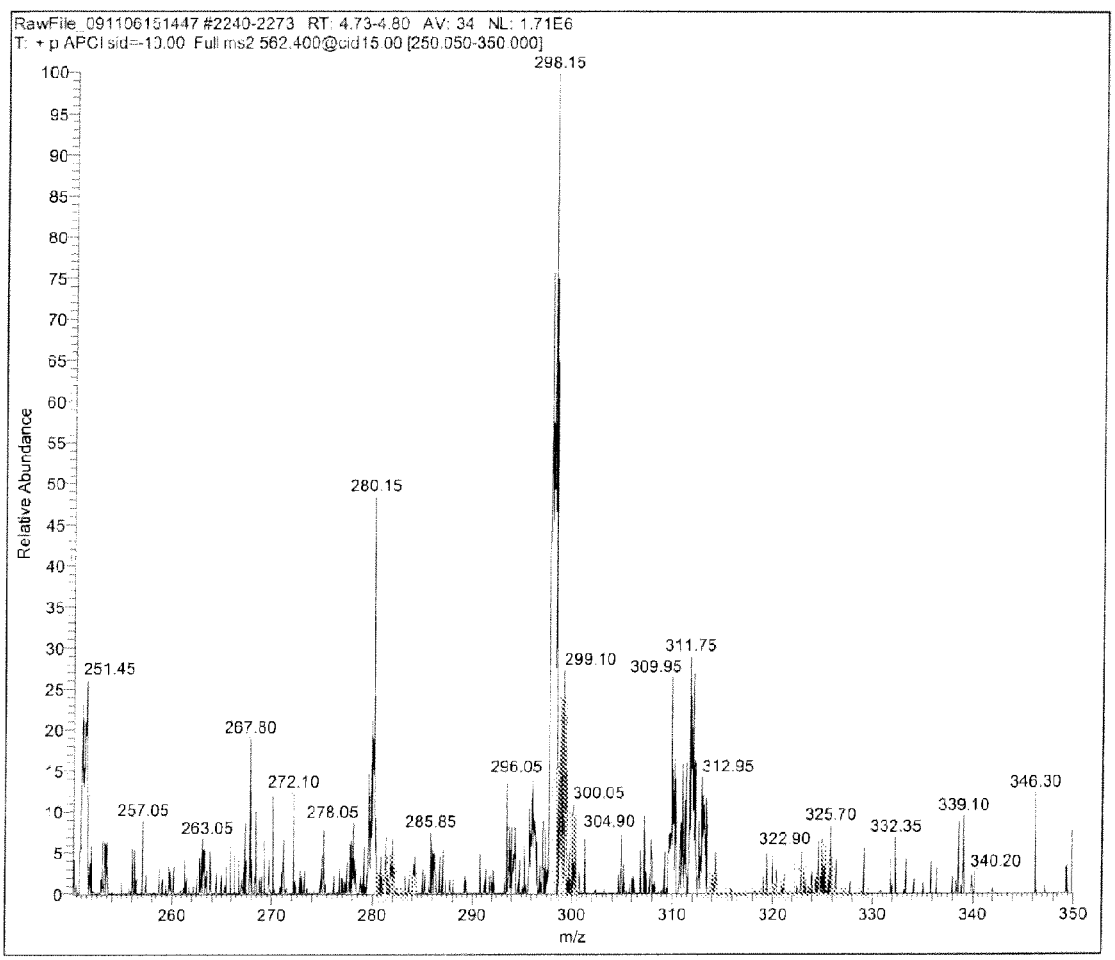
FIG. 10C shows an exemplary product ion spectra (covering the m/z range of about 250 to 350) for fragmentation of the PTAD-1α,25-dihydroxyvitamin $D_3$-[26, 26, 26, 27, 27, 27]-$^2H_6$ precursor ion with m/z of about 562.4.
Figure 10D:
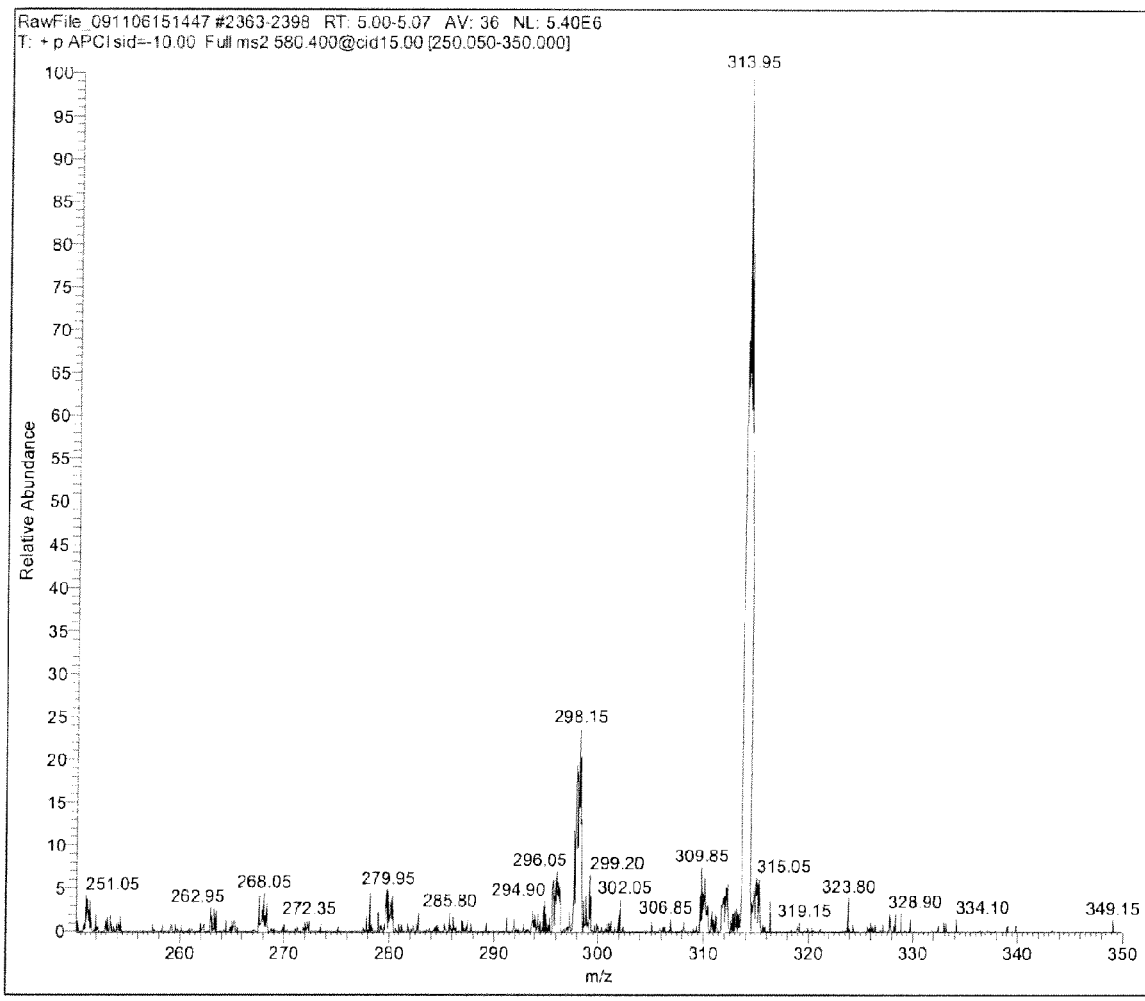
FIG. 10D shows an exemplary product ion spectra (covering the m/z range of about 250 to 350) for fragmentation of the PTAD-1α,25-dihydroxyvitamin $D_3$-[26, 26, 26, 27, 27, 27]-$^2H_6$ precursor ion with m/z of about 580.4. Details are described in Example 6.

Exemplary Q1 scan spectra from the analysis of PTAD-1α,25-hydroxyvitamin $D_3$, PTAD-1α,25-dihydroxyvitamin $D_3$-[6, 19, 19]-$^2H_3$, and PTAD-1α,25-dihydroxyvitamin $D_3$-[26, 26, 26, 27, 27, 27]-$^2H_6$ are shown in FIGS. 8A, 9A, and 10A, respectively. These spectra were collected with LDTD-MS/MS according to Example 4 by scanning Q1 across a m/z range of about 520 to 620.

Exemplary product ion scans generated from three different precursor ions for each of PTAD-1α,25-hydroxyvitamin $D_3$, PTAD-1α,25-dihydroxyvitamin $D_3$-[6, 19, 19]-$^2H_3$, and PTAD-1α,25-dihydroxyvitamin $D_3$-[26, 26, 26, 27, 27, 27]-$2H_6$ are presented in FIGS. 8B-D, 9A-D, and 10B-D, respectively. The precursor ions selected in Q1 and the collision energies used to generate these product ion spectra are indicated in Table 7.

Exemplary MRM transitions for the quantitation of PTAD-1α,25-hydroxyvitamin $D_3$ include fragmenting a precursor ion with a m/z of about 538.4 to a product ion with a m/z of about 278.1; fragmenting a precursor ion with a m/z of about 556.4 to a product ion with a m/z of about 298.0; and fragmenting a precursor ion with a m/z of about 574.4 to a product ion with a m/z of about 313.0. Exemplary MRM transitions for the quantitation of PTAD-1α,25-dihydroxyvitamin $D_3$-[6, 19, 19]-$^2H_3$ include fragmenting a precursor ion with a m/z of about 541.4 to a product ion with a m/z of about 280.9; fragmenting a precursor ion with a m/z of about 559.4 to a product ion with a m/z of about 301.1; and fragmenting a precursor ion with a m/z of about 577.4 to a product ion with a m/z of about 317.3. Exemplary MRM transitions for the quantitation of PTAD-1α,25-dihydroxyvitamin $D_2$-[26, 26, 26, 27, 27, 27]-$^2H_6$ include fragmenting a precursor ion with a m/z of about 544.4 to a product ion with a m/z of about 278.0; fragmenting a precursor ion with a m/z of about 562.4 to a product ion with a m/z of about 298.2; and fragmenting a precursor ion with a m/z of about 580.4 to a product ion with a m/z of about 314.0. However, as can be seen in the product ion scans in FIGS. 8B-D, 9B-D, and 10B-D, several other product ions are generated upon fragmentation of the precursor ions. Additional product ions may be selected from those indicated in FIGS. 8B-D, 9B-D, and 10B-D to replace or augment the exemplary fragment ions.

TABLE 7

Precursor Ions and Collision Cell Energies for Fragmentation of PTAD-1α,25-dihydroxyvitamin $D_3$, PTAD-1α,25-dihydroxyvitamin $D_3$-[6,19,19]-$^2H_3$, and PTAD-1α,25-dihydroxyvitamin $D_3$-[26,26,26,27,27,27]-$^2H_6$

| Analyte | Precursor Ion (m/z) | Energy of Collision Cell (V) |
|---|---|---|
| PTAD-1α,25-dihydroxyvitamin $D_3$ | 538.4, 556.4, 574.4 | 15 |
| PTAD-1α,25-dihydroxyvitamin $D_3$-[6,19,19]-$^2H_3$ | 541.4, 559.4, 577.4 | 15 |
| PTAD-1α,25-dihydroxyvitamin $D_3$-[26,26,26,27,27,27]-$^2H_6$ | 544.4, 562.4, 580.4 | 15 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A method for determining the amount of 1α,25-dihydroxyvitamin $D_2$ (1α,25(OH)$_2D_2$) in a sample by mass spectrometry, the method comprising the steps of:
   ionizing 1α,25(OH)$_2D_2$ from the sample to generate one or more 1α,25(OH)$_2D_2$ ions detectable by mass spectrometry, wherein said one or more 1α,25(OH)$_2D_2$ ions comprise one or more ions selected from the group consisting of ions with a mass-to-charge ratio of 393.1±0.5 and 225.0±0.5;
   determining the amount of one or more of the 1α,25(OH)$_2D_2$ ions by mass spectrometry; and
   relating the determined amount of 1α,25(OH)$_2D_2$ ions to the amount of 1α,25(OH)$_2D_2$ in the sample.

2. The method of claim 1, wherein the mass spectrometry is tandem mass spectrometry.

3. The method of claim 2, wherein the one or more 1α,25(OH)$_2D_2$ ions comprise a precursor ion with a mass-to-charge ratio of 393.1±0.5 and one or more fragment ions of said precursor ion selected from the group of ions with a mass-to-charge ratio of 157.0±0.5 and 225.0±0.5.

4. The method of claim 1, wherein the sample is subjected to liquid chromatography prior to mass spectrometry.

5. The method of claim 3, wherein the sample is subjected to chromatography prior to mass spectrometry.

6. The method of claim 1, wherein 1α,25(OH)$_2D_2$ is ionized with atmospheric pressure chemical ionization (APCI).

7. The method of claim 1, wherein the sample comprises a biological sample from a human, and the determined amount of 1α,25(OH)$_2D_2$ is the amount in the sample when taken from a human.

8. The method of claim 1, wherein the sample comprises human plasma or serum, and the determined amount of 1α,25(OH)$_2D_2$ is the amount in the sample when taken from a human.

9. A method for determining the amount of 1α,25-dihydroxyvitamin $D_2$ (1α,25(OH)$_2D_2$) in a biological sample when taken from a human, by mass spectrometry, the method comprising the steps of:
   ionizing 1α,25(OH)$_2D_2$ from the sample to generate one or more 1α,25(OH)$_2D_2$ ions detectable by mass spectrometry;
   determining the amount of one or more of the 1α,25(OH)$_2D_2$ ions by mass spectrometry; and
   relating the determined amount of 1α,25(OH)$_2D_2$ ions to the amount of 1α,25(OH)$_2D_2$ in the sample;
   wherein said one or more 1α,25(OH)$_2D_2$ ions comprise one or more ions selected from the group consisting of ions with a mass-to-charge ratio of 375.1±0.5, 105.3±0.5, and 157.0±0.5.

10. The method of claim 9, further comprising subjecting 1α,25(OH)$_2D_2$ from the sample to liquid chromatography prior to ionization.

11. The method of claim 8, wherein the mass spectrometry is tandem mass spectrometry.

12. The method of claim 11, wherein the one or more 1α,25(OH)$_2D_2$ ions comprise a precursor ion with a mass-to-charge ratio of 375.1±0.5 and one or more fragment ions of said precursor ion selected from the group of ions with a mass-to-charge ratio of 105.3±0.5 and 157.0±0.5.

13. The method of claim 9, wherein 1α,25(OH)$_2D_2$ is ionized with atmospheric pressure chemical ionization (APCI).

14. The method of claim 9, wherein said biological sample comprises human plasma or serum.

15. A method for determining the amount of 1α,25-dihydroxyvitamin $D_2$ (1α,25(OH)$_2D_2$) in a sample by mass spectrometry, the method comprising the steps of:
   enriching 1α,25(OH)$_2D_2$ from a sample by liquid chromatography;
   ionizing the enriched 1α,25(OH)$_2D_2$ to generate one or more 1α,25(OH)$_2D_2$ ions detectable by mass spectrometry;
   determining the amount of one or more of the 1α,25(OH)$_2D_2$ ions by mass spectrometry; and
   relating the determined amount of 1α,25(OH)$_2D_2$ ions to the amount of 1α,25(OH)$_2D_2$ in the sample;
   wherein said one or more 1α,25(OH)$_2D_2$ ions comprise one or more ions selected from the group consisting of ions with a mass-to-charge ratio of 375.1±0.5±0.5, 105.3±0.5, and 157.0±0.5.

16. The method of claim 15, wherein the mass spectrometry is tandem mass spectrometry.

17. The method of claim 16, wherein the one or more 1α,25(OH)$_2D_2$ ions comprise a precursor ion with a mass-to-charge ratio of 375.1±0.5 and one or more fragment ions of said precursor ion selected from the group of ions with a mass-to-charge ratio of 105.3±0.5 and 157.0±0.5.

18. The method of claim 15, wherein 1α,25(OH)$_2D_2$ is ionized with atmospheric pressure chemical ionization (APCI).

19. The method of claim 15, wherein the sample comprises human plasma or serum, and the determined amount of 1α,25(OH)$_2D_2$ is the amount in the sample when taken from a human.

20. A method for determining the amount of 1α,25-dihydroxyvitamin $D_2$ 1α,25(OH)$_2D_2$) in a sample by mass spectrometry, the method comprising the steps of:
   ionizing 1α,25(OH)$_2D_2$ from the sample by atmospheric pressure chemical ionization (APCI) to generate one or more 1α,25(OH)$_2D_2$ ions detectable by mass spectrometry;
   determining the amount of one or more of the 1α,25(OH)$_2D_2$ ions by mass spectrometry; and
   relating the determined amount of 1α,25(OH)$_2D_2$ ions to the amount of 1α,25(OH)$_2D_2$ in the sample;
   wherein said one or more 1α,25(OH)$_2D_2$ ions comprise one or more ions selected from the group consisting of ions with a mass-to-charge ratio of 375.1±0.5, 105.3±0.5, and 157.0±0.5.

21. The method of claim 20, further comprising subjecting 1α,25(OH)$_2D_2$ from a sample to chromatography prior to ionization.

22. The method of claim 20, wherein the mass spectrometry is tandem mass spectrometry.

23. The method of claim 22, wherein the one or more 1α,25(OH)$_2D_2$ ions comprise a precursor ion with a mass-to-charge ratio of 375.1±0.5 and one or more fragment ions of said precursor ion selected from the group of ions with a mass-to-charge ratio of 105.3±0.5 and 157.0±0.5.

24. The method of claim 20, wherein the sample comprises human plasma or serum, and the determined amount of 1α,25(OH)$_2D_2$ is the amount in the sample when taken from a human.

* * * * *